(12) United States Patent
Gross et al.

(10) Patent No.: US 7,772,365 B2
(45) Date of Patent: Aug. 10, 2010

(54) SOLUBLE RECEPTOR BR43X2

(75) Inventors: Jane A. Gross, Seattle, WA (US); Wenfeng Xu, Mukilteo, WA (US); Karen L. Madden, Bellevue, WA (US); David P. Yee, Cambridge, MA (US)

(73) Assignee: Zymogenetics, Inc., Seattle, WA (US)

( * ) Notice: Subject to any disclaimer, the term of this patent is extended or adjusted under 35 U.S.C. 154(b) by 936 days.

(21) Appl. No.: 11/458,968

(22) Filed: Jul. 20, 2006

(65) Prior Publication Data
US 2006/0286093 A1    Dec. 21, 2006

Related U.S. Application Data

(60) Division of application No. 09/627,206, filed on Jul. 27, 2000, which is a continuation-in-part of application No. 09/569,245, filed on May 11, 2000, which is a continuation-in-part of application No. 09/479,856, filed on Jan. 7, 2000, now abandoned.

(60) Provisional application No. 60/115,068, filed on Jan. 7, 1999, provisional application No. 60/169,890, filed on Dec. 9, 1999.

(51) Int. Cl.
| | |
|---|---|
| A61K 38/17 | (2006.01) |
| A61K 39/395 | (2006.01) |
| C07H 21/04 | (2006.01) |
| C12P 21/04 | (2006.01) |
| C07K 14/74 | (2006.01) |

(52) U.S. Cl. .................... 530/324; 530/300; 530/350; 514/12

(58) Field of Classification Search .................. None
See application file for complete search history.

(56) References Cited

U.S. PATENT DOCUMENTS

| | | | |
|---|---|---|---|
| 4,331,647 A | 5/1982 | Goldenberg | |
| 4,486,533 A | 12/1984 | Lambowitz | |
| 4,579,821 A | 4/1986 | Palmiter et al. | |
| 4,599,311 A | 7/1986 | Kawasaki | |
| 4,601,978 A | 7/1986 | Karin | |
| 4,615,974 A | 10/1986 | Kingsman et al. | |
| 4,656,134 A | 4/1987 | Ringold | |
| 4,661,454 A | 4/1987 | Botstein et al. | |
| 4,713,339 A | 12/1987 | Levinson et al. | |
| 4,784,950 A | 11/1988 | Hagen et al. | |
| 4,845,075 A | 7/1989 | Murray et al. | |
| 4,870,008 A | 9/1989 | Brake | |
| 4,882,279 A | 11/1989 | Cregg | |
| 4,931,373 A | 6/1990 | Kawasaki et al. | |
| 4,935,349 A | 6/1990 | McKnight et al. | |
| 4,946,778 A | 8/1990 | Ladner et al. | |
| 4,956,288 A | 9/1990 | Barsoum | |
| 4,977,092 A | 12/1990 | Bitter | |
| 4,990,446 A | 2/1991 | Oberto et al. | |
| 5,037,743 A | 8/1991 | Welch et al. | |
| 5,063,154 A | 11/1991 | Fink et al. | |
| 5,139,936 A | 8/1992 | Botstein et al. | |
| 5,143,830 A | 9/1992 | Holland et al. | |
| 5,155,027 A | 10/1992 | Sledziewski et al. | |
| 5,162,222 A | 11/1992 | Guarino et al. | |
| 5,162,228 A | 11/1992 | Sumino et al. | |
| 5,208,146 A | 5/1993 | Irie | |
| 5,223,409 A | 6/1993 | Ladner et al. | |
| 5,403,484 A | 4/1995 | Ladner et al. | |
| 5,523,227 A | 6/1996 | Bram et al. | |
| 5,541,291 A | 7/1996 | Keene | |
| 5,567,584 A | 10/1996 | Sledziewski et al. | |
| 5,571,698 A | 11/1996 | Ladner et al. | |
| 5,595,721 A | 1/1997 | Kaminski et al. | |
| 5,637,677 A | 6/1997 | Greene et al. | |
| 5,650,550 A | 7/1997 | Korach et al. | |
| 5,693,762 A | 12/1997 | Queen et al. | |
| 5,716,808 A | 2/1998 | Ramond | |
| 5,736,383 A | 4/1998 | Raymond | |
| 5,739,277 A | 4/1998 | Presta et al. | |
| 5,969,102 A | 10/1999 | Bram et al. | |
| 6,015,801 A | 1/2000 | Daifotis et al. | |
| 6,316,222 B1 | 11/2001 | Bram et al. | |
| 6,500,428 B1 | 12/2002 | Bram et al. | |
| 6,537,540 B1 | 3/2003 | Burstein et al. | |
| 6,716,576 B1 | 4/2004 | Yu et al. | |

(Continued)

FOREIGN PATENT DOCUMENTS

AU    2006201471    5/2006

(Continued)

OTHER PUBLICATIONS

Grass et al. (International Immunology, 1995, vol. 7 No. 7, pp. 1093-1106).*

(Continued)

*Primary Examiner*—Robert A Zeman
(74) *Attorney, Agent, or Firm*—Howrey LLP

(57) ABSTRACT

Soluble, secreted tumor necrosis factor receptor polypeptides, polynucleotides encoding the polypeptides, and related compositions and methods are disclosed. The polypeptides comprise one cysteine-rich repeat that is homologous to other tumor necrosis factor receptors, such as transmembrane activator and CAML-interactor (TACI). The polypeptides may be used for detecting ligands, agonists and antagonists. The polypeptides may also be used in methods that modulate B cell activation.

1 Claim, 16 Drawing Sheets

U.S. PATENT DOCUMENTS

| | | | |
|---|---|---|---|
| 6,774,106 | B2 | 8/2004 | Theill et al. |
| 7,501,487 | B1 | 3/2009 | Mangelsdorf et al. |
| 2003/0022233 | A1 | 1/2003 | Goodwin et al. |
| 2003/0103986 | A1 | 6/2003 | Rixon et al. |
| 2004/0013674 | A1 | 1/2004 | Ambrose et al. |
| 2005/0070689 | A1 | 3/2005 | Dixit et al. |
| 2005/0183148 | A1 | 8/2005 | Bram et al. |
| 2006/0034852 | A1 | 2/2006 | Rixon et al. |
| 2006/0067933 | A1 | 3/2006 | Gross et al. |
| 2006/0073146 | A1 | 4/2006 | Ashkenazi et al. |
| 2006/0286093 | A1 | 12/2006 | Gross et al. |
| 2007/0071760 | A1 | 3/2007 | Broly et al. |
| 2007/0264689 | A1 | 11/2007 | Gross et al. |
| 2007/0269443 | A1 | 11/2007 | Kalled et al. |

FOREIGN PATENT DOCUMENTS

| | | |
|---|---|---|
| EP | 0869180 A1 | 10/1998 |
| EP | 1666052 | 6/2006 |
| GB | 9828628.9 | 12/1998 |
| WO | WO 91/11465 | 8/1991 |
| WO | WO 94/06463 | 3/1994 |
| WO | WO 94/09137 | 4/1994 |
| WO | WO 95/35501 | 12/1995 |
| WO | WO 96/18641 | 6/1996 |
| WO | WO 96/27011 | 9/1996 |
| WO | WO 97/09137 | 3/1997 |
| WO | WO 97/17450 | 5/1997 |
| WO | WO 97/17451 | 5/1997 |
| WO | WO 97/33902 | 9/1997 |
| WO | WO 98/02536 | 1/1998 |
| WO | WO 98/02565 | 1/1998 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/04001 | 1/1999 |
| WO | WO 99/11791 | 3/1999 |
| WO | WO 99/12964 | 3/1999 |
| WO | WO 99/12965 | 3/1999 |
| WO | WO 00/03995 | 1/2000 |
| WO | WO 00/39295 | 7/2000 |
| WO | WO 00/40714 | 7/2000 |
| WO | WO 00/40716 | 7/2000 |
| WO | WO 00/43032 | 7/2000 |
| WO | WO 00/50597 | 8/2000 |
| WO | WO 00/62790 | 10/2000 |
| WO | WO 00/67034 | 11/2000 |
| WO | WO 01/12812 A2 | 2/2001 |
| WO | WO 01/24811 A1 | 4/2001 |
| WO | PCT/JP01/06944 | 8/2001 |
| WO | WO 01/60397 | 8/2001 |
| WO | WO 01/77342 | 10/2001 |
| WO | WO 01/81417 | 11/2001 |
| WO | WO 01/87977 | 11/2001 |
| WO | WO 02/14504 | 2/2002 |
| WO | WO 02/38766 | 5/2002 |
| WO | WO 02/066516 | 8/2002 |
| WO | WO 02/094852 A2 | 11/2002 |
| WO | WO 03/001877 | 1/2003 |
| WO | WO 03/014294 | 2/2003 |
| WO | WO 03/055979 | 7/2003 |
| WO | WO 2005/005462 | 1/2005 |
| WO | WO 2005/042009 | 5/2005 |
| WO | WO 2006/052493 | 5/2006 |
| WO | WO 2006/068867 | 6/2006 |
| WO | WO 2007/019573 A2 | 2/2007 |
| WO | WO 2007/019575 A2 | 2/2007 |
| WO | WO 2007/019618 | 2/2007 |
| WO | WO 2007/134326 | 11/2007 |

OTHER PUBLICATIONS

Altschul, et al., Bull Math. Bio., vol. 48, pp. 603-666 (1986).
Anolik, J.H., et al., "New Treatments for SLE: Cell-Depleting and Anti-Cytokine Therapies," Best Practice & Research Clinical Rheumatology, vol. 19, No. 5, pp. 859-878 (2005).
Aviv, H., et al., "Purificaton of Biologically Active Globin Messenger RNA by Chromatography on Oligothymidylic acid Cellulose," Proc. Natl. Acad. Sci., vol. 69, pp. 1408-1412 (1972).
Bairoch, A., "The PROSITE Dictionary of Sites and Patterns in Proteins, Its Current Status," Nucleic Acids Research, vol. 21, No. 13, pp. 3097-3103 (1993).
Barlogie, B., et al. Extended Survival in Advanced and Refractory Multiple Myeloma After Single-Agent Thalidomide: Identification of Prognostic Factors in a Phase 2 Study of 169 Patients, Blood, vol. 98, No. 2, pp. 492-494 (2001).
Biosis Database, [online], Biosciences Information Service, Philadelphia, PA (Sep. 2008). Carbonatto, Michela, et al., Nonclinical Safety, Pharmacokinetics, and Pharmacodynamics of Atacicept, Database Accession No. PRV200800586339, Toxicological Sciences, vol. 105, No. 1, pp. 200-210 (Sep. 2008).
Bird, et al., Science, vol. 242, p. 423 (1988).
Birren, et al., EMBL Database Report for Accession No. AC003958, Jan. 6, 1998 (XP-002072294).
Bodmer, et al., "The Molecular Architecture of the TNF Superfamily," TRENDS in Biochemical Sciences, vol. 27, No. 1, pp. 19-24 (Jan. 2002).
Bonning, et al., J. Gen. Virol., vol. 75, pp. 1551-1556 (1994).
Bram, R.J. and G.R. Crabtree, "Calcium Signalling in T Cells Stimulated by a Cyclophilin B-Binding Protein," Nature, vol. 371, pp. 355-358 (Sep. 22, 1994).
Bram, R.J., et al., "Identification of the Immunophilins Capable of Mediating Inhibition of Signal Transduction by Cyclosporin A and FK506: Roles of Calcineurin Binding and Cellular Location," Molecular and Cellular Biology, vol, 13, No. 8, pp. 4760-4769 (Aug. 1993).
Brenner, S., et al., "Errors in Genome Annotation," Trends in Genetics, vol. 15, pp. 132-133 (1999).
Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology 111, pp. 2129-2138 (Nov. 1990).
Carter, et al., Proc. Nat. Acad. Sci., vol. 89, p. 42875 (1992).
Chan, A., et al., "Rescue Therapy Anti-CD20 Treatment in Neuroimmunologic Breakthrough Disease," J. Neurol. vol. 254, pp. 1604-1606 (2007).
Chazenbalk, Rapport, J. Biol. Chem., vol. 270, pp. 1543-1549 (1995).
Cheema, G., et al., "Elevated Serum B Lmphocyte Stimulator Levels in Patients With Systemic Immune-Based Rheumatic Diseases," Arthritis & Rheumatism, vol. 44., No. 6, pp. 1313-1319 (2001).
Cheson, B., et al., "National Cancer Institute-Sponsored Working Group Guidelines for Chronic Lymphocytic Leukemia: Revised Guidelines for Diagnosis and Treatment," Blood, vol. 87, No. 12, pp. 4990-4997 (1996).
Chirgwin, et al., Biochemistry, vol. 18, pp. 52-94 (1979).
Ciccarone, et al., Focus, vol. 15, p. 80 (1993).
Claros, M.G., et al., Comput. Appl. Biosci., vol. 10, pp. 685-686 (1994).
Clipstone, N. A. and G.R. Crabtee, "Identification of Calcineurin as a Key Signalling Enzyme in T-lymphocyte Activation," Nature, vol. 357, pp. 695-697 (Jun. 25, 1992).
Corsaro, Pearson Somatic Cell Genetics, vol. 7, p. 603 (1981).
Cosman, Stem Cells, vol. 12, pp. 440-455 (1994).
Courtenay-Luck, et al., Genetic Manipulation of Monoclonal Antibodies, Cambridge University Press article, "Monoclonal Antibodies, Production, Engineering and Clinical Application," p. 166 (1995).
Crabtee and Clipstone, Annu. Rev. Biochem., vol. 63, pp. 1045-1083 (1994).

Cyster, Nature Immunol., vol. 1, pp. 9-10 (2000).
Database Accession No. 014836, "Tumor Necrosis Factor Receptor Superfamily Member 13B" (2007).
Database Accession No. P20333, "Tumor Necrosis Factor Receptor 2 Precursor," (1995).
Davidson and Diamond, "Autoimmune Diseases," N Engl J Med, vol. 345, No. 5, pp. 340-350 (Aug. 2, 2001).
DiLillo, D.J., et al., "Maintenance of Long-Lived Plasma Cells and Serological Memory Despite Mature and Memory B Cell Depletion during CD20 Immunotherapy in Mice," The Journal of Immunology, vol. 180, pp. 361-371 (2008).
Ding and Jones, "Belimumab Human Genome Sciences/Cambridge Antibody Technology," Current Opinion in Investigational Drugs, vol. 7, No. 5, pp. 464-472 (2006).
Do, R., "Attenuation of Apoptosis Underlies B Lymphocyte Stimulator Enhancement of Humoral Immune Response." J. Exp. Med., vol. 192, No. 7, pp. 953-964 (2000).
Durfee, T., et al., Genes Dev., vol. 7, pp. 555-569 (1993).
Dynan, T., Nature, vol. 316, pp. 774-778 (1985).
Eisen, "Aberrant Immune Responses," General Immunology, J.B. Lippincott Company, pp. 215-225 (1990).
Emmel, E.A., et al., "Cyclosporin A Specifically Inhibits Function of Nuclear Proteins Involved in T Cell Activation," Science, vol. 246, pp. 1617-1620 (Dec. 22, 1989).
European Search Report of EP 05020384.3 dated Apr. 27, 2007.
European Search Report of EP 03016020 dated Jul. 10, 2003.
European Search Report of EP 05018984 dated Jan. 25, 2006.
European Search Report of EP 05018985 dated Jan. 16, 2006.
European Supplementary & Partial Search Report of EP 02734478 dated Dec. 7, 2007.
Excoffon, K., et al., "The Role of the Extracellular Domain in the Biology of the Coxsackievirus and Adenovirus Receptor," Am. J. Respir. Cell. Mol. Biol., vol. 32, pp. 498-503 (2005).
Falk, et al., "The Systemic Amyloidoses," N Engl J Med, vol. 337, No. 13, pp. 898-909 (Sep. 25, 1997).
Feldmann and Maini, "The Role of Cytokines in the Pathogenesis of Rheumatoid Arthritis," Rheumatology, vol. 38, Suppl. 2, pp. 3-7 (1999).
Feldmann, et al., "Evaluation of the Role of Cytokines in Autoimmune Disease: The Importance of TNFa in Rheumatoid Arthritis," Progress in Growth Factor Research, vol. 4, pp. 247-255 (1992).
Fiering, S., et al., "Single Cell Assay of a Transcription Factor Reveals a Threshold in Transcription Activated by Signals Emanating from the T-cell Antigen Receptor," Genes & Development, vol. 4, pp. 1823-1834 (1990).
Friedman, J. and I. Weissman, "Two Cytoplasmic Candidates for Immunophilin Action Are Revealed by Affinity for a New Cyclophilin: One in the Presence and One in the Absence of CsA," Cell, vol. 66, pp. 799-806 (Aug. 23, 1991).
Gao, X., et al., "Advanced Transgenic and Gene-Targeting Approaches," Neurochemical Research, vol. 24, No. 9, pp. 1181-1188 (1999).
Garnier, et al., Cytotechnol., vol. 15, pp. 145-155 (1994).
Ginzler, et al., "Safety Pharmacokinetic and Pharmacodynamic Results of a Phase 1 Single and Double Dose-Escalation Study of LymphoStat-B (Human Monoclonal Antibody to BLyS) in SLE Patients," American College of Rheumatology Abstract Supplement, pp. S377 (2003).
Gleeson, et al., J. Gen. Microbiol., vol. 132, pp. 3459-3465 (1986).
Gotz-Ulrich, et al., Science, vol. 278, pp. 138-141 (1992).
Graham, et al., J. Gen. Viol., vol. 36, pp. 59-72 (1977).
Graham, Van der Eb, Virology, vol. 52, p. 456 (1973).
Grantham, et al., Nuc.Acids Res., vol. 8, pp. 1893-1912 (1980).
Green, et al., Nat. Genet, vol. 7, p. 13 (1994).
Groom, J., et al., "Association of BAFF/Blys Overexpression and Altered B Cell Differentiation with Sjogren's Syndrome," The Journal of Clinical Investigation, vol. 109, No. 1, pp. 59-68 (2002).
Grosjean, Fiers, Gene, vol. 18, pp. 199-209 (1982).
Gross, J., et al., "TACI-Ig Neutralizes Molecules Critical for B Cell Development and Autoimmune Disease: Impaired B Cell Maturation in Mice Lacking BlyS," Immunity, vol. 15, pp. 289-302 (2001).
Gross, J., et al., "TACI and BCMA are Receptors for a TNF Homologue Implicated in B-Cell Autoimmune Disease," Nature, vol. 404, pp. 995-999 (2000).
Grussenmeyer, et al., Proc. Natl. Acad. Sci., vol. 82, pp. 7952-7954 (1985).
Haas, et al., Cur. Biol., vol. 6, pp. 315-324 (1996).
Hahne, M., et al., "APRIL, a New Ligand of the Tumor Necrosis Factor Family, Stimulates Tumor Cell Growth," Journal of Experimental Medicine, vol. 188, No. 6, pp. 1185-1190 (1998).
Halpern et al., "Chronic Administration of Belimumab, a BLyS Antagonist, Decreases Tissue and Peripheral Blood B-Lymphocyte Populations in Cynomolgus Monkeys: Pharmacokinetic, Pharmacodynamic, and Toxicologic Effects," Toxicological Sciences, vol. 91, No. 2, pp. 586-599 (2006).
Hatzoglou, et al., J. Immunol., vol. 165, pp. 1322-1330 (2000) (XP002324045).
Hawley-Nelson, et al., Focus, vol. 15, p. 73 (1993).
Herrscher, R.F., et al., "The Immunoglobulin Heavy-chain Matrix-Associating Regions are Bound by Bright ά B Cell-Specific Trans-Activator That Describes a New DNA-Binding Protein Family," Genes & Development, vol. 9, pp. 30607-3082 (1995).
Hill-Perkins, Possee, J. Gen Virol., vol. 71, pp. 971-976 (1990).
Holloway, M.P. and R.J. Bram, "A Hydrophobic Domain of $Ca^{2+}$ Modulating Cyclophilin Ligand Modulates Calcium Influx Signaling in T Lymphocytes," The Journal of Biological Chemistry, vol. 271, No. 15, pp. 8549-8552 (1996).
Holloway, M.P. and R.J.Bram, "Co-localization of Calcium-modulating Cyclophilin Ligand with Intracellular Calcium Pools," Journal of Biological Chemistry, vol. 273, No. 26, pp. 16346-16350 (Jun. 26, 1992).
Holm, Nuc. Acids Res., vol. 14, pp. 3075-3087 (1986).
Hopp, Woods Proc. Nat. Acad. Sci., vol. 78, pp. 3824-3828 (1981).
Hoth, M. and R. Penner, Calcium Release-Activated Calcium Current in Rat Mast Cells, Journal of Physiology, vol. 465, pp. 359-386 (1993).
Houdebine, "Transgenic Animal Bioreactors," Transgenic Research, vol. 9, pp. 305-320 (2000).
Houdebine, L-M., 2002, Journal of Biotechnology, vol. 98, p. 145-160.
Huard, et al., "BAFF Production by Antigen-Presenting Cells Provides T Cell Co-Stimulation," International Immunology, vol. 16, No. 3, pp. 467-475 (2004).
Huard, et al., "T Cell Costimulation by the TNF Ligand BAFF," Journal of Immunology, vol. 167, pp. 6225-6231 (2001).
Hubbard, M.J., et al., vol. 28, pp. 1868-1874 (1989).
Hymowitz, et al., "Structures of APRIL-Receptor Complexes," Journal of Biological Chemistry, vol. 280, No. 8, pp. 7218-7227 (2005).
Ibragimova, G., et al., "Stability of the B-Sheet of the WW Domain: A Molecular Dynamics Simulation Study," Biophysical Journal, vol. 77, pp. 2192-2198 (1999).
Idemura, J. Mol Biol., vol. 158, pp. 573-597 (1982).
Imboden, J.B., et al., "The Antigen Receptor on a Human T Cell Line Initiates Activation by Increasing Cytoplasmic Free Calcium" Journal of Immunology, vol. 134, No. 2, pp. 663-665 (Feb. 1985).
Inbar, et al., Proc. Natl. Acad. Sci., vol. 69, p. 2659 (1972).
InNEXUS Lead Candidate DXL625Outpeforms Rituxan in Additional Animal Studies, [Online] Retrieved from Scientific Blogging, XP-002515036, (2008, pp. 1-2, Presentation American Association for Cancer Research, San Diego, CA, 2008, pp. 1-14.
Interlocutory Decision in Opposition Proceedings of EP 00902354 dated Nov. 30, 2007.
International Preliminary Report on Patentability of PCT/US98/04270 dated Jan. 5, 1999.
International Search Report for WO 99/12964 dated Apr. 13, 1999.
International Search Report of PCT/US00/00396 dated Jul. 7, 2000.
International Search Report of PCT/US2006/031274, dated Jun. 1, 2007 (0031.00PC01) WO 2007/019573.
International Search Report of PCT/US2006/031277, dated May 9, 2007 (0033.00PC01) (WO 2007/019575).
International Search Report of PCT/US2008/080177 dated Feb. 26, 2009.
Jones, et al., Nature, vol. 321, p. 522 (1986).

Kalled, S.L., et al., "BAFF; B Cell Survival Factor and Emerging Therapeutic Target for Autoimmune Disorders," Expert Opin. Ther. Targets, vol. 7, No. 1, pp. 115-123 (2003).
Karttunen, J., and N. Shastri, "Measurement of Ligand-induced Activation in Single Viable T Cells Using the lacZ Reporter Gene," Proc. Natl. Acad. Sci. USA, vol. 88, pp. 3972-3976 (May 1991).
Kelly, K., "APRIL/TRDL-1, a Tumor Necrosis Factor-Like Ligand, Stimulates Cell Death," Cancer Research, vol. 60, pp. 1021-1027 (2000).
Khare, et al., Proc. Natl. Acad. Sci. USA, vol. 97, pp. 3370-3375 (2000).
Kohler, et al., Nature, vol. 257, p. 495 (1975).
Kolb, et al., Insertion of a Foreign Gene into the Beta-casein Locus by Cre-mediated Site-specific Recombination, Gene, vol. 227, pp. 21-31 (1999).
Korganow, et al., Immunity, vol. 10, pp. 451-461 (1999).
Kyte, Doolittle, J. Mol. Biol., vol. 157, pp. 105-142 (1982).
Laabi, et al., "A New Gene, BCM, on Chromosome 16 is Fused to the Interleukin 2 Gene by a t(4;16) (q26;p13) Translocation in a Malignant T Cell Lymphoma," EMBO Journal, vol. 11, No. 11, pp. 3897-3904 (1992).
Laabi, et al., "The BCMA Gene, Preferentially Expressed During B Lymphoid Maturation, is Bidirectionally Transcribed," Nucleic Acids Research, vol. 22, No. 7, pp. 1147-1154 (1994).
Larrick, et al., Methods: A Companion to Methods in Enzymology, vol. 2, p. 106 (1991).
Lazar et al., "Transforming Growth Factor alpha: Mutation of Aspartic Acid 47 and Leucine 48 Results in Different Biological Activities" Molecular and Cellular Biology 8(3) 1247-1252 (1988).
Leiter, E.H. & Lee, C-H., "Is There Evidence for Genetic Overlap Between Type 1 and Type 2 Diabestes?" Diabetes, vol. 54, Supp. 2, pp. S151-S158 (2005).
Leiter, et al. "Mice with targeted gene disruptions or gene insertions for diabetes research; problems, pitfalls, and potential solutions," Diabetologia, vol. 45, pp. 296-308 (2002).
Liapakis, G., et al., "Identification of Ligand Binding Determinants in the Somatostatin Receptor Subtypes 2 and 2," Journal of Biological Chemnistry, vol. 271, No. 34, pp. 20331-20339 (1996).
Lin et al., "Structure-Function Relationships in Glucagon: Properties of Highly Purified Des-His1, Monoiodo-, and [Des-Asn 28,Thr29](homoserine lactone27)-glucagon" Biochemistry USA 14:1559-1563 (1975).
Lin, J.C., et al., "A Microdomain Formed by the Extracellular Ends of the Transmembrane Domains Promotes Activation of the G Protein-Coupled α-Factor Receptor," Molecular and Cellular Biology, vol. 24, No. 5, pp. 2041-2051 (2004).
Liu, J., et al., "Calcineurin is a Common Target of Cyclophilin-Cyclosporin A FKBP-FK506 Complexes," Cell, vol. 66, pp. 807-815 (Aug. 13, 1991).
Lonberg, et al., Nature, vol. 368, p. 856 (1994).
Losman, et al., Int. J. Cancer, vol. 46, p. 310 (1990).
Luckow, et al., J. Virol., vol. 67, pp. 4566-4579 (1993).
Mackay, F., et al., "Mice Transgenic for BAFF Develop Lymphocytic Disorders Along with Autoimmune Manifestations," J. Exp. Med., vol. 190, No. 11, pp. 1697-1710 (1999).
Madry, "The Characterization of Murine BCMA Gene Defines it as a New Member of the Tumor Necrosis Factor Receptor Superfamily," International Immunology, vol. 10, No. 11, pp. 1693-1702 (Aug 3, 1998).
Mariette, X., et al., "The Level of BLyS (BAFF) Correlates with the Titre of Autoantibodies in Human Sjogren's Syndrome," Annals of the Rheumatic Diseases, vol. 62, pp. 168-171 (2003).
Marsters, S., et al., "Interaction of the TNF Homologues BLyS and APRIL with the TNF Receptor Homologues BCMA and TACI," Current Biology, vol. 10, No. 13, pp. 785-788 (2000).
Martino, FierceBiotech, Press Release: ZymoGenetics and Serono to Begin TACI-Ig Clinical Studies in B-cell Malignancies, pp. 1-4, Nov. 9, 2006.
Mathey-Prevot, et al., Mol. Cell. Biol., vol. 6, pp. 4133-4135 (1986).
Moore, P., et al., "BLyS: Member of the Tumor Necrosis Factor Family and B Lymphocyte Stimulator," Science, vol. 285, pp. 260-263 (1999).

Mukhopadhyay, et al., "Identification and Characterization of a Novel Cytokine, THANK, a TNF Homologue That Activates Apoptosis, Nuclear Factor-kB, and c-Jun NH2-Terminal Kinase," Journal of Biological Chemistry, vol. 274, No. 23, pp. 15978-15981 (1999).
Moon and Ryu, "TACI: Fc Scavenging B Cell Activating Factor (BAFF) Alleviates Ovalbumin-Induced Bronchial Asthma in Mice," Exp. Mol. Med., vol. 39, No. 3, pp. 343-352 (Jun. 2007).
Munafo, et al., "Safety, Pharmacokinetics and Pharmacodynamics of Atacicept in Healthy Volunteers," Eur J Clin Pharmacol, vol. 63, pp. 647-656 (Apr. 2, 2007).
Neumann, et al., Embo J., vol. 1, pp. 841-845 (1982).
Ng, et al., "B Cell-Activating Factor Belonging to the TNF Family (BAFF)-R Is the Principal BAFF Receptor Facilitating BAFF Costimulation of Circulating T and B Cells," Journal of Immunology, vol. 173, pp. 807-817 (2004).
Nilsson, et al., Embo J., vol. 4, p. 1075, (1985).
Nilsson, et al., Methods Enzymol., vol. 198, p. 3 (1991).
Nisonoff, et al., Biochem. Biophys, vol. 89, p. 230 (1960).
Novake, Anne, J., et al., Blood, vol. 103, No. 2, pp. 689-694 (2004).
O'Keefe, S.J., et al., "FK-506 and CsA-sensitive Activation of the Interleukin-2 Promoter by Calcineurin," Nature, vol. 357, pp. 692-694 (Jun. 25, 1992).
Orlandi, et al., Proc. Natl. Acad. Sci., vol. 86, p. 3833 (1989).
Pack, et al., Bio/Technology, vol. 11, p. 1271 (1993).
Palacios, Steinemetz, Cell, vol. 41, pp. 727-734 (1985).
Panayi, "The Pathogenesis of Rheumatoid Arthritis: From Molecules to the Whole Patient," British Journal of Rheumatology, vol. 32, pp. 533-536 (1993).
Patel, et al., "Engineering an APRIL-specific B Cell Maturation Antigen," Journal of Biological Chemistry, vol. 279, No. 16, pp. 16727-16735 (Apr. 16, 2004).
Perez-Melgosa, et al., J. Immunol., vol. 163, p. 1123-27 (1999).
Porter, Biochem. J., vol. 73, p. 119 (1959).
Premack, B.A., et al., "Activation of $CA^{2+}$ Current in Jurkat T Cells Following the Depletion of $Ca^{2+}$ Stores by Microsomal $Ca^{2+}$-ATPase Inhibitors," Journal of Immunology, vol. 152, pp. 5226-5240 (1994).
Putney, J.W., Jr., and G.St. J. Bird, The Signal for Capactiative Calcium Entry, Cell, vol. 75, pp. 199-201 (Oct. 22, 1993).
Ramakrishnan and Scheid, "Diagnosis and Management of Acute Pyelonephritis in Adults," American Family Physician, vol. 71, No. 5, pp. 933-942 (Mar. 1, 2005).
Ramanujam, M. et al., "Mechanism of Action of Transmembrane Activator and Calcium Modulator Ligand Interactor-Ig in Murine Systemic Lupus erythematosus," J. Immunol., vol. 173, 3524-3534 (2004).
Raymond, et al., Yeast, vol. 14, pp. 11-23 (1998).
Richardson, P., et al., "A Phase 2 Study of Bortezomib in Relapsed, Refractoroy Myeloma," N Engl J Med, vol. 348, No. 26, pp. 2609-2617 (2003).
Roitt, I., et al., "Autoimmunity and Autoimmune Disease—27," Immunolgy, Fourth Edition, pp. 271-272 (1996).
Roschke, V., et al., "BLyS and APRIL Form Biologically Active Heterotrimers That Are Expressed in Patients with Systemic Immune-Based Rheumatic Diseases," Journal of Immunology, vol. 169, pp. 4314-4321 (2002).
Rudinger, J., "Characteristics of the Amino Acids as Components of Peptide Hormone Sequence," Peptide Hormones, University Park Press, Baltimore, pp. 1-7, (Jun. 1976).
Ryan, M., et al., "Antibody Targeting of B-Cell Maturaiton Antigen on Malignant Plasma Cells," Molecular Cancer Therapeutics, vol. 16, No. 11, US American Associate of Cancer Research pp. 3009-3018 (Nov. 2007).
Santee, S.M., and L.B. Owen-Schaub, "HumanTumor Necrosis Factor Receptor p75/80 (CD120B) Gene Structure and Promoter Characterization," The Journal of Biological Chemistry, vol. 271, No. 35, pp. 21151-21159 (1996).
Scatchard Ann. Ny. Acad. Sci., vol. 51, p. 660 (1949).
Schneider, P., et al., "BAFF, A Novel Ligand of the Tumor Necrosis Factor Family, Stimulates B Cell Growth," J. Exp. Med., vol. 189, No. 11, pp. 1747-1756 (1999).
Schwartz et al., "A Superactive Insulin: [B10-Aspartic acid] insulin (human)" Proc Natl Acad Sci USA 84:6408-6411 (1987).

Sethi, S., et al., "Oxidized Omega-3 Fatty Acids in Fish Oil Inhibit Leukocyte-Endothelial Interactions Through Activation of Pparg," Blood, vol. 100, No. 4, pp. 1340-1346 (2002).
Shu, et al., J. Leukoc Biol., vol. 65, pp. 680-683 (1999).
Sigmund, C., Jun. 2000, Arterioscler. Thromb. Vasc. Biol., p. 1425-1429.
Silverman, G.J., et al., "B Cell Modulation in Rheumatology," Current Opinion in Pharmacology—Cancer/Immunomodulation 200708 GB, vol. 7, No. 4, pp. 426-433 (Aug. 4, 2007).
Singer, et al., J. Immun., vol. 150, p. 2844 (1993).
Sinkar, et al., J. Biosci., vol. 11, pp. 47-58 (1987).
Sipos, L., et al., Eur. J. Biochem., vol. 213, pp. 1333-1340 (1993).
Smith, et al., "The TNF Receptor Superfamily of Cellular and Viral Proteins" Activation, Costimulation and Death vol. 76, pp. 959-962 (1994).
Smith, Johnson, Gene, vol. 67, p. 31 (1988).
Smith, T., et al., "The Challenges of Genome Sequence annotation or The devil is in the details," Nature Biotechnology, vol. 15, 1222-1223 (1997).
Stein, et al., "Immunologic Markers in the Differential Diagnosis of Non-Hodgkins Lymphomas," Journal of Cancer Research and Clinical Oncology, vol. 101, p. 29, Abstract (1981).
Stohl, et al., "B Cell Depletion Therapy in Systemic Rheumatic Diseases: Different Strokes for Different Folks?" Clinical Immunology, vol. 121, No. 1, pp. 1-12 (Oct. 1, 2006) (Abstract).
Strand V. et al., "Biologic Therapies in Rheumatology: Lessons Learned, Future Directions," Nat. Rev. Drug. Discov., vol. 6, No. 1, 75-92 (2007).
Stryer, L., "Flow of Genetic Information," Biochemistry Fourth Edicition, W.H. Freeman and Company, New York, pp. 111 (1996).
Stuve, O., et al., "Clinical Stabilization and Effective B-lymphocyte Depletion in the Cerebrospinal Fluid and Peripheral Blood of a Patient with Fulminant Relapsing-Remitting Multiple Sclerosis," Archives of Neurology, vol. 62, No. 10, pp. 1620-1623 (Oct. 2005).
Sulkowski, Trends in Biochem, vol. 1, p. 7 (1985).
Suntharalingam G., et al., "Cytokine Storm in a Phase 1 Trial of the Anti-CD28 Monoclonal Antibody TGN1412," N. Engl. J. Med., vol. 355, 1018-1028 (2006).
Takashi, et al., Japanese Journal of Science, vol. 28, No. 5, pp. 333-342, (Oct. 2005) Abstract.
Takebe, Y., et al., SrαPromoter: an Efficient and Versatile Mammalian cDNA Expression System Composed of the Simian Virus 40 Early Prometer and the R-US Segment of Human T-Cell Leukemia Virus Type 1 Long Terminal Repeat, Molecular and Cellular Biology, vol. 8, No. pp. 466-472 (Jun. 1988).
Tashiro, K., et al., "Signal Sequence Trap: A Cloning Strategy for Secreted Proteins and Type I Membrane Proteins," Science, vol. 261, pp. 600-603 (Jul. 30, 1993).
Taylor, et al., Int. Immun., vol. 6, p. 579 (1994).
Thompson, et al., "BAFF Binds to the Tumor Necrosis Factor Receptor-like Molecule B Cell Maturation Antigen and is Important for Maintaining the Peripheral B Cell Population," J. Exp. Med., vol. 192, No. 1, pp. 129-135 (Jul. 3, 2000).
Thompson, J., et al., "BAFF-R, a Newly Identified TNF Receptor That Specifically Interacts with BAFF," Science, vol. 293, pp. 2108-2111 (2001).
Truneh, A., et al., Early Steps of Lymphocyte Activation Bypassed by Synergy Between Calcium Ionophores and Phorbol Ester, Nature, vol. 313, pp. 318-320 (Jan. 24, 1985).
Tsokos, "Lymphocytes, Cytokines, Inflammation, and Immune Trafficking," Current Opinion in Rheumatology, vol. 7, pp. 376-383 (1995).
Tuan, et al., Connect Tiss. Res., vol. 34, pp. 1-9 (1996).
Varthakavi, Minocha, J. Gen. Virol., vol. 77, p. 1875 (1996).
Verweij, C.L., et al., "Cell Type Specificity and Activation Requirements for NFAT-1 (Nuclear Factor of Activated T-cells) Transcriptional Activity Determined by a New Method Using Transgenic Mice to Assay Transcriptional Activity of an Individual Nuclear Factor," Journal of Biological Chemistry, vol. 265, No. 26, pp. 15788-15795 (Sep. 15, 1990).
Von Bulow, G. U. and R.J. Bram, "NF-AT Activation Induced by a CAML-Interacting Member of the Tumor Necrosis Factor Receptor Superfamily," Science, vol. 278, pp. 138-141 (Oct. 3, 1997).

Von Bulow and R.J. Bram, "Activation of the Transcription Factor NFAT by a Novel CAML-Interacting Member of the Tumor Necrosis Factor Receptor Superfamily," Blood, vol. 90, No. 10, Suppl. 1, Part 1, pp. 246A-247 (1997).
Von Bulow, G.U., et al., "Molecular Cloning and Functional Characterization of Murine Transmembrane Activator and CAML Interactor (TACI) with Chromosomal Localization in Human and Mouse," Mammalian Genome, vol. 11, pp. 628-632 (2000).
Vugmeyster, Y., et al., "A Soluble BAFF Antagonist, BR3-Fc, Decreases Peripheral Blood B Cells and Lymphoid Tissue Marginal Zone and Follicular B Cells in Cynomolgus Monkeys," American Journal of Pathology 200602 US, vol. 168, No. 2, pp. 476-489 (Feb. 2, 2006).
Wada, A., et al., "Identification of Ligand Recognition Sites in Heat-Stable Enterotoxin Receptor, Membrane-Associated Guanylyl Cyclase C by Site-Directed Mutational Analysis," Infection and Immunity, vol. 64, No. 12, pp. 5144-5150 (1996).
Wain-Hobson, et al., Gene, vol. 13, pp. 355-364 (1981).
Wallach, "TNF Ligand and TNF/NGF Receptor Families," Dept of Biological Chemistry, Weizmann Institute of Science, pp. 377-411 (2000).
Wang, et al., "TACI-Ligand Interactions are required for T Cell Activation and Collagen-Induced Arthritis in Mice," Nature Immunology, vol. 2, No. 7, pp. 632-637 (2001).
Ware, Nature, vol. 404, pp. 949-950 (2000).
Weiss, A., and D.R. Littman, et al., "Signal Transduction by Lymphocyte Antigen Receptors," Cell, vol. 76, pp. 263-274 (Jan. 28, 1994).
Wigler, et al., Cell, vol. 14, p. 7 25 (1978).
Wilson-Rawls, J., et al., Virology, vol. 201, pp. 66-76 (1994).
Wu, Y., et al., Tumor Necrosis Factor (TNF) Receptor Superfamily Member TACI is a High Affinity Receptor for TNF Family Members APRIL and BLyS, The Journal of Biological Chemistry, vol. 275, No. 45, pp. 35478-35485 (2000).
Xia et al., "TACI is a TRAF-Interacting Receptor for TALL-1, a Tumor Necrosis Factor Family Member Involved in B Cell Regulation," J. Exp. Med., vol. 192, No. 1, pp. 137-143 (Jul. 3, 2000).
Yan M., et al., "Activation and Accumulation of B Cells in TACI-Deficient Mice," Nat. Immunol., vol. 2, 638-643 (2001).
Yan, et al., Nature Immunol., vol. 1, pp. 37-41 (2000).
Yang, M., et al., "B Cell Maturation Antigen, the Receptor for a Proliferation-Inducing Ligand and B Cell-Activating Factor of the TNF Family, Induces Antigen Presentation in B Cells," Journal of Immunology, vol. 175, US The Williams and Wilkins Co., Baltimore, pp. 2814-2824 (Sep. 2005).
Yu, G., et al., "April and TALL-I and Receptors BCMA and TACI: System for Regulating Humoral Immunity," Nature, vol. 1, No. 3, pp. 252-256 (2000).
Zhou, et al., Blood, vol. 98, No. 11:808a, Abstract 3361 (2001).
Zhu, J., et al., "Plasma Cells and IL-4 in Chronic Bronchitis and Chronic Obstructive Pulmonary Disease," American Journal of Respiratory and Critical Care Medicine, vol. 175, US American Lung Association, New York, NY vol. 175, pp. 1125-1133 (Jun. 2007).
Zweifach, A., and R.S. Lewis, "Mitogen-regulated $Ca^{2+}$ Current of T Lymphocytes is Activated by Depletion of Intracellular $Ca^{2+}$ Stores," Proc. Natl. Acad. Sci. USA, vol. 90, pp. 6295-6299 (Jul. 1993).
U.S. Appl. No. 11/501,999 Final Office Action dated Jun. 12, 2009.
U.S. Appl. No. 11/501,999 Final office action dated Jan. 7, 2009.
U.S. Appl. No. 11/501,999 Non-final office action dated May 30, 2008.
U.S. Appl. No. 11/501,999 Restriction requirement dated Feb. 13, 2008.
U.S. Appl. No. 11/502,134 Non-final office action dated Mar. 12, 2009.
U.S. Appl. No. 11/502,134 Advisory Action Communication dated Dec. 16, 2008.
U.S. Appl. No. 11/502,134 Final office action dated Jul. 2, 2008.
U.S. Appl. No. 11/502,134 Non-final office action dated Sep. 27, 2007.
U.S. Appl. No. 11/748,978 Final office action dated Jun. 12, 2009.
U.S. Appl. No. 11/748,978 Final office action dated Jan. 8, 2009.
U.S. Appl. No. 11/748,978 Non-final Office action dated May 30, 2008.

U.S. Appl. No. 11/748,978 Restriction requirement dated Feb. 13, 2008.
U.S. Appl. No. 09/479,856 Restriction Requirement dated Jul. 28, 2000.
U.S. Appl. No. 09/627,206 Restriction Requirement dated Sep. 7, 2001.
U.S. Appl. No. 09/627,206 Restriction Requirement dated Apr. 26, 2002.
U.S. Appl. No. 09/627,206 Non-final office action dated Aug. 8, 2002.
U.S. Appl. No. 09/627,206 Final Office Action dated Apr. 28, 2003.
U.S. Appl. No. 09/627,206 Advisory Action dated Mar. 3, 2004.
U.S. Appl. No. 09/627,206 Non-final Office action dated Aug. 6, 2004.
U.S. Appl. No. 09/627,206 Final Office action dated May 23, 2005.
U.S. Appl. No. 09/627,206 Non-final Office action dated Dec. 29, 2006.
U.S. Appl. No. 09/627,206 Non-final Office Action Dec. 7, 2007.
U.S. Appl. No. 09/627,206 Final Office Action dated Aug. 18, 2008.
U.S. Appl. No. 09/627,206 Non-final office action dated Feb. 11, 2009.
U.S. Appl. No. 11/200,992 Non-Final Office Action dated Mar. 21, 2008.
U.S. Appl. No. 11/200,992 Final Office Action dated Dec. 15, 2008.
U.S. Appl. No. 11/242,294 Non-Final office action dated Jun. 22, 2007.
U.S. Appl. No. 11/242,294 Final Office Action dated May 28, 2008.
U.S. Appl. No. 11/242,294 Notice of Allowance dated Oct. 24, 2008.
U.S. Appl. No. 12/057,133 Restriction Requirement dated Jul. 13, 2009.
U.S. Appl. No. 10/152,363 Restriction Requirement dated Oct. 31, 2003.
U.S. Appl. No. 10/152,363 Non-final office action dated Feb. 24, 2004.
U.S. Appl. No. 10/152,363 Final office action dated Apr. 1, 2005.
U.S. Appl. No. 09/569,245 Restriction Requirement dated Sep. 7, 2001.
U.S. Appl. No. 09/569,245 Restriction Requirement dated Apr. 10, 2002.
U.S. Appl. No. 09/569,245 Non-Final Office Action dated Aug. 8, 2002.
U.S. Appl. No. 09/569,245 Final Office Action dated Apr. 25, 2003.
U.S. Appl. No. 09/569,245 Advisory Action dated Mar. 9, 2004.
U.S. Appl. No. 09/569,245 Non-Final Office Action dated Aug. 6, 2004.
U.S. Appl. No. 09/569,245 Final office Action dated May 23, 2005.
U.S. Appl. No. 09/569,245 Non-Final Office Action dated Sep. 12, 2006.
U.S. Appl. No. 09/569,245 Non-Final Office Action dated Nov. 16, 2007.
U.S. Appl. No. 09/569,245 Final Office Ation dated Aug. 21, 2008.
U.S. Appl. No. 09/569,245 Non-Final Office Action dated Feb. 13, 2009.
U.S. Appl. No. 12/252,955 Restriction Requirement dated Sep. 4, 2009.
U.S. Appl. No. 12/359,801 Notice of Allowance dated Aug. 17, 2009.

* cited by examiner

```
TacI    ---------- ---------- ---------- ---------- MSGLGRSRRG
BR43X1  ---------- ---------- ---------- ---------- ----GRSRRG
BR43X2  ---------- ---------- ---------- ---------- MSGLGRSRRG
BCMA    ---------- ---------- ---------- ---------- ----------

TacI    GRSRVDQEER FPQGLWTGVA MRSCPEEQYW DPLL-GTCMS CKTICNHQSQ
BR43X1  GRSRVDQEER FPQGLWTGVA MRSCPEEQYW DPLL-GTCMS CKTICNHQSQ
BR43X2  GRSRVDQEER ---------- ---------- ---------- ----------
BCMA    ---------- ------MLQM AGQCSQNEYF DSLL-HACIP CQLRCSSNTP
                              <--- 1st cys repeat ----------

TacI    -RTCAAFCRS L-------SC RKEQGKFYDH LL-RD-CISC ASICGQHPKQ
BR43X1  -RTCAAFCRS L-------SC RKEQGKFYDH LL-RD-CISC ASICGQHPKQ
BR43X2  --------WS L-------SC RKEQGKFYDH LL-RD-CISC ASICGQHPKQ
BCMA    PLTCQRYCNA SVTNSVKGTN AILWTCLGLS LIISLAVFVL MFLLRKISSE
        ------->              <----- 2nd cys repeat ------------

TacI    CAYFCENKLR SPVNLPPELR RQRSGEVENN SDNSGRYQGL EHRGSEASPA
BR43X1  CAYFCENKLR SPVNLPPELR RQRSGEVENN SDNSGRYQGL EHRGSEASPA
BR43X2  CAYFCENKLR SPVNLPPELR RQRSGEVENN SDNSGRYQGL EHRGSEASPA
BCMA    PLKDEFKNTG SGLLGMANID LEKSRTGDEI ILPRGLEYTV EECTCEDCIK
        ---->

TacI    LPGLKLSADQ VALVYSTLGL CLCAVLCCFL VAVACFLKKR GDPCSCQPRS
BR43X1  LPGLKLSADQ VALVYSTLGL CLCAVLCCFL VAVACFLKKR GDPCSCQPRS
BR43X2  LPGLKLSADQ VALVYSTLGL CLCAVLCCFL VAVACFLKKR GDPCSCQPRS
BCMA    SKPKVDSDHC FPLPAMEEGA TILVTTKTND YCKSLPAALS ATEIEKSISA
                             <-- TACI/BR43 TM ---->

TacI    RPRQSPAKSS QDHAMEAGSP VSTSPEPVET CSFCFPECRA PTQESAVTPG
BR43X1  RPRQSPAKSS QDHAMEAGSP VSTSPEPVET CSFCFPECRA PTQESAVTPG
BR43X2  RPRQSPAKSS QDHAMEAGSP VSTSPEPVET CSFCFPECRA PTQESAVTPG
BCMA    R--------- ---------- ---------- ---------- ----------

TacI    TPDPTCAGRW GCHTRTTVLQ PCPHIPDSGL GIVCVPAQEG GPGA------
BR43X1  TPDPTCAGRW GCHTRTTVLQ PCPHIPDSGL GIVCVPAQEG GPGA------
BR43X2  TPDPTCAGRW GCHTRTTVLQ PCPHIPDSGL GIVCVPAQEG GPGA------
BCMA    ---------- ---------- ---------- ---------- ----------
```

FIGURE 1

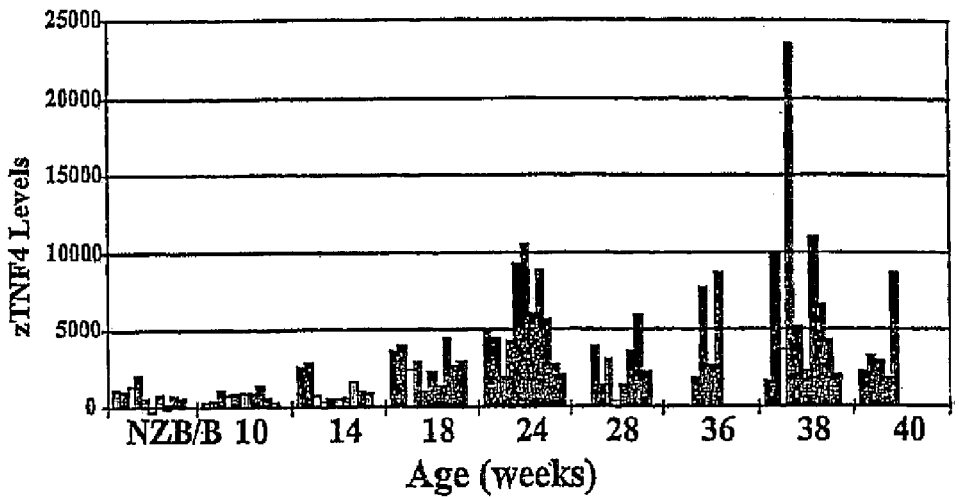
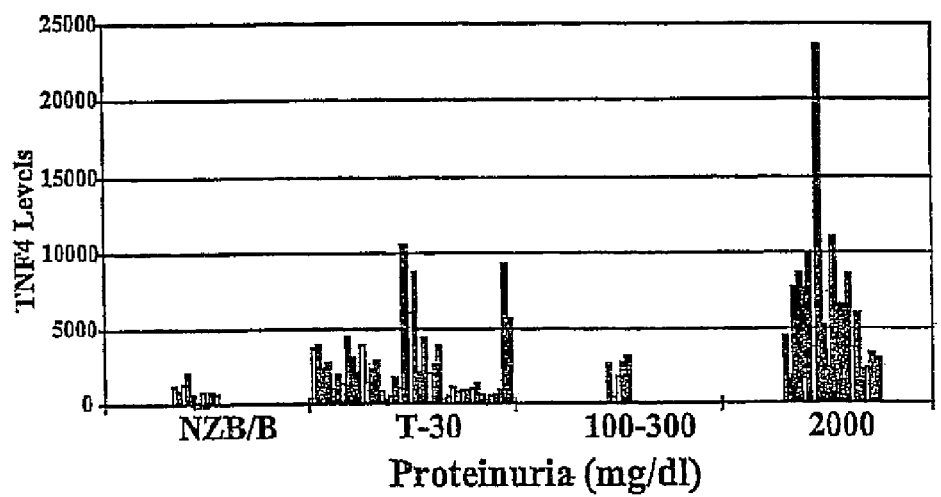
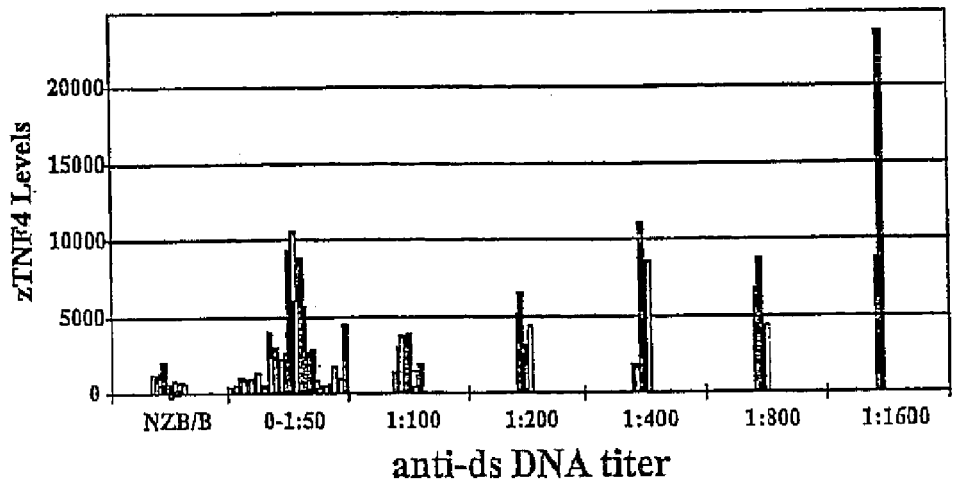
Figure 6A

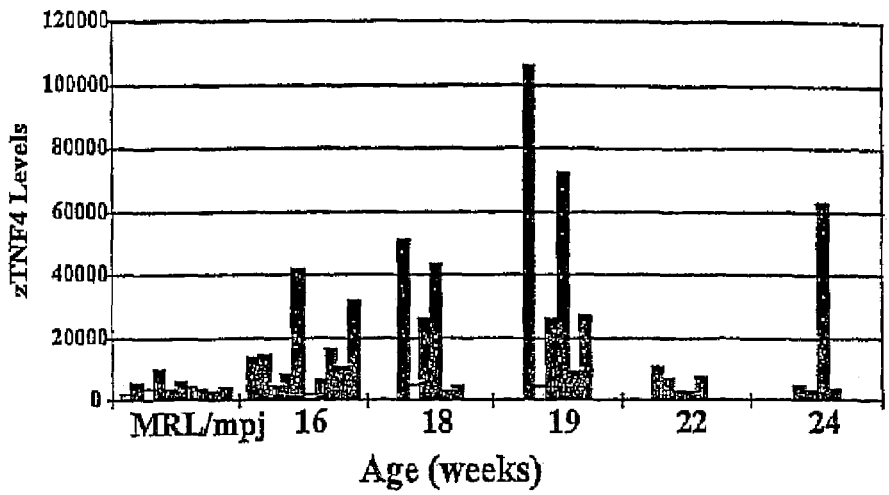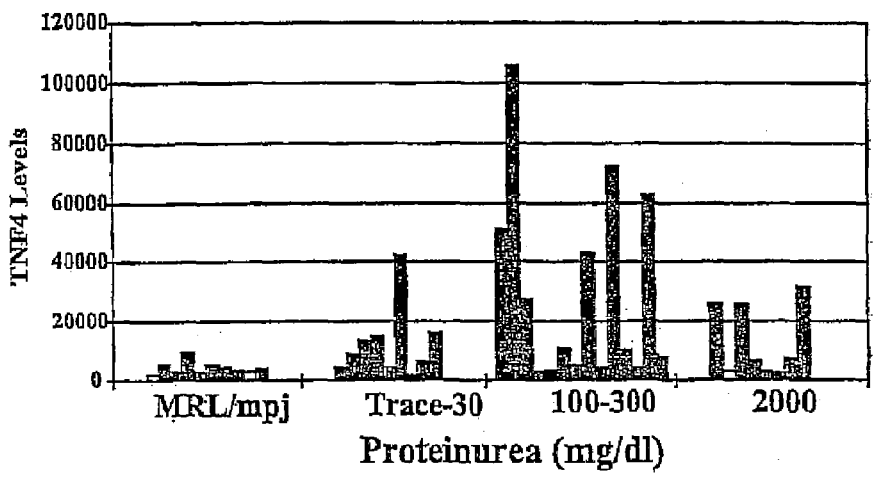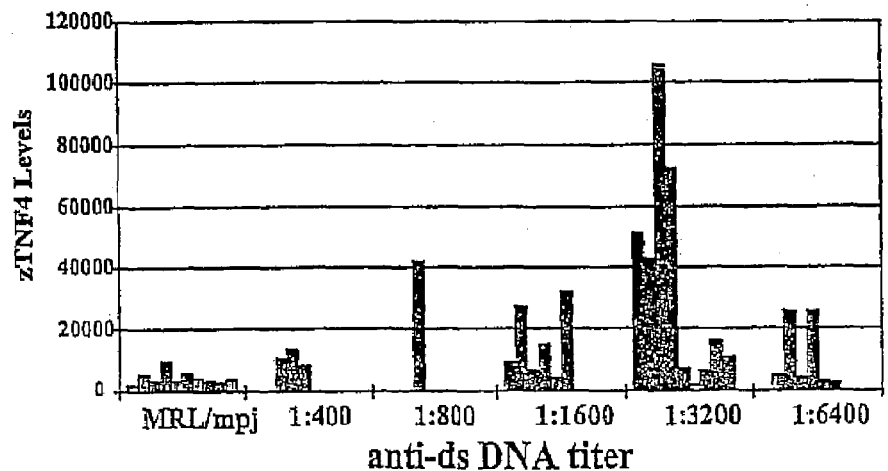
Figure 6B

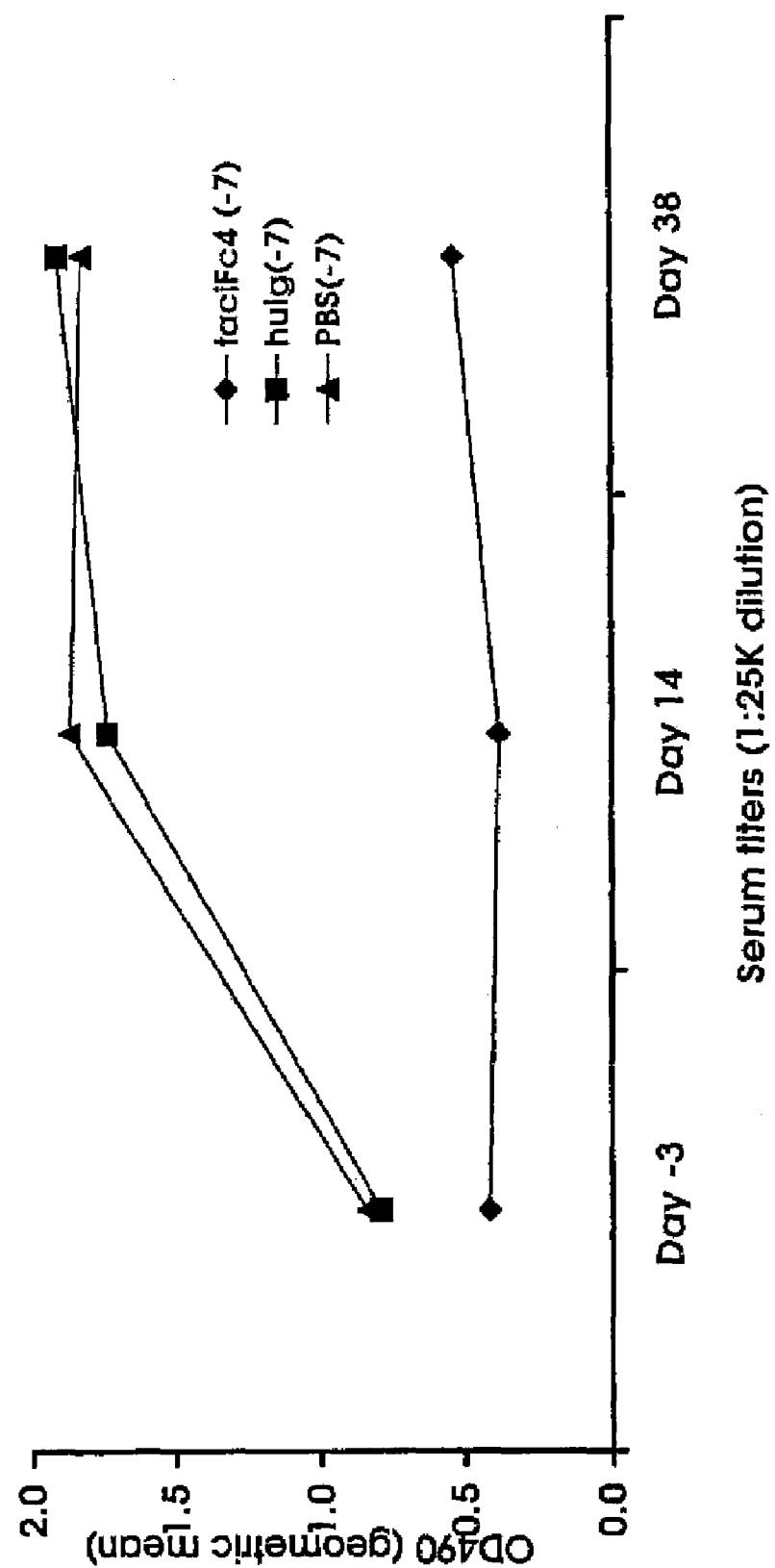

SOLUBLE RECEPTOR BR43X2

REFERENCE TO RELATED APPLICATIONS

This application is a divisional of U.S. patent application Ser. No. 09/627,206, filed Jul. 27, 2000, which is a continuation-in-part of U.S. patent application Ser. No. 09/569,245, filed May 11, 2000, which is a continuation-in-part of U.S. patent application Ser. No. 09/479,856, filed on Jan. 7, 2000 (now abandoned), which is related to Provisional Application 60/115,068, filed on Jan. 7, 1999 and 60/169,890, filed on Dec. 9, 1999. Under 35 U.S.C. § 119(e)(1), this application claims benefit of said Provisional Applications.

BACKGROUND OF THE INVENTION

Cellular interactions which occur during an immune response are regulated by members of several families of cell surface receptors, including the tumor necrosis factor receptor (TNFR) family. The TNFR family consists of a number of integral membrane glycoprotein receptors many of which, in conjunction with their respective ligands, regulate interactions between different hematopoietic cell lineages (Smith et al., *The TNF Receptor Superfamily of Cellular and Viral Proteins: Activation, Costimulation and Death*, 76:959-62, 1994; Cosman, *Stem Cells* 12:440-55, 1994).

One such receptor is TACI, transmembrane activator and CAML-interactor (von Bülow and Bram, *Science* 228:138-41, 1997 and WIPO Publication WO 98/39361). TACI is a membrane bound receptor having an extracellular domain containing two cysteine-rich pseudo-repeats, a transmembrane domain and a cytoplasmic domain that interacts with CAML (calcium-modulator and cyclophilin ligand), an integral membrane protein located at intracellular vesicles which is a co-inducer of NF-AT activation when overexpressed in Jurkat cells. TACI is associated with B cells and a subset of T cells. von Bülow and Bram (ibid.) report that the ligand for TACI is not known.

The polypeptides of the present invention, a TACI isoform having only one cysteine-rich pseudo-repeat (BR43x2), TACI and a related B cell protein, BCMA (Gras et al., *Int. Immunol.* 17:1093-106, 1995) were found to bind to the TNF ligand, ztnf4, now know as neutrokine α (WIPO Publication, WO 98/18921), BLyS (Moore et al., *Science*, 285:260-3, 1999), BAFF (Schneider et al., *J. Exp. Med.* 189:1747-56, 1999), TALL-1 (Shu et al., *J. Leukoc. Biol.* 65:680-3, 1999) or THANK (Mukhopadhyay et al., *J. Biol. Chem.* 274:15978-81, 1999). As such, BR43x2, TACI, and BCMA would be useful to regulate the activity of ztnf4 in particular, the activation of B cells.

Towards this end, the present invention provides protein therapeutics for modulating the activity of ztnf4 or other BR43x2, TACI or BCMA ligands, related compositions and methods as well as other uses that should be apparent to those skilled in the art from the teachings herein.

SUMMARY OF THE INVENTION

Within one aspect the invention provides a method of inhibiting ztnf4 activity in a mammal comprising administering to said mammal an amount of a compound selected from the group consisting of: a) a soluble ztnf4 receptor; b) a polypeptide comprising the extracellular domain of BR43x2; c) a polypeptide comprising the extracellular domain of TACI; d) a polypeptide comprising the extracellular domain of BCMA; e) a polypeptide comprising the sequence of SEQ ID NO:10; f) an antibody or antibody fragment which specifically binds to a polypeptide of SEQ ID NO:2; g) an antibody or antibody fragment which specifically binds to a polypeptide of SEQ ID NO:4; h) an antibody or antibody fragment which specifically binds to a polypeptide of SEQ ID NO:6; i) an antibody or antibody fragment which specifically binds to a polypeptide of SEQ ID NO:8; j) an antibody or antibody fragment which specifically binds to a polypeptide of SEQ ID NO: 10; k) a polypeptide of SEQ ID NO:4; l) amino acid residues 1-166 of SEQ ID NO:6; and m) amino acid residues 1-150 of SEQ ID NO:8. Within one embodiment the compound is a fusion protein consisting of a first portion and a second portion joined by a peptide bond, said first portion comprising a polypeptide selected from the group consisting of: a) a soluble ztnf4 receptor; b) a polypeptide comprising the sequence of SEQ ID NO: 10; c) a polypeptide comprising amino acid residues 25-58 of SEQ ID NO:2; d) a polypeptide comprising amino acid residues 34-66 of SEQ ID NO:6; e) a polypeptide comprising amino acid residues 71-104 of SEQ ID NO:6; f) a polypeptide comprising amino acid residues 25-104 of SEQ ID NO:6; g) a polypeptide comprising amino acid residues 8-37 of SEQ ID NO:8; h) a polypeptide comprising amino acid residues 41-88 of SEQ ID NO:8; i) a polypeptide comprising amino acid residues 8-88 of SEQ ID NO:8; and said second portion comprising another polypeptide. Within a related embodiment the first portion further comprises a polypeptide selected from the group consisting of: a) amino acid residues 59-120 of SEQ ID NO:2; b) amino acid residues 105-166 of SEQ ID NO:6; and c) amino acid residues 89-150 of SEQ ID NO:8. Within another embodiment the first portion is selected from the group consisting of: a) a polypeptide comprising the extracellular domain of BR43x2; b) a polypeptide comprising the extracellular domain of TACI; and c) a polypeptide comprising the extracellular domain of BCMA. Within another embodiment the first portion is selected from the group consisting of: a) a polypeptide of SEQ ID NO:4; b) amino acid residues 1-154 of SEQ ID NO:6; and c) amino acid residues 1-48 of SEQ ID NO:8. Within a further embodiment the second portion is an immunoglobulin heavy chain constant region.

Within another embodiment is a method wherein said antibody or antibody fragment is selected from the group consisting of: a) polyclonal antibody; b) murine monoclonal antibody; c) humanized antibody derived from b); and d) human monoclonal antibody. Within a related embodiment the antibody fragment is selected from the group consisting of F(ab'), F(ab), Fab', Fab, Fv, scFv, and minimal recognition unit.

Within yet another embodiment is a method wherein said mammal is a primate.

Within other embodiments is a method wherein said ztnf4 activity is associated with B lymphocytes, activated B lymphocytes, or resting B lymphocytes.

Within still another embodiment is a method wherein said ztnf4 activity is associated with antibody production. Within a related embodiment the antibody production is associated with an autoimmune disease. Within another related embodiment the autoimmune disease is systemic lupus erythomatosis, myasthenia gravis, multiple sclerosis, insulin dependent diabetes mellitus or rheumatoid arthritis.

Within another embodiment the ztnf4 activity is associated with asthma, bronchitis or emphysema.

Within other embodiments the ztnf4 activity is associated with end stage renal failure or renal disease. Within a related embodiment the renal disease is glomerulonephritis, vasculitis, chronic lymphoid leukemia, nephritis or pyelonephritis.

Within another embodiment ztnf4 activity is associated with renal neoplasms, multiple myelomas, lymphomas, light chain neuropathy or amyloidosis.

Another embodiment provides a method wherein the ztnf4 activity is associated with effector T cells. Within a related embodiment the ztnf4 activity is associated with regulating immune response. Within another embodiment the ztnf4 activity is associated with immunosuppression. Within yet another embodiment the immunosuppression is associated with graft rejection, graft verses host disease or inflammation. Within still another embodiment the immunosuppression is associated with autoimmune disease. Another embodiment provides that the autoimmune disease is insulin-dependent diabetes mellitus or Crohn's disease. Still another embodiment provides that the immunosuppression is associated with inflammation. Within a related embodiment the inflammation is associated with joint pain, swelling, anemia, or septic shock.

Within another aspect the invention provides a method for inhibiting BR43x2, TACI or BCMA receptor-ligand engagement comprising administering an amount of a compound selected from the group consisting of: a) a ztnf4 receptor, b) a polypeptide comprising the extracellular domain of BR43x2; c) a polypeptide comprising the extracellular domain of TACI; d) a polypeptide comprising the extracellular domain of BCMA; e) a polypeptide comprising the sequence of SEQ ID NO: 10; f) an antibody or antibody fragment which specifically binds to a polypeptide of SEQ ID NO:2; g) an antibody or antibody fragment which specifically binds to a polypeptide of SEQ ID NO:4; h) an antibody or antibody fragment which specifically binds to a polypeptide of SEQ ID NO:6; i) an antibody or antibody fragment which specifically binds to a polypeptide of SEQ ID NO:8; j) an antibody or antibody fragment which specifically binds to a polypeptide of SEQ ID NO: 10; k) an antibody or antibody fragment which specifically binds to a polypeptide of SEQ ID NO: 18; l) an antibody or antibody fragment which specifically binds to a polypeptide of SEQ ID NO:20; m) a polypeptide of SEQ ID NO:4; n) amino acid residues 1-166 of SEQ ID NO:6; and o) amino acid residues 1-150 of SEQ ID NO:8. Within one embodiment the compound is a fusion protein consisting of a first portion and a second portion joined by a peptide bond, said first portion comprising a polypeptide selected from the group consisting of: a) a polypeptide comprising the sequence of SEQ ID NO:8; b) a polypeptide comprising amino acid residues 25-58 of SEQ ID NO:2; c) a polypeptide comprising amino acid residues 34-66 of SEQ ID NO:6; d) a polypeptide comprising amino acid residues 71-104 of SEQ ID NO:6; e) a polypeptide comprising amino acid residues 25-104 of SEQ ID NO:6; f) a polypeptide comprising amino acid residues 8-37 of SEQ ID NO:8; g) a polypeptide comprising amino acid residues 41-88 of SEQ ID NO:8; h) a polypeptide comprising amino acid residues 8-88 of SEQ ID NO:8; and said second portion comprising another polypeptide. Within another embodiment the first portion further comprises a polypeptide selected from the group consisting of: a) amino acid residues 59-120 of SEQ ID NO:2; b) amino acid residues 105-166 of SEQ ID NO:6; and c) amino acid residues 89-150 of SEQ ID NO:8. Within yet another embodiment the first portion is selected from the group consisting of: a) a polypeptide comprising the extracellular domain of BR43x2; b) a polypeptide comprising the extracellular domain of TACI; and c) a polypeptide comprising the extracellular domain of BCMA. Within yet another embodiment the first portion is selected from the group consisting of: a) a polypeptide of SEQ ID NO:4; b) amino acid residues 1-154 of SEQ ID NO:6; and c) amino acid residues 1-48 of SEQ ID NO:8. Within a related embodiment the second portion is an immunoglobulin heavy chain constant region.

Within another embodiment the said antibody or antibody fragment is selected from the group consisting of: a) polyclonal antibody; b) murine monoclonal antibody; c) humanized antibody derived from b); and d) human monoclonal antibody. Within a related embodiment the antibody fragment is selected from the group consisting of F(ab'), F(ab), Fab', Fab, Fv, scFv, and minimal recognition unit.

Within other embodiment the BR43x2, TACI or BCMA receptor-ligand engagement is associated with B lymphocytes, activated B lymphocytes, or resting B lymphocytes.

Within other embodiment the BR43x2, TACI or BCMA receptor-ligand engagement is associated with antibody production. Within a related embodiment the antibody production is associated with an autoimmune disease. Within another embodiment the autoimmune disease is systemic lupus erythematosis, myasthenia gravis, insulin dependent diabetes mellitus, multiple sclerosis, or rheumatoid arthritis.

Within other embodiment the BR43x2, TACI or BCMA receptor-ligand engagement is associated with asthma, bronchitis or emphysema.

Within other embodiment the BR43x2, TACI or BCMA receptor-ligand engagement is associated with end stage renal failure.

Within other embodiment the BR43x2, TACI or BCMA receptor-ligand engagement is associated with renal disease. Within a related embodiment the renal disease is glomerulonephritis, vasculitis, nephritis, chronic lymphoid leukemia, or pyelonephritis.

Within other embodiment the BR43x2, TACI or BCMA receptor-ligand engagement is associated with renal neoplasms, multiple myelomas, lymphomas, light chain neuropathy or amyloidosis.

Within other embodiment the BR43x2, TACI or BCMA receptor-ligand engagement is associated with effector T cells. Within a related embodiment the BR43x2, TACI or BCMA receptor-ligand engagement is associated with regulation of immune response. Within another related embodiment the BR43x2, TACI or BCMA receptor-ligand engagement is associated with immunosuppression. Within another embodiment the immunosuppression is associated with graft rejection, graft verses host disease or inflammation. Within another embodiment the immunosuppression is associated with autoimmune disease. Within a related embodiment the autoimmune disease is insulin-dependent diabetes mellitus or Crohn's Disease.

Within other embodiment the BR43x2, TACI or BCMA receptor-ligand engagement is associated with inflammation. Within a related embodiment the inflammation is associated with joint pain, swelling, anemia, or septic shock.

The invention also provides an isolated polynucleotide molecule encoding a polypeptide of SEQ ID NO:2. Also provided is an isolated polynucleotide molecule of SEQ ID NO: 1.

The invention also provides an expression vector comprising the following operably linked elements: a transcription promoter; a polynucleotide molecule as described above; and a transcription terminator.

The invention further provides a cultured cell into which has been introduced an expression vector as described above, wherein said cultured cell expresses said polypeptide encoded by said polynucleotide segment.

Also provided is a method of producing a polypeptide comprising: culturing a cell into which has been introduced an expression vector as described above; whereby said cell expresses said polypeptide encoded by said polynucleotide molecule; and recovering said expressed polypeptide.

The invention provides an isolated polypeptide having the sequence of SEQ ID NO:2. In a related embodiment the polypeptide is in combination with a pharmaceutically acceptable vehicle.

Within another aspect the invention provides a method for regulating B lymphocytes in a recipient in need of such B lymphocyte regulation, comprising administering to said recipient a pharmaceutically effective amount of a soluble ztnf4 receptor in a pharmaceutically acceptable vehicle. Within a related embodiment the B lymphocyte regulation is selected from the group consisting of: a) inhibition of B lymphocyte proliferation; b) inhibition of B lymphocyte activation; c) inhibition of B lymphocyte homeostasis; and d) inhibition of B lymphocyte effector function. Within another embodiment the B lymphocyte regulation is modulation of autoantibody production. Within yet another embodiment the B lymphocyte regulation is the reduction of B lymphocytes in the periphery of said recipient. Within one related embodiment the B lymphocytes are pre-pro or immature B lymphocytes. Within another embodiment the B lymphocyte regulation is associated with an autoimmune disease. Within a related embodiment the autoimmune disease is systemic lupus erythematosis, myasthenia gravis, insulin dependent diabetes mellitus, multiple sclerosis, or rheumatoid arthritis.

Another embodiment provides a method wherein the B lymphocyte regulation is associated with asthma, bronchitis or emphysema.

Another embodiment provides a method wherein the B lymphocyte regulation is associated with end stage renal failure.

Another embodiment provides a method wherein the B lymphocyte regulation is associated with renal disease. In a related embodiment the renal disease is glomerulonephritis, vasculitis, nephritis, chronic lymphoid leukemia, or pyelonephritis.

In yet another embodiment is provided a method wherein the B lymphocyte regulation is associated with renal neoplasms, multiple myelomas, lymphomas, light chain neuropathy or amyloidosis.

Another embodiment provides a method wherein B lymphocyte regulation is associated with effector T cells. Within one embodiment the B lymphocyte regulation is associated with regulation of immune response. Within a related embodiment the B lymphocyte regulation is associated with immunosuppression. Within another related embodiment the immunosuppression is associated with graft rejection, graft verses host disease or inflammation.

Within another embodiment is provided a method wherein B lymphocyte regulation is associated with autoimmune disease. Within a related embodiment the autoimmune disease is insulin-dependent diabetes mellitus or Crohn's Disease.

Within another embodiment the B lymphocyte regulation is associated with inflammation.

Within in another aspect the invention provides a method for reducing proteinuria in a recipient in need of such reduction, comprising administering to said recipient a pharmaceutically effective amount of a soluble ztnf4 receptor in a pharmaceutically acceptable vehicle. Within one embodiment the proteinuria is stimulated by ztnf4. Within another embodiment the proteinuria is associated with an autoimmune disease. Within a related embodiment the autoimmune disease is systemic lupus erythomatosis, myasthenia gravis, or rheumatoid arthritis.

Within another embodiment is provided a method wherein said proteinuria is associated with end stage renal failure.

Yet another embodiment provides a method wherein the proteinuria is associated with renal disease. A related embodiment provides that the renal disease is glomerulonephritis, vasculitis, nephritis, chronic lymphoid leukemia, or pyelonephritis.

BRIEF DESCRIPTION OF THE DRAWING

FIG. 1 shows a multiple amino acid sequence alignment between BR43x2, TACI (von Bülow and Bram, ibid.) (SEQ ID NO:6), BCMA (Gras et al., ibid.) (SEQ ID NO:8) and BR43x1 (SEQ ID NO:9). The cysteine-rich pseudo repeats and transmembrane domain are noted.

FIGS. 6A and B show elevated ztnf4 levels in serum obtained from NZBWF1 mice and MRL/lpr/lpr mice that correlates with development of SLE.

FIGS. 9A and 9B show the results of a collagen ELISA on serum taken from DBA/1J mice in CIA model.

Figure 2:
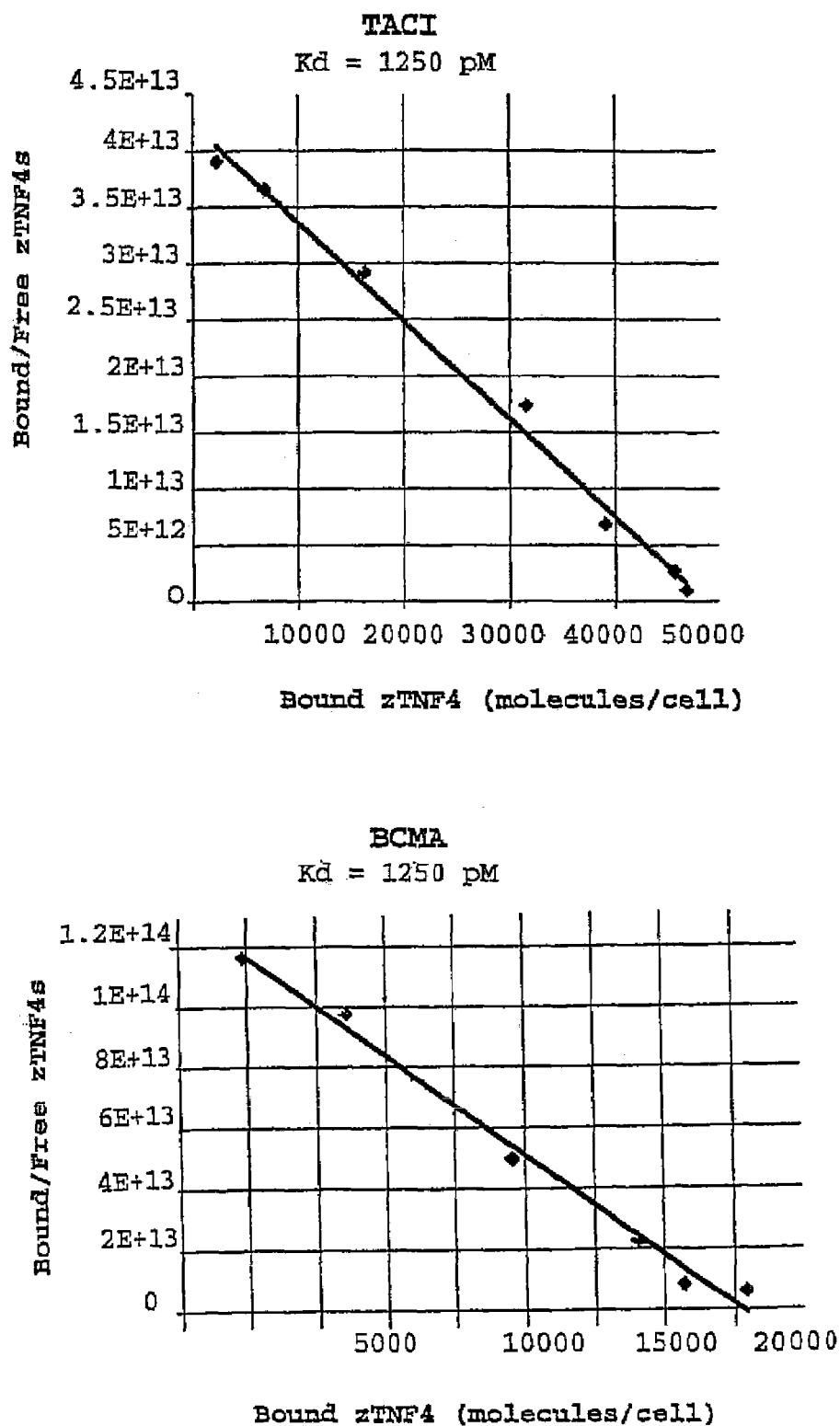
FIG. 2 shows a Scatchard plot analysis of soluble $I^{125}$-ztnf4 binding to TACI and BCMA expressed by stable BHK transfectants.

These and other aspects of the invention will become evident upon reference to the following detailed description.

DETAILED DESCRIPTION OF THE INVENTION

Prior to setting forth the invention, it may be helpful to an understanding thereof to set forth definitions of certain terms to be used hereinafter:

Affinity tag: is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

Allelic variant: Any of two or more alternative forms of a gene occupying the same chromosomal locus. Allelic variation arises naturally through mutation, and may result in phenotypic polymorphism within populations. Gene mutations can be silent (i.e., no change in the encoded polypeptide), or may encode polypeptides having altered amino acid sequence. The term "allelic variant" is also used herein to denote a protein encoded by an allelic variant of a gene. Also included are the same protein from the same species which differs from a reference amino acid sequence due to allelic variation. Allelic variation refers to naturally occurring differences among individuals in genes encoding a given protein.

Amino-terminal and carboxyl-terminal: are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

Complement/anti-complement pair: Denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^{-9}$ M.

Contig: Denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

Complements of polynucleotide molecules: Denotes polynucleotide molecules having a complementary base sequence and reverse orientation as compared to a reference sequence. For example, the sequence 5' ATGCACGGG 3' is complementary to 5'CCCGTGCAT 3'.

Degenerate Nucleotide Sequence or Degenerate Sequence: Denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

Expression vector: A DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Isoform: Refers to different forms of a protein that may be produced from different genes or from the same gene by alternate splicing. In some cases, isoforms differ in their transport activity, time of expression in development, tissue distribution, location in the cell or a combination of these properties.

Isolated polynucleotide: Denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

Isolated polypeptide or protein: Is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

Operably linked: As applied to nucleotide segments, the term "operably linked" indicates that the segments are arranged so that they function in concert for their intended purposes, e.g., transcription initiates in the promoter and proceeds through the coding segment to the terminator.

Ortholog: Denotes a polypeptide or protein obtained from one species that is the functional counterpart of a polypeptide or protein from a different species. Sequence differences among orthologs are the result of speciation.

Polynucleotide: Denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

Polypeptide: Is a polymer of amino acid residues joined by peptide bonds, whether produced naturally or synthetically. Polypeptides of less than about 10 amino acid residues are commonly referred to as "peptides".

Promoter: Denotes a portion of a gene containing DNA sequences that provide for the binding of RNA polymerase and initiation of transcription. Promoter sequences are commonly, but not always, found in the 5' non-coding regions of genes.

Protein: Is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

Receptor: A cell-associated protein, or a polypeptide subunit of such protein, that binds to a bioactive molecule (the "ligand") and mediates the effect of the ligand on the cell. Binding of ligand to receptor results in a change in the receptor (and, in some cases, receptor multimerization, i.e., association of identical or different receptor subunits) that causes interactions between the effector domain(s) of the receptor and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. BR43x2 has characteristics of TNF receptors, as discussed in more detail herein.

Secretory signal sequence: A DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

Soluble receptor: A receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a 1192 bp DNA sequence (SEQ ID NO: 1) and corresponding polypeptide sequence (SEQ ID NO:2) which is an isoform of the receptor TACI. The isoform has been designated BR43x2. A soluble form of BR43x2 is disclosed in SEQ ID NO:4, the polynucleotide encoding the soluble receptor in SEQ ID NO:3. As is described in more detail herein, the BR43x2 receptor-encoding polynucleotides and polypeptides of the present invention were initially identified by signal trap cloning using a human RPMI 1788 library and the N- or C-terminally FLAG-tagged, biotin- or FITC-labeled tumor necrosis factor ligand ztnf4, now known as neutrokine α (WIPO WO98/18921), BLyS (Moore et al., ibid.), BAFF (Schneider et al., ibid.), TALL-1 (Shu et al., ibid.) or THANK (Mukhopadhyay et al., ibid.). Positive pools were identified by ligand binding, broken down to single clones, the cDNA isolated and sequenced. A comparison of the BR43x2 deduced amino acid sequence (as represented in SEQ ID NO:2) with known tumor necrosis factor receptors indicated that BR43x2 is an isoform of TACI, having a single, poorly conserved, cysteine-rich pseudo-repeat.

Structurally, the TNF receptor family is characterized by an extracellular portion composed of several modules called, historically, "cysteine-rich pseudo-repeats". A prototypical TNFR family member has four of these pseudo-repeats, each about 29-43 residues long, one right after the other. A typical pseudo-repeat has 6 cysteine residues. They are called pseudo-repeats because, although they appear to originate from a common ancestral module, they do not repeat exactly: pseudo-repeats #1, #2, #3 and #4 have characteristic sequence features which distinguish them from one another. The crystal structure of the p55 TNF receptor revealed that each pseudo-repeat corresponds to one folding domain, and that all four pseudo-repeats fold into the same tertiary structure, held together internally by disulfide bonds.

TACI contains two cysteine-rich pseudo-repeats (von Bülow and Bram, ibid.), the first is conserved in structure with other members of the TNF receptor family, the second is less conserved. The BR43x2 isoform of the present invention lacks the first TACI cysteine-rich pseudo-repeat, retaining only the second, less conserved repeat. Sequence analysis of a deduced amino acid sequence of BR43x2 as represented in SEQ ID NO:2 indicates the presence of a mature protein having an extracellular domain (residues 1-120 of SEQ ID NO:2) which contains one cysteine-rich pseudo-repeat (residues 25-58 of SEQ ID NO:2), a transmembrane domain (residues 121-133 of SEQ ID NO:2) and a cytoplasmic domain (residues 134-247 of SEQ ID NO:2). The cysteine-rich pseudo-repeat of BR43x2 has 6 conserved cysteine residues (residues 25, 40, 43, 47, 54 and 58 of SEQ ID NO:2), a conserved aspartic acid residue (residue 34 of SEQ ID NO:2) and two conserved leucine residues (residues 36 and 37 of SEQ ID NO:2) and shares 46% identity with the first cysteine-rich pseudo-repeat of TACI (SEQ ID NO:6) and 35% identity with the cysteine-rich pseudo-repeat of BCMA (SEQ ID NO:8) (FIG. 1). The cysteine-rich pseudo-repeat can be represented by the following motif: CX[QEK][QEKNRDHS] [QE]X{0-2}[YFW][YFW]DXLLX{2}C[IMLV] XCX{3}CX{6-8}CX{2}[YF]C (SEQ ID NO:10), wherein C represents the amino acid residue cysteine, Q glutamine, E glutamic acid, K lysine, N asparagine, R arginine, D aspartic acid, H histidine, S serine, Y tyrosine, F phenylalanine, W tryptophan, L leucine, I isoleucine, V valine and X represents any naturally occurring amino acid residue except cysteine. Amino acid residues in square brackets "[ ]" indicate the allowed amino acid residue variation at that position. The number in the braces "{ }" indicates the number of allowed amino acid residues at that position.

The present invention also provides soluble polypeptides of from 32 to 40 amino acid residues in length as provided by SEQ ID NO: 10.

The soluble BR43x2 receptor, as represented by residues 1-120 of SEQ ID NO:4, contains one cysteine-rich pseudo-repeat (residues 25-58 of SEQ ID NO:4) and lacks the transmembrane and cytoplasmic domains of BR43x2 as described in SEQ ID NO:2.

Those skilled in the art will recognize that these domain boundaries are approximate, and are based on alignments with known proteins and predictions of protein folding. These features indicate that the receptor encoded by the DNA sequences of SEQ ID NOs: 1 and 3 is a member of the TNF receptor family.

Northern blot and Dot blot analysis of the tissue distribution of the mRNA corresponding to nucleotide probes to BR43x1 which are predicted to detect BR43x2 expression showed expression in spleen, lymph node, CD19+ cells, weakly in mixed lymphocyte reaction cells, Daudi and Raji cells. Using reverse transcriptase PCR BR43x1 was detected in B cells only and not in activated T cells as had been reported for TACI (von Bülow and Bram, ibid.). Using a BR43x2 probe that overlaps 100% with the corresponding TACI sequence, TACI and BR43x2 were detected in spleen, lymph node and small intestine, stomach, salivary gland, appendix, lung, bone marrow, fetal spleen, CD 19+ cells, and Raji cells.

Using Northern Blot analysis BCMA was detected in small intestine, spleen, stomach, colon, appendix, lymph node, trachea, and testis. BCMA was also detected in adenolymphoma, non-Hodgkins lymphoma, and parotid tumor, detected faintly in CD 8+, CD 19+, MLR cells, Daudi, Raji and Hut 78 cells.

Northern blot analysis was also done using murine ztnf4 (SEQ ID NO:19) and like human TACI, BCMA, and BR43x2, murine ztnf4 expression was detected predominately in spleen and thymus. Murine ztnf4 was also expressed in lung and faint expression was detected in skin and heart.

Additional blot analysis is described in the Examples herein.

The present invention also provides polynucleotide molecules, including DNA and RNA molecules, that encode the BR43x2 polypeptides disclosed herein. Those skilled in the art will readily recognize that, in view of the degeneracy of the genetic code, considerable sequence variation is possible among these polynucleotide molecules. SEQ ID NO: 11 is a degenerate DNA sequence that encompasses all DNAs that encode the soluble BR43x2 polypeptide of SEQ ID NO:4. Similarly, SEQ ID NO:12 is a degenerate DNA sequence that encompasses all DNAs that encode the BR43x2 polypeptide of SEQ ID NO:2. Those skilled in the art will recognize that the degenerate sequence of SEQ ID NO: 12 also provides all RNA sequences encoding SEQ ID NO:4 by substituting U for T. Thus, BR43x2 polypeptide-encoding polynucleotides comprising nucleotide 1 to nucleotide 360 of SEQ ID NO: 1, nucleotide 1 to 741 of SEQ ID NO:12 and their RNA equivalents are contemplated by the present invention. Table 1 sets forth the one-letter codes used within SEQ ID NOs: 11 and 12 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs: 11 and 12, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid seqeunces of SEQ ID NOs:2 and 4. Variant sequences can be readily tested for functionality as described herein.

One of ordinary skill in the art will also appreciate that different species can exhibit "preferential codon usage." In general, see, Grantham, et al., Nuc. Acids Res. 8:1893-912, 1980; Haas, et al. Curr. Biol. 6:315-24, 1996; Wain-Hobson, et al., Gene 13:355-64, 1981; Grosjean and Fiers, Gene 18:199-209, 1982; Holm, Nuc. Acids Res. 14:3075-87, 1986; Ikemura, J. Mol. Biol. 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:11 and 12 serve as a template for optimizing expression of polynucleotides in various cell types and species commonly used in the art and disclosed herein. Sequences containing preferential codons can be tested and optimized for expression in various species, and tested for functionality as disclosed herein.

The highly conserved amino acids in the cysteine-rich pseudo-repeat of BR43x2 can be used as a tool to identify new family members. For instance, reverse transcription-polymerase chain reaction (RT-PCR) can be used to amplify sequences encoding the extracellular ligand-binding domain, described above, from RNA obtained from a variety of tissue sources or cell lines. In particular, highly degenerate primers designed from the BR43x2 sequences are useful for this purpose.

Within preferred embodiments of the invention, isolated polynucleotides will hybridize to similar sized regions of SEQ ID NO:3, or to a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for isolating DNA and RNA are well known in the art. It is generally preferred to isolate RNA from RPMI 1788 cells, PBMNCs, resting or activated transfected B cells or tonsil tissue, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. Polynucleotides encoding BR43x2 polypeptides are then identified and isolated by, for example, hybridization or PCR.

Those skilled in the art will recognize that the sequences disclosed in SEQ ID NOs: 1 and 3 represent a single allele of the human gene, and that allelic variation and alternative splicing is expected to occur. Allelic variants of the DNA sequences shown in SEQ ID NOs: 1 and 3, including those containing silent mutations and those in which mutations result in amino acid sequence changes, are within the scope of the present invention, as are proteins which are allelic variants of SEQ ID NOs:2 and 4. Allelic variants and splice variants of these sequences can be cloned by probing cDNA or genomic libraries from different individuals or tissues according to standard procedures known in the art.

The present invention also provides isolated BR43x2 polypeptides that are substantially homologous to the polypeptides of SEQ ID NOs:2 and 4 and their species orthologs. The term "substantially homologous" is used herein to denote polypeptides having 50%, preferably 60%, more preferably at least 80%, sequence identity to the sequences shown in SEQ ID NOs:2 and 4 or their orthologs. Such polypeptides will more preferably be at least 90% identical, and most preferably 95% or more identical to SEQ ID NO:2 or its orthologs. Percent sequence identity is determined by conventional methods. See, for example, Altschul et al., *Bull. Math. Bio.* 48: 603-66, 1986 and Henikoff and Henikoff, *Proc. Natl. Acad. Sci. USA* 89:10915-9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |

TABLE 3-continued

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20-25 residues, or an affinity tag. Polypeptides comprising affinity tags can further comprise a proteolytic cleavage site between the BR43x2 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of BR43x2 polypeptides of the present invention. A limited number of non-conservative amino acids, amino acids that are not encoded by the genetic code, and unnatural amino acids may be substituted for BR43x2 polypeptide amino acid residues. The proteins of the present invention can also comprise non-naturally occurring amino acid residues.

Non-naturally occurring amino acids include, without limitation, trans-3-methylproline, 2,4-methanopro line, cis-4-hydroxypro line, trans-4-hydroxy-pro line, N-methylglycine, allo-threonine, methylthreonine, hydroxy-ethylcysteine, hydroxyethyl-homocysteine, nitro-glutamine, homoglutamine, pipecolic acid, tert-leucine, norvaline, 2-azaphenylalanine, 3-aza-phenylalanine, 4-azaphenylalanine, and 4-fluoro-phenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an $E.\ coli$ S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluoro-phenylalanine). The non-naturally occurring amino acid is incorporated into the protein in place of its natural counterpart. See, Koide et al., *Biochem.* 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for BR43x2 amino acid residues.

Essential amino acids in the BR43x2 polypeptides of the present invention can be identified according to procedures known in the art, such as site-directed mutagenesis or alanine-scanning mutagenesis (Cunningham and Wells, *Science* 244: 1081-5, 1989). Single alanine mutations are introduced at every residue in the molecule, and the resultant mutant molecules are tested for biological activity (e.g., providing a decrease in B cell response during the immune response, inhibition or decrease in autoantibody production) to identify amino acid residues that are critical to the activity of the molecule. See also, Hilton et al., *J. Biol. Chem.* 271:4699-708, 1996. Sites of biological interaction, ligand binding portions such as the cysteine-rich pseudo-repeats, can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-12, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related TNFR family members such as TACI and BCMA.

Additional amino acid substitutions can be made within the cysteine-rich pseudo-repeat of BR43x2 so long as the conserved cysteine, aspartic acid and leucine residues are retained and the higher order structure is not disturbed. It is preferred to make substitutions within the cysteine-rich pseudo-repeat of BR43x2 by reference to the sequences of other cysteine-rich pseudo-repeats. SEQ ID NO: 10 is a generalized cysteine-rich pseudo-repeat that shows allowable amino acid substitutions based on such an alignment. Substitutions with in this domain are subject to the limitations set forth herein.

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed BR43x2 DNA and polypeptide sequences can be generated through DNA shuffling as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., providing a decrease in B cell response during the immune response, inhibition or decrease in autoantibody production) can be recovered from the host cells and rapidly sequenced using modem equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 1 to 120 of SEQ ID NO:2 or allelic variants thereof and retain the B cell suppression properties of the wild-type protein. Such polypeptides may include additional amino acids or domains from other members of the tumor necrosis factor receptor superfamily, affinity tags or the like. BR43x2 polypeptide or fusion constructs, containing functional domains of other members of the TNFR superfamily, constitute hybrid tumor necrosis factor receptors exhibiting modified B cell suppression capabilities.

The present invention further provides counterpart receptors and polynucleotides from other species (orthologs). These species include, but are not limited to mammalian, avian, amphibian, reptile, fish, insect and other vertebrate and invertebrate species. Of particular interest are BR43x2 receptors from other mammalian species, including murine, porcine, ovine, bovine, canine, feline, equine, and other primate receptors. Orthologs of the human BR43x2 receptor can be cloned using information and compositions provided by the present invention in combination with conventional cloning techniques. For example, a cDNA can be cloned using mRNA obtained from a tissue or cell type that expresses the receptor. Suitable sources of mRNA can be identified by probing Northern blots with probes designed from the sequences disclosed herein. A library is then prepared from mRNA of a positive tissue or cell line. A receptor-encoding cDNA can then be isolated by a variety of methods, such as by probing with a complete or partial human cDNA or with one or more sets of degenerate probes based on the disclosed sequence. A cDNA can also be cloned using PCR, using primers designed from the sequences disclosed herein. Within an additional method, the cDNA library can be used to transform or transfect host cells, and expression of the cDNA of interest can be detected with an antibody to the receptor. Similar techniques can also be applied to the isolation of genomic clones.

The receptor polypeptides of the present invention, including full-length receptor polypeptides, soluble receptors polypeptides, polypeptide fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual, Second Edition*, Cold Spring Harbor, N.Y., 1989; and Ausubel et al., eds., *Current Protocols in Molecular Biology*, John Wiley and Sons, Inc., NY, 1987.

In general, a DNA sequence encoding a BR43x2 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a BR43x2 polypeptide into the secretory pathway of a host cell, a secretory signal sequence (also known as a signal sequence, leader sequence, prepro sequence or pre sequence) is provided in the expression vector. The secretory signal sequence may be that of the BR43x2 polypeptide, or may be derived from another secreted protein (e.g., t-PA) or synthesized de novo. The secretory signal sequence is joined to the BR43x2 DNA sequence in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation Neumann et al., *EMBO J.* 1:841-45, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al, U.S. Pat. No. 4,579,821; and Ringold, U.S. Pat. No. 4,656, 134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977), Jurkat (ATCC No. CRL-8129), BaF3 (an interleukin-3 dependent pre-lymphoid cell line derived from murine bone marrow. See, Palacios and Steinmetz, *Cell* 41: 727-34, 1985; Mathey-Prevot et al., *Mol. Cell. Biol.* 6: 4133-5, 1986) and Chinese hamster ovary (e.g., CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978 and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica nuclear polyhedrosis virus* (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and Richardson, Ed., *Baculovirus Expression Protocols. Methods in Molecular Biology*, Totowa, N.J., Humana Press, 1995. A second method of making recombinant BR43x2 baculovirus utilizes a transposon-based system described by Luckow (Luckow, et al., *J. Virol.* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the BR43x2 polypeptide into a baculovirus genome maintained in *E. coli* as a large plasmid called a "bacmid." See, Hill-Perkins and Possee, *J. Gen. Virol.* 71:971-6, 1990; Bonning, et al., *J. Gen. Virol.* 75:1551-6, 1994; and, Chazenbalk, and Rapoport, *J. Biol. Chem.* 270: 1543-9, 1995. In addition, transfer vectors can include an in-frame fusion with DNA encoding an epitope tag at the C- or N-terminus of the expressed BR43x2 polypeptide, for example, a Glu-Glu epitope tag (Grussenmeyer et al., *Proc. Natl. Acad. Sci.* 82:7952-4, 1985). Using a technique known in the art, a transfer vector containing BR43x2 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses BR43x2 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. Procedures used are generally described in available laboratory manuals (King and Possee, ibid.; O'Reilly, et al., ibid.; Richardson, ibid.). Subsequent purification of the BR43x2 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides there from are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092)

and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23, 1998, and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a BR43x2 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Expressed recombinant BR43x2 polypeptides (or chimeric or fusion BR43x2 polypeptides) can be purified using fractionation and/or conventional purification methods and media. It is preferred to provide the proteins or polypeptides of the present invention in a highly purified form, i.e. greater than 95% pure, more preferably greater than 99% pure. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their physical properties. For example, immobilized metal ion adsorption (IMAC) chromatography can be used to purify histidine-rich proteins including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, FLAG-tag (Asp Tyr Lys Asp Asp Asp Asp Lys (SEQ ID NO:13)), Glu-Glu tag (Glu Glu Tyr Met Pro Met Glu (SEQ ID NO:14)), an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

BR43x2 polypeptides or fragments thereof may also be prepared through chemical synthesis. BR43x2 polypeptides may be monomers or multimers; glycosylated or non-glycosylated; pegylated or non-pegylated; and may or may not include an initial methionine amino acid residue. Exemplary BR43x2 polypeptides include polypeptides of from 32-40 residues in length having an amino acid sequence conforming to the motif: XXCX[QEK][QEKNRDHS][QE]X{0-2}[YFW][YFW]DXLLX{2}C[IMLV]XCX{3}CX{6-8}CX{2}[YF]CXX (SEQ ID NO: 10), and subject to the limitations described herein.

BR43x2 polypeptides can be synthesized by exclusive solid phase synthesis, partial solid phase methods, fragment condensation or classical solution synthesis. The polypeptides are preferably prepared by solid phase peptide synthesis, for example as described by Merrifield, *J. Am. Chem. Soc.* 85:2149, 1963. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxycarbonyl (Fmoc)], aliphatic urethane protecting groups [e.g., t-butyloxycarbonyl (tBoc), isopropyl-oxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-penta-methyldihydrobenzofuran-5-sulfonyl (Pbf) for arginine, trityl for asparagine, cysteine, glutamine and histidine, tert-butyl for aspartic acid, glutamic acid, serine, threonine and tyrosine, tBoc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropyl-phosphoramidite and then oxidized by tert-butylhydro-peroxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlorotrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co., Rockford, Ill., 1984) and Bayer and Rapp, *Chem. Pept. Prot.* 3:3, 1986; and Atherton et al., Solid Phase Peptide Synthesis: *A Practical Approach*, IRL Press, Oxford, 1989.

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300-320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethyl-amino)-phosphonium hexafluoro-phosphate (BOP) and its pyrrolidine analog (PyBOP), bromo-tris-pyrrolidino-phosphonium hexafluorophosphate (PyBrOP), O-(benzotriazol-1-yl)-11,3,3-tetramethyluronium hexafluorophosphate (HBTU) and its tetra-fluoroborate analog (TBTU) or its pyrrolidine analog (HBPyU), O-(7-azabenzotriazol-1-yl)-1,1,3,3-tetramethyl-uronium hexafluoro-phosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine(HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction can be monitored at each stage, e.g., by the ninhydrin reaction as described by Kaiser et al., *Anal. Biochem.* 34:595, 1970.

After the entire assembly of the desired peptide, the peptide-resin is cleaved with a reagent with proper scavengers. The Fmoc peptides are usually cleaved and deprotected by TFA with scavengers (e.g., $H_2O$, ethanedithiol, phenol and thioanisole). The tBoc peptides are usually cleaved and deprotected with liquid HF for 1-2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury(II)acetate and alternatively by iodine, thallium(III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyl-trifluoroacetate (TMSOTf).

The present invention further provides a variety of other polypeptide fusions and related multimeric proteins comprising one or more polypeptide fusions. A soluble BR43x2, TACI or BCMA polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in close proximity to each other. Immunoglobulin-BR43x2 (TACI or BCMA) polypeptide fusions can be expressed in genetically engineered cells to produce a variety of multimeric BR43x2 analogs. Auxiliary domains can be fused to BR43x2 (TACI or BCMA) polypeptides to target them to specific cells, tissues, or macromolecules. Fusions may also be made using toxins as discussed herein. In this way, polypeptides and proteins can be targeted for therapeutic or diagnostic purposes. A BR43x2 polypeptide can be fused to two or more moieties, such as an affinity tag for purification and a targeting domain. Polypeptide fusions can also comprise one or more cleavage sites, particularly between domains. See, Tuan et al., *Connect. Tiss. Res.* 34:1-9, 1996. Fusions of this type can also be used, for example, to affinity purify cognate ligand from a solution, as an in vitro assay tool, to block signals in vitro by specifically titrating out ligand, to bind ligand on the cell surface or as a BR43x2 antagonists in vivo by administering them to block ligand stimulation. For use in assays, the fusion proteins may be bound to a support via the $F_c$ region and used in an ELISA format.

The invention also provides soluble BR43x2 receptors and polypeptide fragments used to form fusion proteins with affinity tags or labels. Soluble BR43x2-affinity tag fusion proteins are used, for example, to identify the BR43x2 ligands, as well as agonists and antagonists of the natural ligand. Using labeled, soluble BR43x2, cells expressing the ligand, agonists or antagonists are identified by fluorescence immunocytometry or immunohistochemistry. The soluble fusion proteins are useful in studying the distribution of the ligand on tissues or specific cell lineages, and to provide insight into receptor/ligand biology.

To purify ligand, agonists or antagonists, a BR43x2-Ig fusion protein is added to a sample containing the ligand, agonist or antagonist under conditions that facilitate receptor-ligand binding (typically near-physiological temperature, pH, and ionic strength). The receptor-ligand complex is then separated by the mixture using protein A, which is immobilized on a solid support (e.g., insoluble resin beads). The ligand, agonist, antagonist is then eluted using conventional chemical techniques, such as with a salt or pH gradient. In the alternative, the fusion protein itself can be bound to a solid support, with binding and elution carried out as above. Methods for immobilizing receptor polypeptide to a solid support, such as beads of agarose, cross-linked agarose, glass, cellulosic resins, silica-based resins, polystyrene, cross-linked polyacrylamide, or like materials that are stable under the conditions of use are known in the art. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing ligand are passed through the column one or more times to allow ligand to bind to the receptor polypeptide. The ligand is then eluted using changes in salt concentration, chaotropic agents ($MnCl_2$), or pH to disrupt ligand-receptor binding.

To direct the export of the soluble receptor from the host cell, the soluble receptor DNA is linked to a second DNA segment encoding a secretory peptide, such as a t-PA secretory peptide. To facilitate purification of the secreted receptor domain, an N- or C-terminal extension, such as an affinity tag or another polypeptide or protein for which an antibody or other specific binding agent is available, can be fused to the receptor polypeptide.

Cells expressing functional soluble and membrane bound receptors of the present invention are used within screening assays. A variety of suitable assays are known in the art. These assays are based on the detection of a biological response in a target cell. A change in metabolism compared to a control value indicates a test compound that modulates BR43x2 mediated metabolism. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55-63, 1983). An alternative assay format uses cells that are further engineered to express a reporter gene. The reporter gene is linked to a promoter element that is responsive to the receptor-linked pathway, and the assay detects activation of transcription of the reporter gene. Numerous reporter genes that are easily assayed for in cell extracts are known in the art, for example, the *E. coli* lacZ, chloroamphenicol acetyl transferase (CAT) and serum response element (SRE) (see, e.g., Shaw et al., *Cell* 56:563-72, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:29094-101, 1994; Schenborn and Goiffin, *Promega Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may also may be advantageously employed. Such receptor, antibody, member of a complement/anti-complement pair or fragment is immobilized onto the surface of a receptor chip. Use of this instrument is disclosed by Karlsson, *J. Immunol. Meth.* 145:229-40, 1991 and Cunningham and Wells, *J. Mol. Biol.* 234:554-63, 1993. For example, a BR43x2 polypeptide, fragment, antibody or member of a complement/anti-complement pair is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Ligand-binding receptor polypeptides can also be used within other assay systems known in the art. Such systems include Scatchard analysis for determination of binding affinity (see, Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

Scatchard plot analysis for soluble $I^{125}$-ztnf4 binding to TACI and BCMA is shown in FIG. 2 and compared with the binding constants of other members of the TNFR family in Table 5.

TABLE 5

| Ligand | Kd M | Cell source | Reference |
|---|---|---|---|
| TNFa high | 7.14E−11 | HL-60 | a |
| TNFa low | 3.26E−10 | HEP-2 | a |
| TNFa high | 2.00E−10 | HL-60 | b |
| CD27L | 3.70E−10 | MP-1 | c |
| CD27L | 8.30E−09 | MP-1 | c |
| CD40L | 5.00E−10 | EL40.5 | d |
| CD40L (125I-CD40) | 1.00E−09 | EBNA | d |
| 4-1BBL | 1.16E−09 | Biacore | e |
| anti 41BBmab | 4.14E−10 | Biacore | e |
| ztnf4 sol. | 1.11E−09 | TACI-BHK | |
| ztnf4 sol. | 1.25E−09 | BCMA-BHK | | a Hohmann et al., J. Biol. Chem. 264: 14927-34, 1989
b Manna and Aggarwal, J. Biol. Chem. 273: 33333-41, 1998
c Goodwin et al., Cell 73: 447-56, 1993
d Armitage et al., Nature 357: 80-82, 1992
e Shuford et al., J. Exp. Med. 186: 47-55, 1997

As a receptor, the activation of BR43x2 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906-12, 1992; Pitchford et al., *Meth. Enzymol.* 228:84-108, 1997; Arimilli et al., *J. Immunol. Meth.* 212:49-59, 1998; Van Liefde et al., *Eur. J. Pharmacol.* 346:87-95, 1998. The microphysiometer can be used for assaying adherent or non-adherent eukaryotic or prokaryotic cells. By measuring extracellular acidification changes in cell media over time, the microphysiometer directly measures cellular responses to various stimuli, including agonists, ligands, or antagonists of the BR43x2 polypeptide. Preferably, the microphysiometer is used to measure responses of a BR43x2-expressing eukaryotic cell, compared to a control eukaryotic cell that does not express BR43x2 polypeptide. BR43x2-expressing eukaryotic cells comprise cells into which BR43x2 has been transfected, as described herein, creating a cell that is responsive to BR43x2-modulating stimuli; or cells naturally expressing BR43x2, such as BR43x2-expressing cells derived from spleen tissue. Differences, measured by a change in extracellular acidification, for example, an increase or diminution in the response of cells expressing BR43x2, relative to a control, are a direct measurement of BR43x2-modulated cellular responses. Moreover, such BR43x2-modulated responses can be assayed under a variety of stimuli. Also, using the microphysiometer, there is provided a method of identifying agonists and antagonists of BR43x2 polypeptide, comprising providing cells expressing a BR43x2 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change extracellular acidification rate. Antagonists and agonists for BR43x2 polypeptide can be rapidly identified using this method.

The soluble BR43x2 is useful in studying the distribution of ligands on tissues or specific cell lineages, and to provide insight into receptor/ligand biology. Application may also be made of the specificity of TNF receptors for their ligands as a mechanism by which to destroy ligand-bearing target cells. For example, toxic compounds may be coupled to BR43x2 soluble receptor or BR43x2 fusion. Examples of toxic compounds would include radiopharmaceuticals that inactivate target cells; chemotherapeutic agents such as doxorubicin, daunorubicin, methotrexate, and cytoxan; toxins, such as ricin, diphtheria, *Pseudomonas* exotoxin A and abrin; and antibodies to cytotoxic T-cell surface molecules.

Ztnf4 (5 ng/ml) was found to bind to BR43x2 (SEQ ID NO:2), TACI (SEQ ID NO:6), BCMA (SEQ ID NO:8) and BR43x1 (SEQ ID NO:9), by FACS analysis (Flow Cytometry and Sorting, Melamed et al. eds. Wiley-Liss, 1990 and Immunofluorescence and Cell Sorting, Current Protocols in Immunology, Volume 1, Coligan et al. eds. John Wiley & Son, 1997). FITC-tagged, soluble ztnf4 was also shown to bind specifically to, among other things, B lymphocytes in PBMNCs, tonsil cells, to B cell lymphoma cell lines (Raji, Burkitt's human lymphoma, ATCC CCL86), Ramos (Burkitt's lymphoma cell line, ATCC CRL-1596), Daudi (Burkitt's human lymphoma, ATCC CCL213) and RPMI 1788 (a B lymphocyte cell line, ATCC CCL-156) using FACS analysis. No binding was seen with HL-60, (ATCC a promyelocytic cell line, ATCC CCL-240). Specificity for binding to B cells from PBMNC and tonsil cells was confirmed by co-staining with antibodies to B cell specific molecules including CD19, IgD, IgM, and CD20. Similarity of ztnf4 to CD40L suggested a broader tissue distribution than was seen. Affinity of ztnf4 was tested on monocytes, dendritic cells, and purified T cells using cytokine proliferation and T cell proliferation assays, for example, and could not detect binding of ztnf4 or any other biological effect on any other type of cell tested. Therefore, the specificity for B cells by the ligand and receptor suggests that they are useful for the study and treatment of autoimmunity, B cell cancers, immunomodulation, IBD and any antibody-mediated pathologies, e.g. ITCP, myasthenia gravis and the like, renal diseases, indirect T cell immune response, graft rejection, graft versus host disease.

Ztnf4 has been shown to activate B cells resulting in B cell proliferation, antibody production and up-regulation of activation markers in vitro (see examples below). These affects may require co-stimulation via IL-4 or other cytokines or stimulation through the B cell antigen receptor or other cell surface receptors which activate B cells, i.e., CD40. Other tumor necrosis factor ligands, such as gp39 and TNFβ, also stimulate B cell proliferation. Thus the polypeptides of the current invention can be targeted to specifically regulate B cell responses, inhibiting activated B cells, during the immune response without affecting other cell populations which is advantageous in the treatment of disease. Additionally, the polypeptides of the present invention could be used to modulate B cell development, development of other cells, antibody production and cytokine production. BR43x2 polypeptides can also find use in inducing apoptosis and/or anergy within cells. Polypeptides of the present invention could also modulate T and B cell communication by neutralizing the proliferative effects of ztnf4. Bioassays and ELISAs are available to measure cellular response to ztnf4 in the presence of soluble BR43x2, TACI and/or BCMA. Other assays include those which measure changes in cytokine production as a measure of cellular response (see for example, *Current Protocols in Immunology* ed. John E. Coligan et al., NIH, 1996). Assays to measure other cellular responses, including antibody isotype, monocyte activation, NK cell formation, antigen presenting cell function, apoptosis.

BR43x2 polypeptides of the present invention would be useful to neutralize the effects of ztnf4 for treating pre-B or B-cell leukemias, such as plasma cell leukemia, chronic or acute lymphocytic leukemia, myelomas such as multiple myeloma, plasma cell myeloma, endothelial myeloma and giant cell myeloma; and lymphomas such as non-Hodgkins lymphoma, for which an increase in ztnf4 polypeptides is associated. Soluble BR43x2 would be a useful component in a therapy regime for inhibiting tumor progression and survival.

Northern blot analysis showed ztnf4 is expressed in $CD8^+$ cells, monocytes, dendritic cells, activated monocytes. This suggests that in some autoimmune disorders, cytotoxic T-cells might stimulate B-cell production through excess production of ztnf4. Immunosuppressant proteins that selectively block the action of B-lymphocytes would be of use in treating disease. Autoantibody production is common to several autoimmune diseases and contributes to tissue destruction and exacerbation of disease. Autoantibodies can also lead to the occurrence of immune complex deposition complications and lead to many symptoms of systemic lupus erythomatosis, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis, (Korganow et al., *Immunity* 10:451-61, 1999). As such, inhibition of ztnf4 antibody production would be beneficial in treatment of autoimmune diseases such as myasthenia gravis and rheumatoid arthritis. Immunosuppressant therapeutics such as soluble BR43x2 that selectively block or neutralize the action of B-lymphocytes would be useful for such purposes. To verify these capabilities in BR43x2 soluble receptor polypeptides of the present invention, such BR43x2 polypeptides are evaluated using assays known in the art and described herein.

The invention provides methods employing BR43x2, TACI or BCMA polypeptides, fusions, antibodies, agonists or antagonists for selectively blocking or neutralizing the actions of B-cells in association with end stage renal diseases, which may or may not be associated with autoimmune diseases. Such methods would also be useful for treating immunologic renal diseases. Such methods would be would be useful for treating glomerulonephritis associated with diseases such as membranous nephropathy, IgA nephropathy or Berger's Disease, IgM nephropathy, Goodpasture's Disease, post-infectious glomerulonephritis, mesangioproliferative disease, chronic lymphoid leukemia, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HIV-related diseases, amyloidosis or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis.

The methods of the present invention also include use of BR43x2, TACI or BCMA polypeptides, fusions, antibodies, agonists or antagonists in the treatment of hypertensive or large vessel diseases, including renal artery stenosis or occlusion and cholesterol emboli or renal emboli.

The present invention also provides methods for diagnosis and treatment of renal or urological neoplasms, multiple mylelomas, lymphomas, light chain neuropathy or amyloidosis.

The invention also provides methods for blocking or inhibiting activated B cells using BR43x2, TACI, or BCMA polypeptides, fusions, antibodies, agonists or antagonists for the treatment of asthma and other chronic airway diseases such as bronchitis and emphysema.

Also provided are methods for inhibiting or neutralizing an effector T cell response using BR43x2, TACI, or BCMA polypeptides, fusions, antibodies, agonists or antagonists for use in immunosuppression, in particular for such therapeutic use as for graft-versus-host disease and graft rejection. Additional use would be found in regulation of the immune response, in particular the activation and regulation of lymphocytes. BR43x2, TACI, or BCMA polypeptides, fusions, antibodies, agonists or antagonists would be useful in therapies for treating immunodeficiencies. BR43x2, TACI, or BCMA polypeptides, fusions, antibodies, agonists or antagonists would be useful in therapeutic protocols for treatment of such autoimmune diseases as insulin dependent diabetes mellitus (IDDM) and Crohn's Disease. Methods of the present invention would have additional therapeutic value for treating chronic inflammatory diseases, in particular to lessen joint pain, swelling, anemia and other associated symptoms as well as treating septic shock.

The effect of soluble BR43x2, TACI, or BCMA polypeptides and fusion proteins on immune response can be measured by administering the polypeptides of the present invention to animals immunized with antigen followed by injection of ztnf4 and measuring antibody isotype production and B and T cell responses including delayed type hypersensitivity and in vitro proliferation and cytokine production according to the methods known in the art.

The present invention therefore provides a method of inhibiting ztnf4 activity in a mammal comprising administering to said mammal an amount of a compound selected from the group consisting of: a) a polypeptide of SEQ ID NO:4; b) a polypeptide of SEQ ID NO:8; c) a fusion protein; d) a polypeptide of SEQ ID NO:6 from amino acid residue 1 to residue 166; e) a polypeptide of SEQ ID NO:8 from amino acid residue 1 to residue 150; f) an antibody or antibody fragment which specifically binds to a polypeptide of SEQ ID NO:4; and g) an antibody or antibody fragment which specifically binds to a polypeptide of SEQ ID NO:10. Examples of fusion proteins include fusions of soluble BR43x2 (SEQ ID NO:4), TACI (from amino acid residue 1 to residue 166 of SEQ ID NO:6) or BCMA (from amino acid residue 1 to residue 150 of SEQ ID NO:8) with another polypeptide, preferably an immunoglobulin heavy chain constant region Fc fragment. The invention similarly provides a method for inhibiting BR43x2, TACI or BCMA receptor-ligand engagement.

Such methods would be particularly useful where ztnf4 activity is associated with activated B lymphocytes and for treating pre-B cell or B-cell cancers. Such methods would also be useful where ztnf4 activity is associated with antibody production. In particular, antibody production associated with autoimmune diseases such as systemic lupus erythomatosis, myasthenia gravis or rheumatoid arthritis.

The present invention also provides BR43x2 agonists and antagonists. Compounds identified as BR43x2 agonists are useful for modifying the proliferation and development of target cells in vitro and in vivo. For example, agonist compounds are useful alone or in combination with other cytokines and hormones as components of defined cell culture media. Agonists are thus useful in specifically mediating the growth and/or development of BR43x2-bearing B lymphocytes cells in culture. Agonists and antagonists may also prove useful in the study of effector functions of B lymphocytes, in particular B lymphocyte activation and differentiation. Antagonists are useful as research reagents for characterizing ligand-receptor interaction.

Compounds identified as BR43x2 antagonists are also useful to boost the humoral immune response. B cell responses are important in fighting infectious diseases including bacterial, viral, protozoan and parasitic infections. Antibodies against infectious microorganisms can immobilize the pathogen by binding to antigen followed by complement mediated lysis or cell mediated attack. A BR43x2 antagonist would serve to boost the humoral response and would be a useful therapeutic for individuals at risk for an infectious disease or as a supplement to vaccination.

The invention also provides antagonists, which either bind to BR43x2 polypeptides or, alternatively, to a ligand to which BR43x2 polypeptides bind, thereby inhibiting or eliminating the function of BR43x2. Such BR43x2 antagonists would include antibodies; oligonucleotides which bind either to the BR43x2 polypeptide or to its ligand; natural or synthetic analogs of BR43x2 ligands which retain the ability to bind the receptor but do not result in either ligand or receptor signaling. Such analogs could be peptides or peptide-like compounds. Natural or synthetic small molecules which bind to BR43x2 polypeptides and prevent signaling are also contemplated as antagonists. As such, BR43x2 antagonists would be useful as therapeutics for treating certain disorders where blocking signal from either a BR43x2 receptor or ligand would be beneficial. Antagonists are useful as research reagents for characterizing ligand-receptor interaction. BR43x2 is expressed on transformed B cell lines including EBV induced and spontaneous Burkitt's lymphoma and several B cell myelomas. Inhibiting the function of BR43x2 would be useful in the treatment of B cell lymphomas or multiple myelomas. BR43x2 antagonists, such as BR43x2 soluble receptors or antibodies, could be used therapeutically to mediate tumor progression.

The activity of agonists and antagonists can be determined by activity assays which determine the potency of receptor/ligand engagement. Stably transfected B-cell lines, such as Ba43 (a murine pre-B cell line Palacios and Steinmetz, ibid. and Mathey-Prevot et al., ibid.), which co-express high levels of reporter gene constructs for NFKB, NFAT-1 and AP-1 were made which express BR43x2. Cell lines expressing TACI and BCMA were also be prepared in a similar manner and in Jurkat and other B lymphoma cell lines. Ztnf4 was found to signal through the reporter genes in these constructs. Soluble BR43x2 and antibodies can be used to measure binding.

An in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161-89, 1994; and Douglas and Curiel, *Science & Medicine* 4:44-53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts may be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145-55, 1994). With either protocol, an expressed, secreted heterologous protein can be repeatedly isolated from the cell culture supernatant. Within the infected 293S cell production protocol, non-secreted proteins may also be effectively obtained.

Well established animal models are available to test in vivo efficacy of soluble BR43x2, TACI, or BCMA polypeptides of the present invention in certain disease states. In particular, soluble BR43x2, TACI, or BCMA polypeptides and polypeptide fragments can be tested in vivo in a number of animal models of autoimmune disease, such as MRL-lpr/lpr or NZBxNZW F1 congenic mouse strains which serve as a model of SLE (systemic lupus erythematosus). Such animal models are known in the art, see for example *Autoimmune Disease Models* A Guidebook, Cohen and Miller eds. Academic Press. Offspring of a cross between New Zealand Black (NZB) and New Zealand White (NZW) mice develop a spontaneous form of SLE that closely resembles SLE in humans. The offspring mice, known as NZBW begin to develop IgM autoantibodies against T-cells at 1 month of age, and by 5-7 months of age, Ig anti-DNA autoantibodies are the dominant immunoglobulin. Polyclonal B-cell hyperactivity leads to overproduction of autoantibodies. The deposition of these autoantibodies, particularly ones directed against single stranded DNA is associated with the development of glomerulonephritis, which manifests clinically as proteinuria, azotemia, and death from renal failure. Kidney failure is the leading cause of death in mice affected with spontaneous SLE, and in the NZBW strain, this process is chronic and obliterative. The disease is more rapid and severe in females than males, with mean survival of only 245 days as compared to 406 days for the males. While many of the female mice will be symptomatic (proteinuria) by 7-9 months of age, some can be much younger or older when they develop symptoms. The fatal immune nephritis seen in the NZBW mice is very similar to the glomerulonephritis seen in human SLE, making this spontaneous murine model very attractive for testing of potential SLE therapeutics (Putterman and Naparstek, *Murine Models of Spontaneous Systemic Lupus Erythematosus*, Autoimmune Disease Models: A Guidebook, chapter 14, pp. 217-34, 1994; Mohan et al., *J. Immunol.* 154:1470-80, 1995; and Daikh et al., *J. Immunol.* 159:3104-08, 1997). Administration of soluble TACI-IG, BR43x2-Ig, BCMA-Ig or other soluble and fusion proteins to these mice to evaluate the efficacy of TACI, BR43x2, or BCMA to amelioration of symptoms and alterations to the course of disease is described below in the Example section.

Mouse models for experimental allergic encephalomyelitis (EAE) has been used as a tool to investigate both the mechanisms of immune-mediated disease, and methods of potential therapeutic intervention. The model resembles human multiple sclerosis, and produces demyelination as a result of T-cell activation to neuroproteins such as myelin basic protein (MBP), or proteolipid protein (PLP). Inoculation with antigen leads to induction of CD4+, class II MHC-restricted T-cells (Th1). Changes in the protocol for EAE can produce acute, chronic-relapsing, or passive-transfer variants of the model (Weinberg et al., *J. Immunol.* 162:1818-26, 1999; Mijaba et al., *Cell. Immunol.* 186:94-102, 1999; and Glabinski, *Meth. Enzym.* 288:182-90, 1997). Administration of soluble TACI-IG, BR43x2-Ig, BCMA-Ig or other soluble and fusion proteins to these mice to evaluate the efficacy of TACI, BR43x2, or BCMA to amelioration of symptoms and alterations to the course of disease is described below in the Example section.

In the collagen-induced arthritis (CIA) model, mice develop chronic inflammatory arthritis which closely resembles human rheumatoid arthritis (RA). Since CIA shares similar immunological and pathological features with RA, this makes it an ideal model for screening potential human anti-inflammatory compounds. Another advantage in using the CIA model is that the mechanisms of pathogenesis are known. The T and B cell epitopes on type II collagen have been identified, and various immunological (delayed-type hypersensitivity and anti-collagen antibody) and inflammatory (cytokines, chemokines, and matrix-degrading enzymes) parameters relating to immune-mediating arthritis have been determined, and can be used to assess test compound efficacy in the models (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995). Administration of soluble TACI-IG, BR43x2-Ig, BCMA-Ig or other soluble and fusion proteins to these mice to evaluate the efficacy of TACI, BR43x2, or BCMA to amelioration of symptoms and alterations to the course of disease is described below in the Example section.

Models for bronchial infection, such as asthma, can be created when mice are injected with ovalbumin and restimulated nasally with antigen which produces an asthmatic response in the bronchi similar to asthma. Administration of soluble TACI-Ig, BR43x2-Ig, BCMA-Ig, or other soluble and fusion proteins to these mice to evaluate the efficacy of TACI, BR43x2, or BCMA to amelioration of symptoms and alterations to the course of disease is described below in the Example section.

Myasthenia gravis (MG) is another autoimmune disease for which murine models are available. MG is a disorder of neuromuscular transmission involving the production of autoantibodies directed against the nicotinic acetylcholine receptor (AChR). MG is acquired or inherited with clinical features including abnormal weakness and fatigue on exertion.

A mouse model of MG have been established. (Christadoss et al., *Establishment of a Mouse Model of Myasthenia gravis Which Mimics Human Myasthenia gravid Pathogenesis for Immune Intervention*, in Immunobiology of Proteins and Peptides VIII, Atassi and Bixler, eds., 1995, pp. 195-99.) Experimental autoimmune myasthenia gravis (EAMG) is an antibody mediated disease characterized by the presence of antibodies to AChR. These antibodies destroy the receptor leading to defective neuromuscular electrical impulses, resulting in muscle weakness. In the EAMG model, mice are immunized with the nicotinic acetylcholine receptor. Clinical signs of MG become evident weeks after the second immunization. EAMG is evaluated by several methods including measuring serum levels of AChR antibodies by radioimmunoassay (Christadoss and Dauphinee, *J. Immunol.* 136:2437-40, 1986; and Lindstrom et al., *Methods Enzymol.* 74:432-60, 1981), measuring muscle AChR, or electromyography (Wu et al. *Protocols in Immunology.* Vol. 3, Eds. Coligen, Kruisbeak, Margulies, Shevach, and Strober. John Wiley and Sons, New York, p. 15.8.1, 1997).

Another use for in vivo models includes delivery of an antigen challenge to the animal followed by administration of soluble BR43x2 (TACI) or its ligand ztnf4 and measuring the T and B cell response.

T cell dependent and T cell independent immune response can be measured as described in Perez-Melgosa et al., *J. Immunol.* 163:1123-7, 1999.

Immune response in animals subjected to a regular antigen challenge (for example, ovalbumin or collagen) followed by administration of BR43x2, TACI or BCMA polypeptides or soluble Ig-fusions can be done to measure effect on B cell response.

Pharmacokinetic studies can be used in association with radiolabeled, soluble BR43x2, TACI or BCMA polypeptides or fusions to determine the distribution and half life of such polypeptides in vivo. Additionally animal models can be used to determine the effects of soluble BR43x2, TACI or BCMA on tumors and tumor development in vivo.

Also provided is the use of BR43x2, TACI or BCMA polypeptides as surrogate markers for autoimmune diseases, kidney diseases, B and T cell diseases. Such patients can be bled and BR43x2, TACI or BCMA soluble receptors and their ligands can be detected in the blood.

The invention also provides antibodies. Antibodies to BR43x2 or peptides having an amino acid sequence of SEQ ID NO:8, can be obtained, for example, using as an antigen the product of an expression vector containing the polypeptide of interest, or a polypeptide isolated from a natural source. Particularly useful antibodies "bind specifically" with BR43x2 or peptides having an amino acid sequence of SEQ ID NO:10. Antibodies are considered to be specifically binding if the antibodies bind to a BR43x2 polypeptide or a polypeptide of SEQ ID NO:8, peptide or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660, 1949). Suitable antibodies include antibodies that bind with BR43x2, in particular the extracellular domain of BR43x2 (amino acid residues 1-120 of SEQ ID NO:2) and those that bind with polypeptides having an amino acid sequence of SEQ ID NO:10.

Anti-BR43x2 antibodies can be produced using antigenic BR43x2 epitope-bearing peptides and polypeptides. Antigenic epitope-bearing peptides and polypeptides of the present invention contain a sequence of at least nine, preferably between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with BR43x2. It is desirable that the amino acid sequence of the epitope-bearing peptide is selected to provide substantial solubility in aqueous solvents (i.e., the sequence includes relatively hydrophilic residues, while hydrophobic residues are preferably avoided). Hydrophilic peptides can be predicted by one of skill in the art from a hydrophobicity plot, see for example, Hopp and Woods (*Proc. Nat. Acad. Sci. USA* 78:3824-8, 1981) and Kyte and Doolittle (*J. Mol. Biol.* 157: 105-142, 1982). Moreover, amino acid sequences containing proline residues may be also be desirable for antibody production.

Polyclonal antibodies to recombinant BR43x2 protein or to BR43x2 isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems,* 2nd Edition, Glover et al. (eds.), page 15 (Oxford University Press 1995). The immunogenicity of a BR43x2 polypeptide can be increased through the use of an adjuvant, such as alum (aluminum hydroxide) or Freund's complete or incomplete adjuvant. Polypeptides useful for immunization also include fusion polypeptides, such as fusions of BR43x2 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, hamsters, guinea pigs, goats or sheep, an anti-BR43x2 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310, 1990. Antibodies can also be raised in transgenic animals such as transgenic sheep, cows, goats or pigs, and may be expressed in yeast and fungi in modified forms as will as in mammalian and insect cells.

Alternatively, monoclonal anti-BR43X2 antibodies can be generated. Rodent monoclonal antibodies to specific antigens may be obtained by methods known to those skilled in the art (see, for example, Kohler et al., *Nature* 256:495, 1975, Coligan et al. (eds.), *Current Protocols in Immunology*, Vol. 1, pages 2.5.1-2.6.7 (John Wiley & Sons 1991), Picksley et al., "Production of monoclonal antibodies against proteins expressed in *E. coli*," in *DNA Cloning* 2: Expression Systems, *2nd Edition*, Glover et al. (eds.), page 93 (Oxford University Press 1995)).

Briefly, monoclonal antibodies can be obtained by injecting mice with a composition comprising a BR43x2 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-BR43x2 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nat. Genet* 7:13, 1994, Lonberg et al., *Nature* 368:856, 1994, and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of anti-BR43x2 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230, 1960, Porter, *Biochem. J.* 73:119, 1959, Edelman et al., in *Methods in Enzymology* Vol. 1, page 422 (Academic Press 1967), and by Coligan, ibid.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Natl. Acad. Sci. USA* 69:2659, 1972. Alternatively, the variable chains can be linked by an intermolecular disulfide bond or cross-linked by chemicals such as gluteraldehyde (see, for example, Sandhu, *Crit. Rev. Biotech.* 12:437, 1992).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97, 1991, also see, Bird et al., *Science* 242:423, 1988, Ladner et al., U.S. Pat. No. 4,946,778, Pack et al., *Bio/Technology* 11:1271, 1993, and Sandhu, ibid.

As an illustration, a scFV can be obtained by exposing lymphocytes to BR43x2 polypeptide in vitro, and selecting antibody display libraries in phage or similar vectors (for instance, through use of immobilized or labeled BR43x2 protein or peptide). Genes encoding polypeptides having potential BR43x2 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the BR43x2 sequences disclosed herein to identify proteins which bind to BR43x2.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-BR43x2 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. USA* 86:3833, 1989. Techniques for producing humanized monoclonal antibodies are described, for example, by Jones et al., *Nature* 321:522, 1986, Carter et al., *Proc. Nat. Acad. Sci. USA* 89:4285, 1992, Sandhu, *Crit. Rev. Biotech.* 12:437, 1992, Singer et al., *J. Immun.* 150:2844, 1993, Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et al., U.S. Pat. No. 5,693,762 (1997).

Polyclonal anti-idiotype antibodies can be prepared by immunizing animals with anti-BR43x2 antibodies or antibody fragments, using standard techniques. See, for example, Green et al., "Production of Polyclonal Antisera," in *Methods*

In Molecular Biology: Immunochemical Protocols, Manson (ed.), pages 1-12 (Humana Press 1992). Also, see Coligan, ibid. at pages 2.4.1-2.4.7. Alternatively, monoclonal anti-idiotype antibodies can be prepared using anti-BR43x2 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875, 1996.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, BR43x2 polypeptides or anti-BR43x2 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Soluble BR43x2 polypeptides or antibodies to BR43x2 can be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, BR43x2 polypeptides or anti-BR43x2 antibodies, or bioactive fragments or portions thereof, can be coupled to detectable or cytotoxic molecules and delivered to a mammal having cells, tissues or organs that express the anti-complementary molecule.

Suitable detectable molecules can be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules can be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies can also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Such polypeptide-toxin fusion proteins or antibody/fragment-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain can be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates. The bioactive polypeptide or antibody conjugates described herein can be delivered intravenously, intraarterially or intraductally, or may be introduced locally at the intended site of action.

Antibodies can be made to soluble, BR43x2 polypeptides which are His or FLAG™ tagged. Antibodies can also be prepared to *E. coli* produced MBP-fusion proteins. Alternatively, such polypeptides could include a fusion protein with Human Ig. In particular, antiserum containing polypeptide antibodies to His-tagged, or FLAG™-tagged soluble BR43x2 can be used in analysis of tissue distribution of BR43x2 by immunohistochemistry on human or primate tissue. These soluble BR43x2 polypeptides can also be used to immunize mice in order to produce monoclonal antibodies to a soluble human BR43x2 polypeptide. Monoclonal antibodies to a soluble human BR43x2 polypeptide can also be used to mimic ligand/receptor coupling, resulting in activation or inactivation of the ligand/receptor pair. For instance, it has been demonstrated that cross-linking anti-soluble CD40 monoclonal antibodies provides a stimulatory signal to B cells that have been sub-optimally activated with anti-IgM or LPS, and results in proliferation and immunoglobulin production. These same monoclonal antibodies act as antagonists when used in solution by blocking activation of the receptor. Monoclonal antibodies to BR43x2 can be used to determine the distribution, regulation and biological interaction of the BR43x2/BR43x2-ligand pair on specific cell lineages identified by tissue distribution studies.

The invention also provides isolated and purified BR43x2, TACI and BCMA polynucleotide probes or primers. Such polynucleotide probes can be RNA or DNA. DNA can be either cDNA or genomic DNA. Polynucleotide probes are single or double-stranded DNA or RNA, generally synthetic oligonucleotides, but may be generated from cloned cDNA or genomic sequences and will generally comprise at least 16 nucleotides, more often from 17 nucleotides to 25 or more nucleotides, sometimes 40 to 60 nucleotides, and in some instances a substantial portion, domain or even the entire BR43x2 gene or cDNA. Probes and primers are generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nt, more preferably 20-30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art. Preferred regions from which to construct probes include the ligand binding region, cysteine-rich pseudo repeats, signal sequences, and the like. Techniques for developing polynucleotide probes and hybridization techniques are known in the art, see for example, Ausubel et al., eds., *Current Protocols in Molecular Biology*, John Wiley and Sons, Inc., NY, 1991.

BR43x2, TACI and BCMA polypeptides and antibodies may be used within diagnostic systems to detect the presence of BR43x2, TACI, and BCMA and BR43x2, TACI, and BCMA ligand polypeptides, such as ztnf4. The information derived from such detection methods would provide insight into the significance of BR43x2 polypeptides in various diseases, and as a would serve as diagnostic tools for diseases for which altered levels of BR43x2 are significant. Altered levels of BR43x2, TACI and BCMA receptor polypeptides may be indicative of pathological conditions including cancer, autoimmune disorders and infectious diseases.

In a basic assay, a single-stranded probe molecule is incubated with RNA, isolated from a biological sample, under conditions of temperature and ionic strength that promote base pairing between the probe and target BR43x2, TACI or BCMA RNA species. After separating unbound probe from hybridized molecules, the amount of hybrids is detected.

Well-established hybridization methods of RNA detection include northern analysis and dot/slot blot hybridization (see, for example, Ausubel ibid. and Wu et al. (eds.), "Analysis of Gene Expression at the RNA Level," in *Methods in Gene Biotechnology*, pages 225-239 (CRC Press, Inc. 1997)). Nucleic acid probes can be detectably labeled with radioisotopes such as $^{32}$P or $^{35}$S. Alternatively, BR43x2 RNA can be detected with a nonradioactive hybridization method (see, for example, Isaac (ed.), *Protocols for Nucleic Acid Analysis by Nonradioactive Probes*, Humana Press, Inc., 1993). Typically, nonradioactive detection is achieved by enzymatic conversion of chromogenic or chemiluminescent substrates. Illustrative nonradioactive moieties include biotin, fluorescein, and digoxigenin.

BR43x2, TACI, and BCMA oligonucleotide probes are also useful for in vivo diagnosis. As an illustration, $^{18}$F-labeled oligonucleotides can be administered to a subject and visualized by positron emission tomography (Tavitian et al, *Nature Medicine* 4:467, 1998).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), Tumor Marker Protocols (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)). PCR primers can be designed to amplify a sequence encoding a particular BR43x2 domain or motif, such as the BR43x2, TACI or BCMA cysteine rich pseudo repeat.

One variation of PCR for diagnostic assays is reverse transcriptase-PCR (RT-PCR). In the RT-PCR technique, RNA is isolated from a biological sample, reverse transcribed to cDNA, and the cDNA is incubated with BR43x2 primers (see, for example, Wu et al. (eds.), "Rapid Isolation of Specific cDNAs or Genes by PCR," in *Methods in Gene Biotechnology*, CRC Press, Inc., pages 15-28, 1997). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or BR43x2, TACI, or BCMA anti-sense oligomers. Oligo-dT primers offer the advantage that various mRNA nucleotide sequences are amplified that can provide control target sequences. BR43x2, TACI, or BCMA sequences are amplified by the polymerase chain reaction using two flanking oligonucleotide primers that are typically at least 5 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled BR43x2 probe, and examined by autoradiography. Additional alternative approaches include the use of digoxigenin-labeled deoxyribonucleic acid triphosphates to provide chemiluminescence detection, and the C-TRAK colorimetric assay.

Another approach is real time quantitative PCR (Perkin-Elmer Cetus, Norwalk, Conn.). A fluorogenic probe, consisting of an oligonucleotide with both a reporter and a quencher dye attached, anneals specifically between the forward and reverse primers. Using the 5' endonuclease activity of Taq DNA polymerase, the reporter dye is separated from the quencher dye and a sequence-specific signal is generated and increases as amplification increases. The fluorescence intensity can be continuously monitored and quantified during the PCR reaction.

Another approach for detection of BR43x2, TACI, or BCMA expression is cycling probe technology (CPT), in which a single-stranded DNA target binds with an excess of DNA-RNA-DNA chimeric probe to form a complex, the RNA portion is cleaved with RNase H, and the presence of cleaved chimeric probe is detected (see, for example, Beggs et al., *J. Clin. Microbiol.* 34:2985, 1996 and Bekkaoui et al., *Biotechniques* 20:240, 1996). Alternative methods for detection of BR43x2, TACI or BCMA sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686, 272 (1997), Dyer et al., *J. Virol. Methods* 60:161, 1996; Ehricht et al., *Eur. J. Biochem.* 243:358, 1997 and Chadwick et al., *J. Virol. Methods* 70:59, 1998). Other standard methods are known to those of skill in the art.

BR43x2, TACI, and BCMA probes and primers can also be used to detect and to localize BR43x2, TACI, or BCMA gene expression in tissue samples. Methods for such in situ hybridization are well-known to those of skill in the art (see, for example, Choo (ed.), *In Situ Hybridization Protocols*, Humana Press, Inc., 1994; Wu et al. (eds.), "Analysis of Cellular DNA or Abundance of mRNA by Radioactive In Situ Hybridization (RISH)," in *Methods in Gene Biotechnology*, CRC Press, Inc., pages 259-278, 1997 and Wu et al. (eds.), "Localization of DNA or Abundance of mRNA by Fluorescence In Situ Hybridization (RISH)," in *Methods in Gene Biotechnology*, CRC Press, Inc., pages 279-289, 1997).

Various additional diagnostic approaches are well-known to those of skill in the art (see, for example, Mathew (ed.), *Protocols in Human Molecular Genetics* Humana Press, Inc., 1991; Coleman and Tsongalis, *Molecular Diagnostics*, Humana Press, Inc., 1996 and Elles, *Molecular Diagnosis of Genetic Diseases*, Humana Press, Inc., 1996).

In addition, such polynucleotide probes could be used to hybridize to counterpart sequences on individual chromosomes. Chromosomal identification and/or mapping of the BR43x2 gene could provide useful information about gene function and disease association. Many mapping techniques are available to one skilled in the art, for example, mapping somatic cell hybrids, and fluorescence in situ hybridization (FISH). A preferred method is radiation hybrid mapping. Radiation hybrid mapping is a somatic cell genetic technique developed for constructing high-resolution, contiguous maps of mammalian chromosomes (Cox et al., *Science* 250:245-50, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other non-polymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

Chromosomal localization can also be done using STSs. An STS is a DNA sequence that is unique in the human genome and can be used as a reference point for a particular chromosome or region of a chromosome. An STS can be defined by a pair of oligonucleotide primers that can be used in a polymerase chain reaction to specifically detect this site in the presence of all other genomic sequences. Since STSs are based solely on DNA sequence they can be completely described within a database, for example, Database of Sequence Tagged Sites (dbSTS), GenBank, National Center for Biological Information, National Institutes of Health, Bethesda, Md. http://www.ncbi.nlm.nih.gov), they can be searched with a gene sequence of interest for the mapping data contained within these short genomic landmark STS sequences.

The present invention also provides reagents for additional diagnostic applications. For example, the BR43x2 gene, a probe comprising BR43x2 DNA or RNA, or a subsequence thereof can be used to determine if the BR43x2 gene is present on a particular chromosome or if a mutation has occurred. Detectable chromosomal aberrations at the BR43x2 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:3, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5-16, 1991), ribonuclease protection assays, and other genetic linkage analysis techniques known in the art (Sambrook et al., ibid.; Ausubel et. al., ibid.; Marian, *Chest* 108:255-65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34-8, 1991).

Antisense methodology can be used to inhibit BR43x2, TACI, or BCMA gene transcription, such as to inhibit B cell development and interaction with other cells. Polynucleotides that are complementary to a segment of a BR43x2, TACI, or BCMA-encoding polynucleotide (e.g., a polynucleotide as set forth in SEQ ID NO:3) are designed to bind to BR43x2, TACI, or BCMA-encoding mRNA and to inhibit translation of such mRNA. Such antisense polynucleotides are used to inhibit expression of BR43x2, TACI, or BCMA polypeptide-encoding genes in cell culture or in a subject.

Mice engineered to express BR43x2, TACI, or BCMA, referred to as "transgenic mice," and mice that exhibit a complete absence of BR43x2, TACI, or BCMA function, referred to as "knockout mice," may also be generated (Snouwaert et al., *Science* 257:1083, 1992; Lowell et al., *Nature* 366:740-42, 1993; Capecchi, Science 244: 1288-92, 1989; Palmiter et al. *Annu Rev Genet.* 20: 465-99, 1986). For example, transgenic mice that over-express BR43x2, TACI, or BCMA either ubiquitously or under a tissue-specific or tissue-restricted promoter can be used to ask whether over-expression causes a phenotype. For example, over-expression of a wild-type BR43x2, TACI, or BCMA polypeptide, polypeptide fragment or a mutant thereof may alter normal cellular processes, resulting in a phenotype that identifies a tissue in which BR43x2, TACI, or BCMA expression is functionally relevant and may indicate a therapeutic target for BR43x2, TACI, BCMA or their agonists or antagonists. For example, a preferred transgenic mouse to engineer is one that over-expresses soluble BR43x2, TACI or BCMA. Moreover, such over-expression may result in a phenotype that shows similarity with human diseases. Similarly, knockout BR43x2, TACI, or BCMA mice can be used to determine where BR43x2 is absolutely required in vivo. The phenotype of knockout mice is predictive of the in vivo effects that a BR43x2, TACI, or BCMA antagonist, such as those described herein, may have. The human BR43x2, TACI, or BCMA cDNA can be used to isolate murine BR43x2, TACI, or BCMA mRNA, cDNA and genomic DNA, which are subsequently used to generate knockout mice. These mice may be employed to study the BR43x2, TACI, or BCMA gene and the protein encoded thereby in an in vivo system, and can be used as in vivo models for corresponding human diseases. Moreover, transgenic expression of BR43x2, TACI, or BCMA antisense polynucleotides or ribozymes directed against BR43x2, TACI, or BCMA, described herein, can be used analogously to transgenic mice described above.

Pharmaceutically effective amounts of BR43x2, TACI, or BCMA polypeptides of the present invention can be formulated with pharmaceutically acceptable carriers for parenteral, oral, nasal, rectal, topical, transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of the BR43x2 polypeptide or antagonist. Such slow release systems are applicable to formulations, for example, for oral, topical and parenteral use. The term "pharmaceutically acceptable carrier" refers to a carrier medium which does not interfere with the effectiveness of the biological activity of the active ingredients and which is not toxic to the host or patient. One skilled in the art may formulate the compounds of the present invention in an appropriate manner, and in accordance with accepted practices, such as those disclosed in *Remington: The Science and Practice of Pharmacy*, Gennaro, ed., Mack Publishing Co., Easton Pa., 19th ed., 1995.

As used herein a "pharmaceutically effective amount" of a BR43x2, TACI, or BCMA polypeptide, agonists or antagonist is an amount sufficient to induce a desired biological result. The result can be alleviation of the signs, symptoms, or causes of a disease, or any other desired alteration of a biological system. For example, an effective amount of a BR43x2, TACI, or BCMA polypeptide is that which provides either subjective relief of symptoms or an objectively identifiable improvement as noted by the clinician or other qualified observer. For example, such an effective amount of a BR43x2, TACI, or BCMA polypeptide or soluble fusion would provide a decrease in B cell response during the immune response, inhibition or decrease in autoantibody production, inhibition of diminution of symptoms associated with SLE, MG or RA. Effective amounts of BR43x2, TACI, or BCMA will decrease the percentage of B cells in peripheral blood. Effective amounts of the BR43x2, TACI, or BCMA polypeptides can vary widely depending on the disease or symptom to be treated. The amount of the polypeptide to be administered and its concentration in the formulations, depends upon the vehicle selected, route of administration, the potency of the particular polypeptide, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Typically a dose will be in the range of 0.1-100 mg/kg of subject. Doses for specific compounds may be determined from in vitro or ex vivo studies in combination with studies on experimental animals. Concentrations of compounds found to be effective in vitro or ex vivo provide guidance for animal studies, wherein doses are calculated to provide similar concentrations at the site of action.

The invention is further illustrated by the following non-limiting examples.

EXAMPLES

Example 1

Identification of BR43x2

The TACI isoform was cloned from RPMI array library using secretion trap approach. An RPMI 1788 (activated B-cell line) library was arrayed using twenty 96-well plates. Each well contained about 100 *E. coli* colonies, with each colony containing one cDNA clone. DNA minipreps were prepared in 96-well format using the TomTech Quadra 9600. The isolated DNA was then pooled into 120 pools which represent 1600 clones each. These pools were transfected into Cos-7 cells and plated into 12-well plates. Three microliters of pool DNA and 5 µl LipofectAMINE were mixed in 92 µl serum-free DMEM media (55 mg sodium pyruvate, 146 mg L-glutamine, 5 mg transferrin, 2.5 mg insulin, 1 µg selenium and 5 mg fetuin in 500 ml DMEM), incubated at room temperature for 30 minutes, followed by addition of 400 µl serum-free DMEM media. The DNA-LipofectAMINE mix was added onto 220,000 Cos-7 cells/well plated on 12-well tissue culture plates and incubated for 5 hours at 37° C. Following incubation, 500 µl of 20% FBS DMEM media (100 ml FBS, 55 mg sodium pyruvate and 146 mg L-glutamine in 500 ml DMEM) was added to each well and the cells were incubated overnight.

The secretion trap screen was performed using biotinylated, FLAG-tagged ztnf4. The cells were rinsed with PBS and fixed for 15 minutes with 1.8% formaldehyde in PBS. The cells were then washed with TNT (0.1 M Tris-HCl, 0.15 M NaCl, and 0.05% Tween-20 in $H_2O$). Cells were permeated with 0.1% Triton-X in PBS for 15 minutes followed by a wash in TNT. The cells were blocked for 1 hour with TNB (0.1 M Tris-HCl, 0.15 M NaCl and 0.5% Blocking Reagent) using a NEN Renaissance® TSA-Direct Kit (NEN, Boston, Mass.) according the manufacturer's instruction. The cells were washed with TNT and blocked for 15 minutes with avidin and then biotin (Vector Labs Cat# SP-2001) washing in-between with TNT. The cells were incubated for 1 hour with 1 µg/ml ztnf4/Flag/Biotin in TNB followed by a TNT wash. The cells were then incubated for one hour with a 1:300 dilution of streptavidin-HRP (NEN) in TNB, and washed with TNT. Hybridizations were detected with fluorescein tyramide reagent diluted 1:50 in dilution buffer (NEN) and incubated for 4.4 minutes and washed with TNT. Cells were preserved with Vectashield Mounting Media (Vector Labs, Burlingame, Calif.) diluted 1:5 in TNT.

The cells were visualized by fluorescent microscopy using a FITC filter. Twelve pools were positive for ztnf4 binding. Pool D8 (representing 1600 clones) was broken down and a single clone (D8-1), positive for ztnf4 binding, was isolated. Sequencing analysis revealed clone, D8-1, contained a polypeptide sequence which encoded an isoform of TACI, in which the Phe21-Arg67 first cysteine-rich pseudo repeat of TACI was replaced by a single amino acid residue, tryptophan. This isoform was designated BR43x2, the polynucleotide sequence of which is presented in SEQ ID NO: 1.

Example 2

Localization of BR43x1 in Lymphocytes and Monocytes

Reverse transcriptase PCR was used to localize BR43x1 expression in T and B cells and monocytes. Oligonucleotide primers ZC19980 (SEQ ID NO:15) and ZC19981 (SEQ ID NO:16) were used to screen CD19$^+$, CD3$^+$ and monocyte cDNA for BR43. The reverse transcriptase reaction was carried out at 94° C. for 3 minutes, followed by 30 cycles of 94° C. for 30 seconds, 68° C. for 2 minutes and 72° C. for 1 minute, followed by a 7 minute extension at 72° C. A band of the expected size, 720 bp, was detected in B cells only and not in activated T cells as had been reported for TACI using antibodies (von Bülow and Bram, ibid.).

Example 3

B Cell Proliferation Assay Using the BR43 Ligand Ztnf4

A vial containing 1×10$^8$ frozen, apheresed peripheral blood mononuclear cells (PBMCs) was quickly thawed in 37° C. water bath and resuspended in 25 ml B cell medium (Iscove's Modified Dulbecco's Medium, 10% heat inactivated fetal bovine serum, 5% L-glutamine, 5% Pen/Strep) in a 50 ml tube. Cells were tested for viability using Trypan Blue (GIBCO BRL, Gaithersburg, Md.). Ten milliliters of Ficoll/Hypaque Plus (Pharmacia LKB Biotechnology Inc., Piscataway, N.J.) was layered under cell suspension and spun for 30 minutes at 1800 rpm and allowed to stop with the brake off. The interphase layer was then removed and transferred to a fresh 50 ml tube, brought up to a final volume of 40 ml with PBS and spun for 10 minutes at 1200 rpm with the brake on. The viability of the isolated B cells was tested using Trypan Blue. The B cells were resuspended at a final concentration of 1×10$^6$ cells/ml in B cell medium and plated at 180 μl/well in a 96 well U bottom plate (Falcon, VWR, Seattle, Wash.).

To the cells were added one of the following stimulators to bring the final volume to 200 ml/well:

Soluble, FLAG-tagged ztnf-4sCF or ztnf-4sNF, at 10 fold dilutions from 1 mg-1 ng/ml either alone, with 10 □g/ml anti-IgM (goat anti Human IgM) diluted in NaH$_2$CO$_3$, ph 9.5, (Southern Biotechnology Associates, Inc., Birmingham, Ala.); or with 10 μg/ml anti-IgM, and 10 ng/ml recombinant human IL4 (diluted in PBS and 0.1% BSA). Additionally, other cytokines such as IL-3 and IL-6 as well as a soluble CD40 (sCD40) antibody (Pharmingen, San Diego, Calif.) were tested as well. As a control the cells incubated with 0.1% bovine serum albumen (BSA) and PBS, 10 μg/ml anti-IgM or 10 μg/ml anti-IgM and 10 ng/ml IL4 (or other cytokines). The cells were then incubated at 37° C. in a humidified incubator for 72 hours. Sixteen hours prior to harvesting, 1 μCi$^3$H thymidine was added to all wells. The cells were harvested into a 96 well filter plate (UniFilter GF/C, Packard, Meriden, Conn.) where they were harvested using a cell harvester (Packard) and collected according to manufacturer's instructions. The plates were dried at 55° C. for 20-30 minutes and the bottom of the wells were sealed with an opaque plate sealer. To each well was added 0.25 ml of scintillation fluid (Microscint-O, Packard) and the plate was read using a Top-Count Microplate Scintillation Counter (Packard).

To measure induction of IgG production in response to various B cell mitogens following stimulation of purified B cells, cells were prepared as described and incubated for 9 days. The cell supernatant was collected to determine IgG production.

To measure cell surface marker activation in response to various B cell mitogens following stimulation of purified B cells, cells were prepared as described above but incubated only 48 hours. Cell surface markers were measured by FACS analysis.

Proliferation of human purified B cells stimulated with the various B cell mitogens is summarized in Table 6:

TABLE 6

| Stimulus | Proliferative Index |
| --- | --- |
| ztnf4 | 1.5 |
| ztnf4 + IL4 | 9.9 |
| ztnf4 + anti-IgM + IL4 | 15.8 |

A synergistic affect of ztnf4 with IL4, IL3 (10 □g/ml) and IL6 (10 μg/ml) was seen on B cell proliferation. A two fold increase in B cell signaling was seen when using sCD40.

Induction of IgG production (ng/ml) in response to various B cell mitogens following stimulation of purified B cells is summarized in Table 7.

TABLE 7

| Stimulus | Control | Ztnf4 |
| --- | --- | --- |
| anti-IgM | 3 | 7.5 |
| anti-IgM + IL-4 | 13 | 32 |
| anti-IgM + IL-4 + IL-5 | 10 | 45 |

An increase in cell surface activation markers after stimulation of purified B cells with ztnf4 alone, or with anti-IgM or anti-IgM+IL-4 was seen. There was no effect on the proliferation of PBMNCs in the presence of optimal or suboptimal T cell mitogens. Also, no affect on TNFα production was seen in purified monocytes in response to LPS stimulation.

Figure 3A:
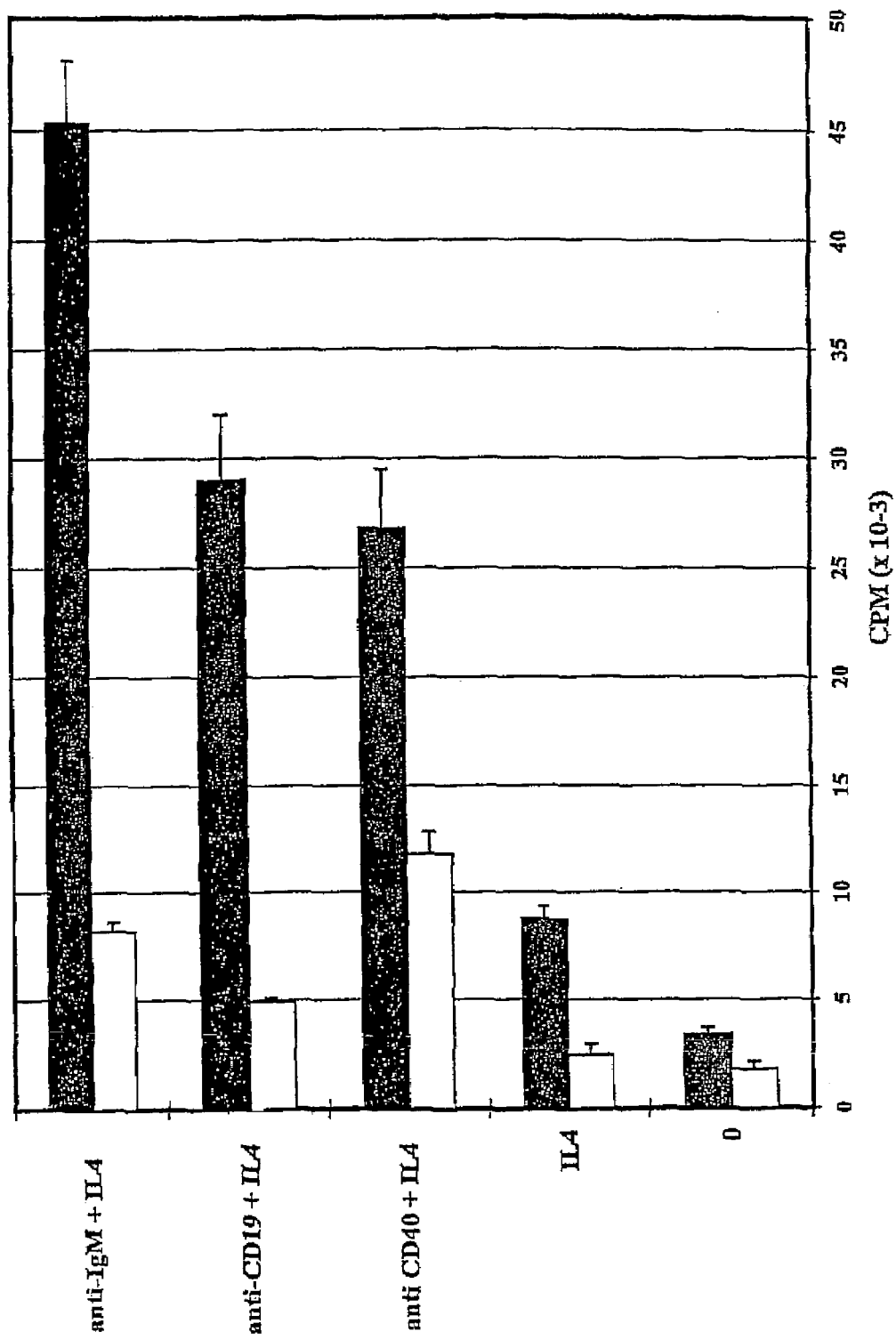
FIG. 3A shows ztnf4 co-activating human B lymphocytes to proliferate and secrete immunoglobulin.
Figure 3B:
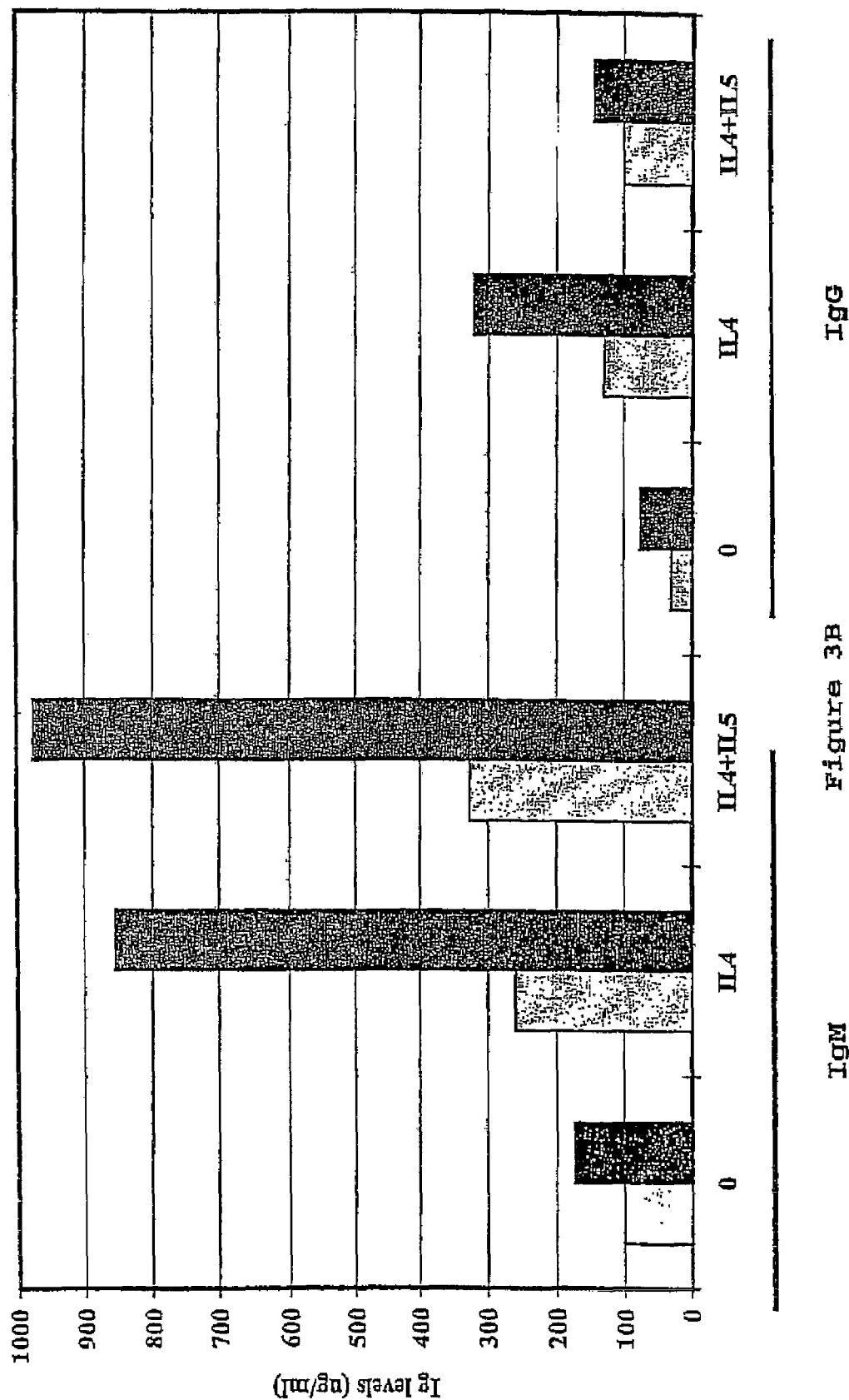
FIG. 3B shows levels of IgM and IgG measured in supernatants obtained from B cells stimulated with soluble ztnf4 in the presence of IL4 or IL4+IL5 after 9 days in culture.

FIG. 3 shows soluble ztnf4 co-activation of human B lymphocytes to proliferate and secrete immunoglobulin. FIG. 3A shows purified human peripheral blood B cells proliferation in response to stimulation with soluble ztnf4 (25 ng/ml) in the presence of IL-4 alone, and IL-4 with anti-IgM, anti-CD40, or anti-CD19, after five days in culture. FIG. 3B shows the levels of IgM and IgG measured in the supernatants obtained from human B cells stimulated with soluble ztnf4 in the presence of IL-4 or IL-4+IL-5, after nine days in culture.

These results suggest that soluble ztnf4 is a B cell activation molecule which acts in concert with other B cell stimuli and weakly by itself. Soluble ztnf4 promotes B cell proliferation and Ig production. The up regulation of adhesion molecules, costimulatory molecules and activation receptors suggests a role for promoting APC function of B cells.

Figure 4:
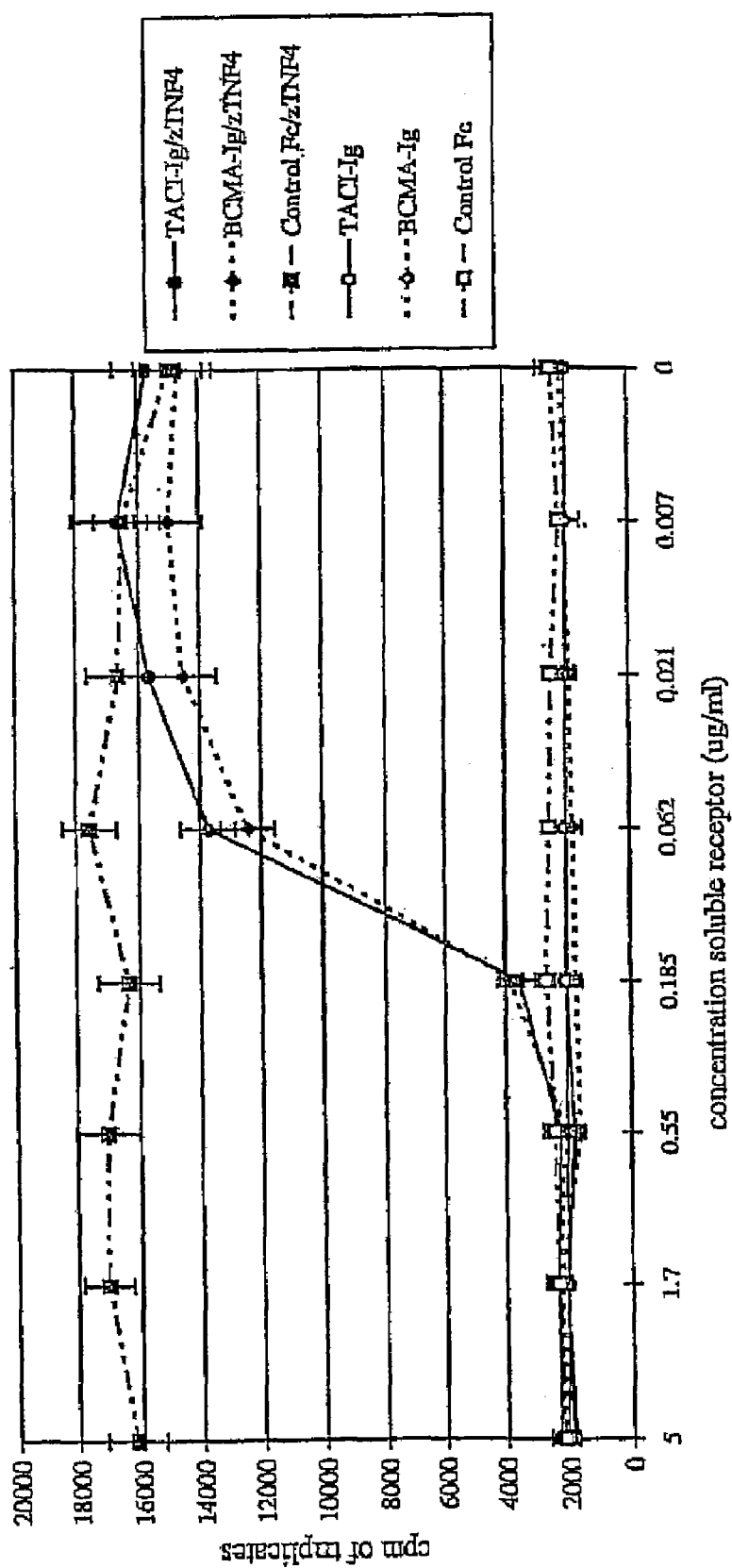
FIG. 4 shows human peripheral blood B cells stimulated with soluble ztnf4 or control protein (ubiquitin) in the presence of IL-4 for 5 days in vitro. Purified TACI-Ig, BCMA-Ig and control Fc were tested for inhibition of ztnf4 specific proliferation.

FIG. 4 shows stimulation of human peripheral blood B cells with soluble ztnf4 (25 ng/ml) or a control protein (ubiquitin) in the presence of 10 ng/ml IL-4 for 5 days in vitro.

Purified TACI-Ig, BCMA-Ig, or control Fc were tested for inhibition of soluble ztnf4 specific proliferation.

Example 4

Selecting TACI and BCMA Transformed BHK Cells Using Ztnf4 Binding

BHK cells expressing a high level of TACI protein were selected by dilution cloning of a transfectant pool. Transfectant cells ($2\times10^5$) were incubated on ice for 30 minutes with biotinylated ztnf4 at 1 µg/ml in binding buffer (PBS, 2% BSA, 0.02% $NaN_3$). Cells were washed 2× with binding buffer, then incubated with SA-PE (Caltag) (1:1000 dilution in binding buffer) on ice for 30 minutes. Cells were then washed 2× in binding buffer, resuspended in binding buffer, and read by FACS (FACS Vantage, Becton Dickinson). Clones with the highest binding of TNF4 are selected.

BHK cells expressing a high level of BCMA protein were selected by surface labeling the BCMA-expressing transfectant pool with biotinylated ztnf4. This was followed by streptavidin-Phyco-Erythrin (SA-PE Caltag Burlingame, Calif.) and sterile sorting for bright cells in FL2 on the FACS Vantage (Becton Dickinson). The single colonies were then screened for ztnf4 binding.

Example 5

Tissue Distribution

Human Multiple Tissue Northern Blots (MTN I, MTN II and MTN III; Clontech) were probed to determine the tissue distribution of human BR43x2 and TACI expression. An approximately 500 bp PCR derived probe (SEQ ID NO:21) was amplified using BR43x2 (SEQ ID NO: 1) as templates and oligonucleotide ZC20061 (SEQ ID NO:22) and ZC20062 (SEQ ID NO:23) as primers. This sequence is identical to the homologous region of TACI. The amplification was carried out as follows: 1 cycle at 94° C. for 1.0 minutes, 30 cycles of 94° C. for 30 seconds, 60° C. for 30 seconds and 72° C. for 30 seconds, followed by 1 cycle at 72° C. for 10 minutes. The PCR products were visualized by agarose gel electrophoresis and the 500 bp PCR product was purified using a Gel Extraction Kit (Qiagen, Chatsworth, Calif.) according to manufacturer's instructions. The probe was radioactively labeled using the MULTIPRIME DNA labeling kit (Amersham, Arlington Heights, Ill.) according to the manufacturer's instructions. The probe was purified using a NUCTRAP push column (Stratagene). EXPRESSHYB (Clontech) solution was used for prehybridization and as a hybridizing solution for the Northern blots. Hybridization took place overnight at 65° C. using $10^6$ cpm/ml of labeled probe. The blots were then washed in 2×SSC and 0.1% SDS at room temp, followed by 2 washes in 0.1×SSC and 0.1% SDS at 50° C. A transcript of approximately 1.5 kb was detected in spleen, lymph node and small intestine.

Human Multiple Tissue Northern Blots (MTN I, MTN II and MTN III; Clontech) were probed to determine the tissue distribution of human BCMA expression. An approximately 257 bp PCR derived probe (SEQ ID NO:24) was amplified using Daudi cell cDNA as a template and oligonucleotide ZC21065 (SEQ ID NO:25) and ZC21067 (SEQ ID NO:26) as primers. The amplification was carried out as follows: 1 cycle at 94° C. for 1.0 minutes, 35 cycles of 94° C. for 30 seconds, 60° C. for 30 seconds and 72° C. for 30 seconds, followed by 1 cycle at 72° C. for 10 minutes. The PCR products were visualized by agarose gel electrophoresis and the 257 bp PCR product was purified using a Gel Extraction Kit (Qiagen, Chatsworth, Calif.) according to manufacturer's instructions. The probe was radioactively labeled using the MULTIPRIME DNA labeling kit (Amersham, Arlington Heights, Ill.) according to the manufacturer's instructions. The probe was purified using a NUCTRAP push column (Stratagene). EXPRESSHYB (Clontech) solution was used for prehybridization and as a hybridizing solution for the Northern blots. Hybridization took place overnight at 65° C. using $10^6$ cpm/ml of labeled probe. The blots were then washed in 2×SSC and 0.1% SDS at room temp, followed by 2 washes in 0.1× SSC and 0.1% SDS at 50° C. A transcript of approximately 1.2 kb was detected in stomach, small intestine, lymph node, trachea, spleen and testis.

RNA Master Dot Blots (Clontech) that contained RNAs from various tissues that were normalized to 8 housekeeping genes was also probed with either the TACI probe (SEQ ID NO:21) or the BCMA probe (SEQ ID NO:24) and hybridized as described above. BR43x2/TACI expression was seen in spleen, lymph node, small intestine, stomach, salivary gland, appendix, lung, bone marrow and fetal spleen. BCMA expression was detected in small intestine, spleen, stomach, colon, lymph node and appendix.

A human Tumor Panel Blot V (Invitrogen Inc., San Diego, Calif.) and a human lymphoma blot (Invitrogen) were probed as described above either with a Br43x2/TACI probe (SEQ ID NO:21) or a BCMA probe (SEQ ID NO:24). A 1.5 kb transcript corresponding to TACI was found in non-Hodgkin's lymphoma and parotid tumor. A 1.2 kb transcript corresponding to BCMA was found in adenolymphoma, non-Hodgkins lymphoma, and parotid tumor.

Total RNA from CD4+, CD8+, CD19+ and mixed lymphocyte reaction cells (CellPro, Bothell, Wash.) was prepared using guanidine isothiocyanate (Chirgwin et al., *Biochemistry* 18:52-94, 1979), followed by a CsCl centrifugation step. Poly(A)+ RNA was isolated using oligo d(T) cellulose chromatography (Aviv and Leder, *Proc. Natl. Acad. Sci. USA.* 69:1408-12, 1972). Northern blot analysis was then performed as follows.

About 2 mg of each of the poly A+ RNAs was denatured in 2.2 M formaldehyde/phosphate buffer (50 mM $Na_2HPO_4$, 50 mM $NaH_2PO_4$, 50 mM NaOAc, 1 mM EDTA and 2.2 M formaldehyde) and separated by 1.5% agarose mini gel (Stratagene Cloning Systems, La Jolla, Calif.) electrophoresis in formaldehyde/phosphate buffer. The RNA was blotted overnight onto a nytran filter (Schleicher & Schuell, Keene, N.H.), and the filter was UV crosslinked (1,200 mjoules) in a STRATALINKER® UV crosslinker (Stratagene Cloning Systems) and then baked at 80° C. for 1 hour.

The blots were probed with either a TACI (SEQ ID NO:21) or BCMA (SEQ ID NO: 24) probe. A 1.5 kb band representing TACI was detected only in CD 19+cells. A 1.2 kb transcript representing BCMA was detected faintly in CD $8^+$, CD $19^+$ and MLR cells.

Additional Northern Blot analysis was carried out on blots made with poly(A) RNA from K-562 cells (erythroid, ATCC CCL 243), HUT78 cells (T cell, ATCC TIB-161), Jurkat cells (T cell), DAUDI (Burkitt's human lymphoma, Clontech, Palo Alto, Calif.), RAJI (Burkitt's human lymphoma, Clontech) and HL60 (Monocyte) as described above. The blots were probed with either a TACI (SEQ ID NO:21) or BCMA (SEQ ID NO:24) probe. A transcript of 1.5 kb corresponding to TACI was detected in Raji cells. A transcript of 1.2 kb corresponding to BCMA was detected in Daudi, Raji and Hut 78 cells.

A PCR-based screen was used to identify tissues which expressed human or murine TACI and human BCMA. Human and Murine Rapid-Scan™ Gene Expression Panels (OriGene Technologies, Inc., Rockville, Md.), were screened according to manufacturer's instructions. Oligonucleotide primers ZC24200 (SEQ ID NO:27) and ZC24201 (SEQ ID NO:28) were designed to span an exon junction and produce a 272 bp fragment corresponding to murine TACI. Expression was detected in spleen, thymus, lung, breast, heart, muscle, skin, adrenal gland, stomach, small intestine, brain, ovary, prostate gland and embyro. Additional bands of 500 and 800 bp were detected in many tissues.

Oligonucleotide primers ZC24198 (SEQ ID NO:29) and ZC24199 (SEQ ID NO:30) were designed to span an exon junction and produce a 204 bp fragment corresponding to human TACI. Expression was detected in spleen, brain, heart, liver, colon, lung, small intestine, muscle, stomach, testis, placenta, salivary gland, adrenal gland, pancreas, prostate, peripheral blood lymphocytes and bone marrow.

Oligonucleotide primers ZC24271 (SEQ ID NO:31) and ZC24272 (SEQ ID NO:32) were designed to span an exon junction and produce a 329 bp fragment corresponding to human BCMA. Expression was detected in brain, spleen, colon, lung, small intestine, stomach, ovary, testis, salivary gland, adrenal gland, prostate, peripheral blood lymphocytes, bone marrow and fetal liver.

Oligonucleotide primers ZC24495 (SEQ ID NO:33) and ZC24496 (SEQ ID NO:34) were designed to span an exon junction and produce a 436 bp fragment corresponding to murine BCMA. Expression was detected in liver.

Example 6

Preparation of TACI-IG and BCMA-IG Fusion Vectors Ig Gamma1 Fc4 Fragment Construction To prepare the TACI-Ig fusion protein, the Fc region of human IgG1 (the hinge region and the CH2 and CH3 domains) was modified so as to remove Fc receptor (FcgRI) and complement (C1q) binding functions. This modified version of human IgG1 Fc was called Fc4.

The Fc region was isolated from a human fetal liver library (Clontech) by PCR using oligo primers ZC10,134 (SEQ ID NO:43) and ZC10,135 (SEQ ID NO:44). PCR was used to introduce mutations within the Fc region to reduce FcgRI binding. The FcgRI binding site (Leu-Leu-gly-Gly) was mutated to Ala-Glu-gly-Ala (amino acid residues 38-41 of SEQ ID NO:45) according to Baum et al. (*EMBO J.* 13:3992-4001, 1994), to reduce FcR1 binding (Duncan et al., *Nature* 332:563-4, 1988). Oligonucleotide primers ZC15,345 (SEQ ID NO:46) and ZC15,347 (SEQ ID NO:47) were used to introduce the mutation. To a 50 µl final volume was added 570 ng IgFc template, 5 µl 10×Pfu reaction Buffer (Stratagene), 8 µl of 1.25 mM dNTPs, 31 µl dH₂O, 2 µl 20 mM ZC15,345 (SEQ ID NO:46) and ZC15,347 (SEQ ID NO:47). An equal volume of mineral oil was added and the reaction was heated to 94° C. for 1 minute. Pfu polymerase (2.5 units, Stratagene) was added followed by 25 cycles at 94° C. for 30 seconds, 55° C. for 30 seconds, 72° C. for 1 minute followed by a 7 minute extension at 72° C. The reaction products were electrophoresed and the band corresponding to the predicted size of ~676 bp was detected. The band was excised from the gel and recovered using a QIAGEN QIAquick™ Gel Extraction Kit (Qiagen) according to the manufacturers instructions.

PCR was also used to introduce a mutation of Ala to Ser (amino acid residue 134 of SEQ ID NO:45) and Pro to Ser (amino acid residue 135 of SEQ ID NO:45) to reduce complement C1q binding and/or complement fixation (Duncan and Winter, *Nature* 332:788, 1988) and the stop codon TAA. Two, first round reactions were done using the FcγRI binding site-mutated IgFc sequence as a template. To a 50 µl final volume was added 1 µl FcγRI binding site mutated IgFc template, 5 µl 10×Rfu Reaction Buffer (Stratagene), 8 µl 1.25 mM dNTPs, 31 µl dH₂O, 2 µl 20 mM ZC15,517 (SEQ ID NO:48), a 5' primer beginning at nucleotide 26 of SEQ ID NO:45 and 2 µl 20 mM ZC15,530 (SEQ ID NO:49), a 3' primer beginning at the complement of nucleotide 405 of SEQ ID NO:45. The second reaction contained 2 µl each of 20 mM stocks of oligonucleotide primers ZC15,518 (SEQ ID NO:50), a 5' primer beginning at nucleotide 388 of SEQ ID NO:45 and ZC15,347 (SEQ ID NO:47), a 3' primer, to introduce the Ala to Ser mutation, Xba I restriction site and stop codon. An equal volume of mineral oil was added and the reactions were heated to 94° C. for 1 minute. Pfu polymerase (2.5 units, Stratagene) was added followed by 25 cycles at 94° C. for 30 seconds, 55° C. for 30 seconds, 72° C. for 2 minutes followed by a 7 minute extension at 72° C. The reaction products were electrophoresed and bands corresponding to the predicted sizes, ~370 and ~395 bp respectively, were detected. The bands were excised from the gel and extracted using a QIAGEN QIAquick™ Gel Extraction Kit (Qiagen) according to the manufacturers instructions. A second round reaction was done to join the above fragments and add the 5' Bam HI restriction site. To a 50 µl final volume was added 30 µl dH₂O, 8 µl 1.25 mM dNTPs, 5 µl 10×Pfu polymerase reaction buffer (Stratagene) and 1 µl each of the two first two PCR products. An equal volume of mineral oil was added and the reaction was heated to 94° C. for 1 minute. Pfu polymerase (2.5 units, Stratagene) was added followed by 5 cycles at 94° C. for 30 seconds, 55° C. for 30 seconds, and 72° C. for 2 minutes. The temperature was again brought to 94° C. and 2 µl each of 20 mM stocks of ZC15,516 (SEQ ID NO:51), a 5' primer beginning at nucleotide 1 of SEQ ID NO:45, and ZC15,347 (SEQ ID NO:47) were added followed by 25 cycles at 94° C. for 30 seconds, 55° C. for 30 seconds and 72° C. for 2 minutes, and a final 7 minute extension at 72° C. A portion of the reaction was visualized using gel electrophoresis. A 789 bp band corresponding the predicted size was detected.

TACI-Fc4 and BCMA-Fc4 Expression Vector Construction

Expression plasmids containing TACI-Fc4 and BCMA-Fc4 fusion proteins were constructed via homologous recombination in yeast. A fragment of TACI cDNA was isolated using PCR that included the polynucleotide sequence from nucleotide 15 to nucleotide 475 of SEQ ID NO:5. The two primers used in the production of the TACI fragment were: (1) a primer containing 40 bps of the 5' vector flanking sequence and 17 bps corresponding to the amino terminus of the TACI fragment (SEQ ID NO:52); (2) 40 bps of the 3' end corresponding to the flanking Fc4 sequence and 17 bp corresponding to the carboxyl terminus of the TACI fragment (SEQ ID NO:53). To an 100 µl final volume was added 10 ng TACI template, 10 µl 10× Taq polymerase Reaction Buffer (Perkin Elmer), 8 µl 2.5 nM dNTPs, 78 µl dH₂O, 2 µl each of 20 mM stocks of oligonucleotide primers SEQ ID NO:52 and SEQ ID NO:53, and taq polymerase (2.5 units, Life Technology). An equal volume of mineral oil was added and the reaction was heated to 94° C. for 2 minutes, followed by 25 cycles at 94° C. for 30 seconds, 65° C. for 30 seconds, 65° C. for 30 seconds, 72° C. for 1 minute followed by a 5 minute extension at 72° C.

A fragment of BCMA cDNA was isolated using PCR that includes the polynucleotide sequence from nucleotide 219 to nucleotide 362 of SEQ ID NO:7. The two primers used in the production of the BCMA fragment were an oligonucleotide primer containing 40 bps of the 5' vector flanking sequence and 17 bps corresponding to the amino terminus of the BCMA fragment (SEQ ID NO:54); and an oligonucleotide primer containing 40 bps of the 3' end corresponding to the flanking Fc4 sequence and 17 bps corresponding to the carboxyl terminus of the BCMA fragment (SEQ ID NO:55). To a 100 µl final volume was added 10 ng BCMA template, 10 µl 10× Taq polymerase Reaction Buffer (Perkin Elmer), 8 µl 2.5 mM dNTPs, 78 µl H$_2$O, 2 µl each of 20 mM stock solutions of oligonucleotide primers SEQ ID NO:54 and SEQ ID NO:55. An equal volume of mineral oil was added and the reaction was heated to 94° C. for 2 minutes, followed by 25 cycles at 94° C. for 30 seconds, 65° C. for 30 seconds, 72° C. for 1 minute followed by a 5 minute extension at 72° C.

The fragment containing the cDNA encoding the Fc4 fragment was constructed in a similar manner, one for each of the TACI and BCMA fusion constructs. For TACI the two primers used in the production of the Fc4 fragment were (upstream and downstream), an oligonucleotide primer containing 40 bps of the 5' TACI flanking sequence and 17 bps corresponding to the amino terminus of the Fc4 fragment (SEQ ID NO:56); and an oligonucleotide primer containing 40 bps of the 3' end corresponding to the flanking vector sequence and 17 bps corresponding to the carboxyl terminus of the Fc4 fragment (SEQ ID NO:57). For BCMA, the upstream primer in the production of the Fc4 fragment was an oligonucleotide primer containing 40 bps of the 5' BCMA flanking sequence and 17 bps corresponding to the amino terminus of the Fc4 fragment (SEQ ID NO:58). The downstream primer for the Fc4 for the BCMA construct was the same as that described above for TACI-Fc4 (SEQ ID NO:57).

To a 100 µl final volume was added 10 ng Fc4 template described above, 10 µl 10× Taq polymerase Reaction Buffer (Perkin Elmer), 8 µl 2.5 nM dNTPs, 78 µl dH$_2$O, 2 µl each of 20 mM stocks of oligonucleotides SEQ ID NO:56 and SEQ ID NO:57 for TACI and oligonucleotides SEQ ID NO:58 and SEQ ID NO:57 for BCMA, and taq polymerase (2.5 units, Life Technology). An equal volume of mineral oil was added and the reaction was heated to 94° C. for 2 minutes, then 25 cycles at 94° C. for 30 seconds, 65° C. for 30 seconds, 72° C. for 1 minute followed by a 5 minute extension at 72° C.

Ten microliters of each of the 100 µl PCR reactions described above was run on a 0.8% LMP agarose gel (Seaplaque GTG) with 1×TBE buffer for analysis. The remaining 90 µl of each PCR reaction was precipitated with the addition of 5 µl 1 M NaCl and 250 µl of absolute ethanol. The plasmid pZMP6 was cut with SmaI to linearize it at the polylinker. Plasmid pZMP6 was derived from the plasmid pCZR199 (American Type Culture Collection, Manassas, Va., ATCC# 98668) and is a mammalian expression vector containing an expression cassette having the CMV immediate early promoter, a consensus intron from the variable region of mouse immunoglobulin heavy chain locus, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a DHFR gene and the SV40 terminator. The vector pZMP6 was constructed from pCZR199 by replacement of the metallothionein promoter with the CMV immediate early promoter, and the Kozac sequences at the 5' end of the open reading frame.

One hundred microliters of competent yeast cells (S. cerevisiae) were combined with 10 µl containing approximately 1 µg each of either the TACI or the BCMA extracellular domain and the Fc4 PCR fragments appropriate for recombination with each, and 100 ng of SmaI digested pZMP6 vector and transferred to a 0.2 cm electroporation cuvette. The yeast/DNA mixtures were electropulsed at 0.75 kV (5 kV/cm), ∞ ohms, 25 µF. To each cuvette was added 600 µl of 1.2 M sorbitol and the yeast were plated in two 300 µl aliquots onto to URA-D plates and incubated at 30° C.

After about 48 hours, the Ura+ yeast transformants from a single plate were resuspended in 1 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 µl ethanol (EtOH), followed by centrifugation for 10 minutes at 4° C. The DNA pellet was resuspended in 100 µl H$_2$O.

Transformation of electrocompetent E. coli cells (DH10B, GibcoBRL) was done with 0.5-2 ml yeast DNA prep and 40 µl of DH10B cells. The cells were electropulsed at 2.0 kV, 25 mF and 400 ohms. Following electroporation, 1 ml SOC (2% Bacto' Tryptone (Difco, Detroit, Mich.), 0.5% yeast extract (Difco), 10 mM NaCl, 2.5 mM KCl, 10 mM MgCl2, 10 mM MgSO4, 20 mM glucose) was plated in 250 µl aliquots on four LB AMP plates (LB broth (Lennox), 1.8% Bacto' Agar (Difco), 100 mg/L Ampicillin).

Individual clones harboring the correct expression construct for TACI-Fc4 or BCMA-Fc4 were identified by restriction digest to verify the presence of the insert and to confirm that the various DNA sequences have been joined correctly to one another. The insert of positive clones were subjected to sequence analysis. Larger scale plasmid DNA is isolated using the Qiagen Maxi kit (Qiagen) according to manufacturer's instruction Example 7

Mammalian Expression of TACI-Fc4 and BCMA-Fc4

BHK 570 cells (ATCC NO: CRL-10314) were plated in 10 cm tissue culture dishes and allowed to grow to approximately 50 to 70% confluency overnight at 37° C., 5% CO$_2$, in DMEM/FBS media (DMEM, Gibco/BRL High Glucose, (Gibco BRL, Gaithersburg, Md.), 5% fetal bovine serum (Hyclone, Logan, Utah), 1 mM L-glutamine (JRH Biosciences, Lenexa, Kans.), 1 mM sodium pyruvate (Gibco BRL)). The cells were then transfected with either the plasmid TACI-Fc4/pZMP6 or BCMA-Fc4/pZMP6, using Lipofectamine™ (Gibco BRL), in serum free (SF) media formulation (DMEM, 10 mg/ml transferrin, 5 mg/ml insulin, 2 mg/ml fetuin, 1% L-glutamine and 1% sodium pyruvate). TACI-Fc4/pZMP6 or BCMA-Fc4/pZMP6 was diluted into 15 ml tubes to a total final volume of 640 µl with SF media. 35 µl of Lipofectamine™ (Gibco BRL) was mixed with 605 µl of SF medium. The Lipofectamine™ mix was added to the DNA mix and allowed to incubate approximately 30 minutes at room temperature. Five milliliters of SF media was added to the DNA:Lipofectamine™ mixture. The cells were rinsed once with 5 ml of SF media, aspirated, and the DNA:Lipofectamine™ mixture is added. The cells were incubated at 37° C. for five hours, then 6.4 ml of DMEM/10% FBS, 1% PSN media was added to each plate. The plates were incubated at 37° C. overnight and the DNA:Lipofectamine™ mixture was replaced with fresh 5% FBS/DMEM media the next day. On day 5 post-transfection, the cells were split into T-162 flask in selection medium (DMEM/5% FBS, 1% L-GLU, 1% NaPyr). Approximately 10 days post-transfection, two 150 mm culture dishes of methotrexate resistant colonies from each transfection were trypsinized and the cells are pooled and plated into a T-162 flask and transferred to large scale culture.

Example 9

Transgenic Expression of Ztnf4

Transgenic animals expressing ztnf4 genes were made using adult, fertile males (B6C3f1), prepubescent fertile females (B6C3f1), vasectomized males (B6D2f1), and adult fertile females (B6D2f1) (all from Taconic Farms, Germantown, N.Y.). The prepubescent fertile females were superovulated using Pregnant Mare's Serum gonadotrophin (Sigma, St. Louis, Mo.) and human Chorionic Gonadotropin (hCG (Sigma)). The superovulated females were subsequently mated with adult, fertile males, and copulation was confirmed by the presence of vaginal plugs.

Fertilized eggs were collected under a surgical scope (Leica MZ12 Stereo Microscope, Leica, Wetzlar, Germany). The eggs were then washed in hyaluronidase and Whitten's W640 medium (Table 8; all reagents available from Sigma Chemical Co.) that has been incubated with 5% $CO_2$, 5% $O_2$, and 90% $N_2$ at 37° C. The eggs were stored in a 37° C./5% $CO_2$ incubator until microinjection.

TABLE 8

WHITTEN'S 640 MEDIA

| | mgs/200 ml | mgs/500 ml |
|---|---|---|
| NaCl | 1280 | 3200 |
| KCl | 72 | 180 |
| $KH_2PO_4$ | 32 | 80 |
| $MgSO_4$-$7H_2O$ | 60 | 150 |
| Glucose | 200 | 500 |
| $Ca^{2+}$ Lactate | 106 | 265 |
| Benzylpenicillin | 15 | 37.5 |
| Streptomycin $SO_4$ | 10 | 25 |
| $NaHCO_3$ | 380 | 950 |
| Na Pyruvate | 5 | 12.5 |
| $H_2O$ | 200 ml | 500 ml |
| 500 mM EDTA | 100 µl | 250 µl |
| 5% Phenol Red | 200 µl | 500 µl |
| BSA | 600 | 1500 |

The 858 bp open reading frame encoding full length human TACI ligand Blys (SEQ ID NO:35) was amplified by PCR so as to introduce an optimized initiation codon and flanking 5' PmeI and 3' AscI sites using the oligonucleotide primers of SEQ ID NO:36 and SEQ ID NO:37. This PmeI/AscI fragment was subcloned into pKFO24, a B and/or T cell-restricted transgenic vector containing the Ig Em enhancer (690 bp NotI/XbaI from pEmSR; (Bodrug et al., *EMBO J.* 13:2124-30, 1994), the Ig $V_h$ promoter (536 bp HincII/XhoI fragment from pJH1X(-); Hu et al., *J. Exp. Med.* 177:1681-90, 1993), the SV40 16S intron (171 bp XhoI/HindIII fragment from pEmSR), a PmeI/AscI polylinker, and the human growth hormone gene polyadenylation signal (627 bp SmaI/EcoRI fragment; Seeburg, *DNA* 1:239-49, 1982). The transgene insert was separated from plasmid backbone by NotI digestion and agarose gel purification, and fertilized ova from matings of B6C3F1Tac mice described above were microinjected and implanted into pseudopregnant females essentially as previously described (Malik et al., *Molec. Cell. Biol.* 15:2349-58, 1995)

The recipients were returned to cages in pairs, and allowed 19-21 days gestation. After birth, 19-21 days postpartum was allowed before sexing and weaning, and a 0.5 cm biopsy (used for genotyping) was snipped off the tail with clean scissors.

Genomic DNA was prepared from the tail snips using a commercially available kit (DNeasy 96 Tissue Kit; Qiagen, Valencia, Calif.) following the manufacturer's instructions. Genomic DNA was analyzed by PCR using primers designed to the human growth hormone (hGH) 3' UTR portion of the transgenic vector. Primers ZC17251 (SEQ ID NO:38) and ZC17252 (SEQ ID NO:39) amplify a 368-base-pair fragment of hGH. The use of a region unique to the human sequence (identified from an alignment of the human and mouse growth hormone 3' UTR DNA sequences) ensured that the PCR reaction did not amplify the mouse sequence. In addition, primers ZC17156 (SEQ ID NO:40) and ZC17157 (SEQ ID NO:41), which hybridize to vector sequences and amplify the cDNA insert, may be used along with the hGH primers. In these experiments, DNA from animals positive for the transgene generated two bands, a 368-base-pair band corresponding to the hGH 3' UTR fragment and a band of variable size corresponding to the cDNA insert.

Once animals were confirmed to be transgenic (TG), they are back-crossed into an inbred strain by placing a TG female with a wild-type male, or a TG male with one or two wild-type female(s). As pups were born and weaned, the sexes were separated, and their tails snipped for genotyping.

To check for expression of a transgene in a live animal, a survival biopsy is performed. Analysis of the mRNA expression level of each transgene was done using an RNA solution hybridization assay or real-time PCR on an ABI Prism 7700 (PE Applied Biosystems, Inc., Foster City, Calif.) following the manufacturer's instructions.

Cell Preparation and Flow Cytometry

Founder mice were analyzed at various ages. For flow cytometric (FACS) analysis of lymphoid tissues, bone marrow (BM) cells were isolated from femurs and tibias by careful disruption in phosphate-buffered saline (PBS) using a mortar and pestle. Cells were resuspended, depleted of bone fragments by passive sedimentation, and pelleted at 1000×g. Splenocytes, thymocytes, or lymph node cells were obtained by crushing intact tissues between glass slides, then resuspending and pelleting the cells as for BM. Cells were resuspended in FACS wash buffer (FACS WB) (Hank's balanced salt solution, 1% BSA, 10 mM Hepes, pH 7.4) at a concentration of $20 \times 10^6$ cells/ml prior to staining. To stain, $1 \times 10^6$ cells were transferred to 5 ml tubes and washed with 1 ml of FACS WB, then pelleted at 1000×g. Cells were then incubated on ice for 20 minutes in the presence of saturating amounts of the appropriate FITC-, PE- and/or TriColor(TC)-conjugated mAbs in a total volume of 100 ml in FACS WB. Cells were washed with 1.5 ml of WB, pelleted, then resuspended in 400 ml WB and analyzed on a FACSCalibur flow cytometer using CellQuest software (Becton Dickinson, Mountain View, Calif.). Detectors for forward (FSC) and side (SSC) light scatter were set on a linear scale, whereas logarithmic detectors were used for all three fluorescence channels (FL-1, FL-2, and FL-3).

Compensation for spectral overlap between FL channels was performed for each experiment using single color stained cell populations. All cells were collected ungated to disk and data were analyzed using CellQuest software. RBC and dead cells were excluded by electronically gating data on the basis of FSC vs. SSC profiles.

Antibodies

Fluorescein isothiocyanate (FITC)-conjugated anti-CD8 monoclonal antibody (mAb) (clone 53-6.7) and phycoerthyrin (PE)-conjugated anti-CD4 (cloneRM4-5), anti-CD5 (clone 53-7.3), anti-CD19 (clone ID3), and antisyndecan (clone 281-2) mAbs were purchased from PharMingen (San Diego, Calif.). TriColor(TC)-conjugated anti-CD45R/B220 mAb (clone RA3-6B2) was purchased from Caltag.

Transgenic mice over expressing ztnf4 in the lymphoid compartment develop increased numbers of peripheral B cells, increased plasma cells and elevated levels of serum immunoglobulin. These transgenic animals have an increased number of B200+ cells in the spleen, lymph nodes and thymus. The increased number of splenic B cells includes both conventional B-2 cells, and the normally rare population of B-1 cells. In general, B-1 cells are largely confined to the peritoneal and other body cavities, produce low affinity self-reactive antibodies, and have often been associated with the development of autoimmune diseases such as systemic lupus erythematosus SLE.

Older transgenic animals produce autoantibodies, develop proteinurea and sclerotic glomeruli, characteristics of systemic lupus erythematosus.

Figure 5A:
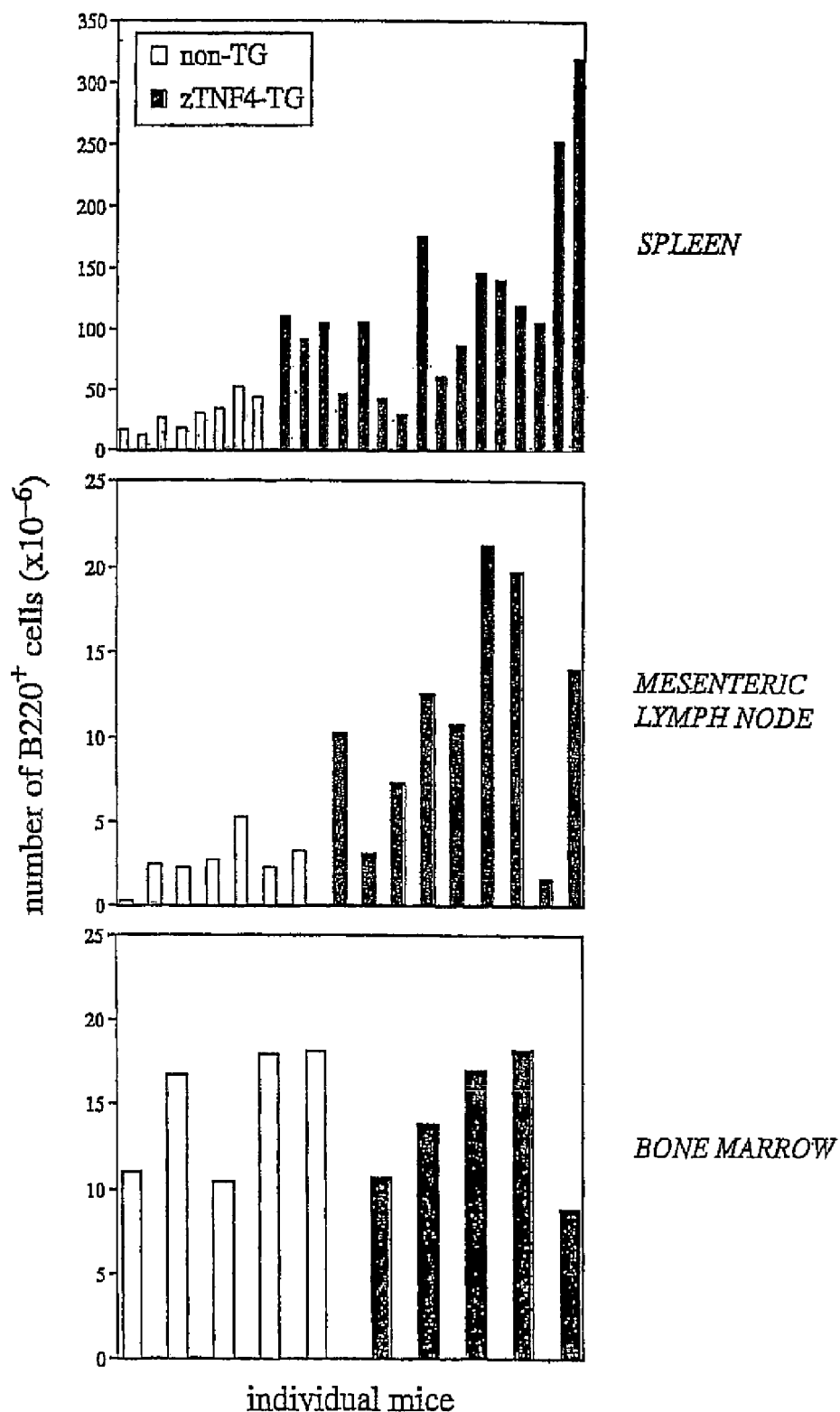
FIG. 5A shows results from ztnf4 transgenic animals that have developed characteristics of SLE.

FIG. 5A shows single cell suspensions of spleen (top panel), mesenteric lymph node (middle panel), and bone marrow (lower panel) prepared as described below, stained with anti-B220-TC and analyzed by flow cytometry. The number of B220+ cells in each tissue was calculated by multiplying the percent B220+ cells by the total number of live (trypan blue excluding) cells counted on a hemocytometer. Each bar represents data from individual ztnf4 transgenic (Tg, shaded bars) or nonTG littermate (open bars) control mice.

Figure 5B:
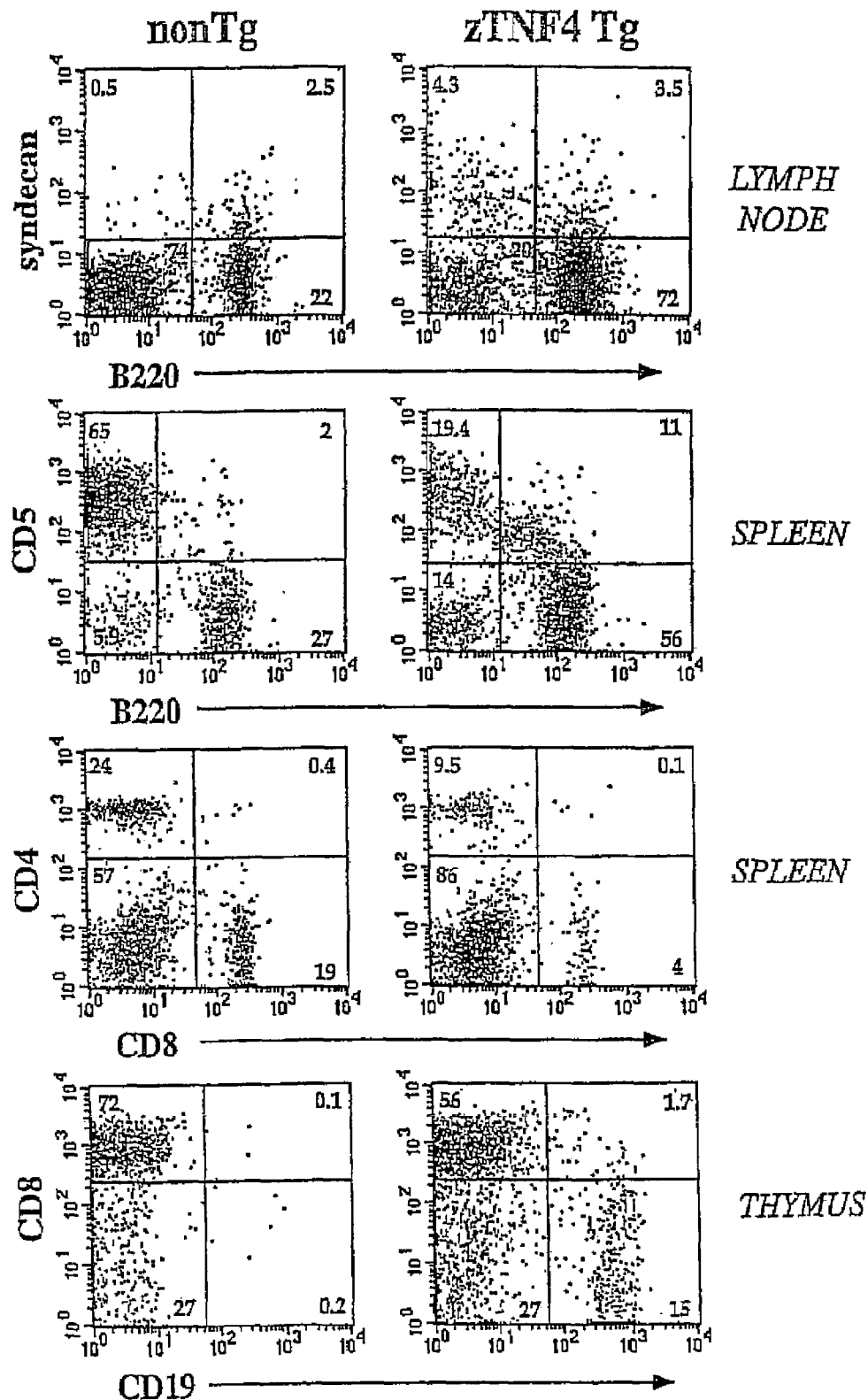
FIG. 5B shows lymph node, spleen and thymus cells from ztnf4 transgenic animals stained with antibodies to CD5, CD4 and CD8.

FIG. 5B shows cells isolated from ztnf4 TG (right-hand panels) or nonTG littermate (left-hand panels) lymph node (top row), spleen (middle rows), and thymus (bottom row) were stained with mAbs to the molecules indicated (DC5, CD4 and CD8), then analyzed by flow cytometry. Data shown were gated to exclude dead cells and RBCs.

Figure 5C:
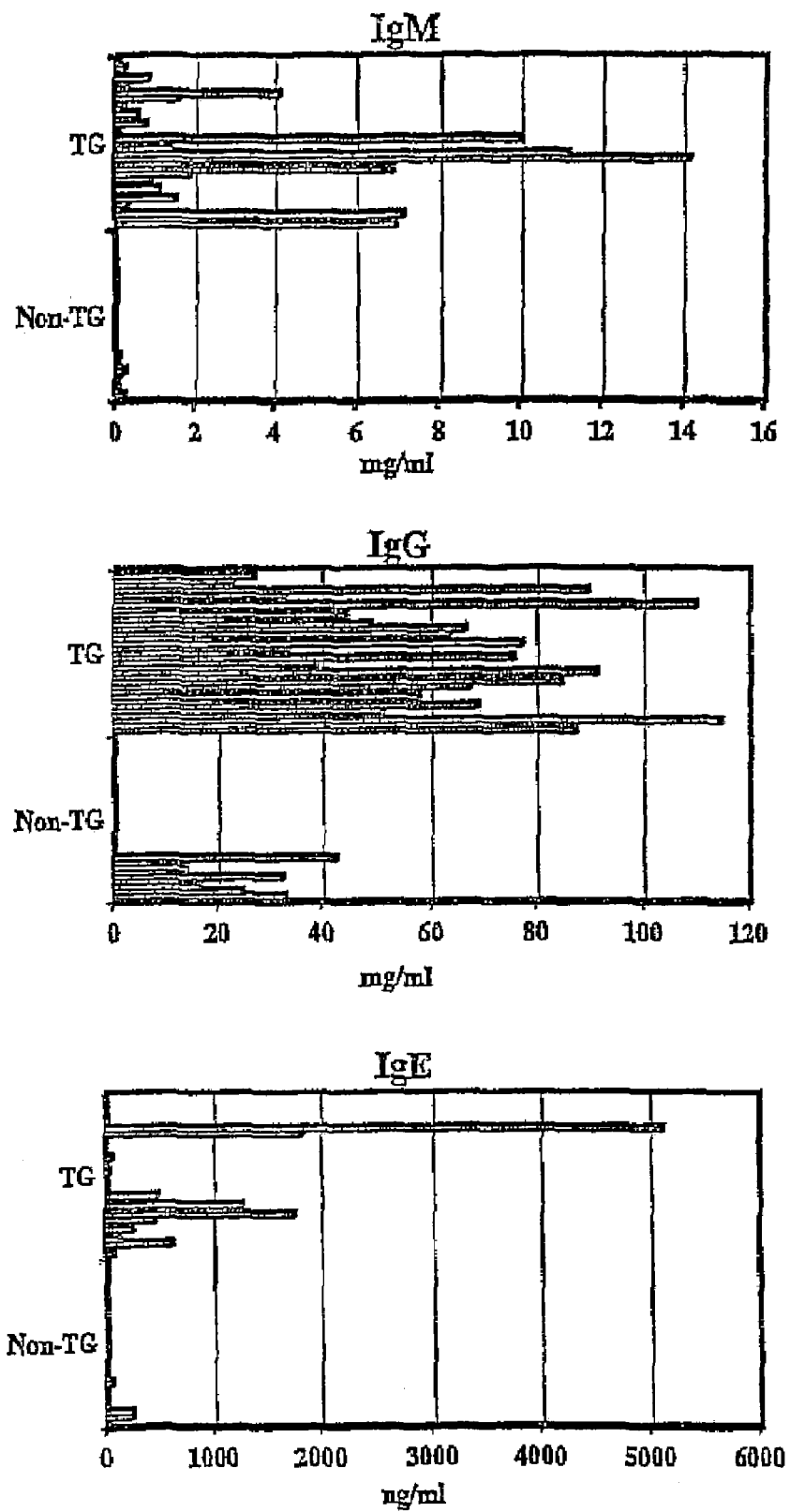
FIG. 5C shows total IgM, IgG and IgE levels in serum from transgenic ztnf4 animals ranging from 6 to 23 weeks of age.

FIG. 5C shows total IgG, IgM, and IgE levels in serum from ztnf4 transgenic mice ranging in age from 6 to 23 weeks old.

Histology revealed amyloid deposition and thickened mesangium of the glomeruli identified in H&E stained kidney sections from ztnf4 transgenic mice compared to normal glomeruli from control littermates.

Figure 5D:
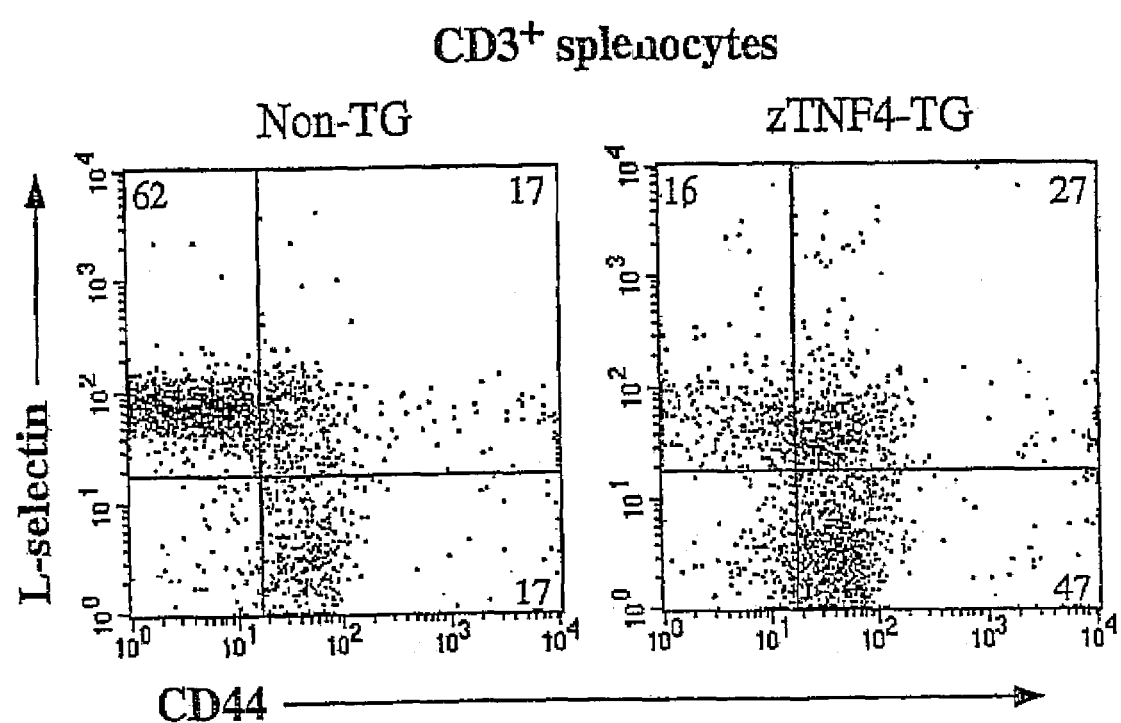
FIG. 5D shows effector T cells in ztnf4 transgenic mice.

FIG. 5D shows an increase in effector T cells in ztnf4 transgenic mice, similar to that reported by Mackay et al. (*J. Exp. Med.* 190:1697-1710, 1999).

Soluble TACI(BR43x2) or BCMA-Ig fusions are injected (IP, IM or IV) into ztnf4 over expressing transgenic animals. Flow cytometric (FACS) analysis of lymphoid tissues will be used to identify any change in the number of B220+B cells in the spleen, lymph nodes and thymus.

Example 10

Direct Binding ELISA

A direct binding ELISA was developed to characterize the ability of either soluble TACI-Ig or soluble BCMA-Ig to bind and inhibit the biological activity of ztnf4 in vitro.

A 96 well plate was coated with 1 µg/ml Goat-anti-Human Ig (Jackson Labs, Bar Harbor, Mass.) in ELISA A buffer (0.1 M $Na_2HCO_3$, pH 9.6, 0.02% $NaN_3$) and incubated overnight at 4° C. TACI, BCMA, and an unrelated TNF receptor such as ztnfr10 (SEQ ID NO:42) as a control were titered from 10 µg/ml through 5 fold dilutions to 320 ng/ml plus a zero and co-incubated with 2.5, 0.5, or 0.1 µg/ml biotinylated ztnf4 or ovalbumin as a negative control, and incubated 1 hour at room temperature.

The co-incubated receptor-biotinylated ligand mixture was then added to the goat-anti-human Ig coated 96 well plates. The plates were then washed (ELISA C, 500 µl Tween 20 (Sigma Chemical Co., St. Louis, Mo.), 200 mg $NaN_3$, PBS to a final volume of 1 liter) and blocked with Superblock (Pierce, Rockford, Ill.). The plates were then incubated at 37° C. for 2 hours.

The plates are once again washed with ELISA C followed by the addition of 100 µl/well of neutr-avidin-HRP at 1:10,000 in ELISA B (5 or 10 µg BSA (Sigma) for 1% or 2% BSA, respectively, 250 µl Tween 20 (Sigma), 100 mg $NaN_3$, phosphate-buffered saline pH 7.2 (PBS, Sigma) to a final volume of 500 ml. Alternatively, the buffer may be made up as 1% or 2% BSA in ELISA C Buffer). The plates are then developed with OPD for 10 minutes at room temperature and read at 492.

Example 11

Biological Activity Assay

A biological activity assay was developed to measure soluble TACI-FC inhibition of human B cell the stimulation by soluble ztnf4. B cells were isolated from peripheral blood mononuclear cells (PBMNC) using CD19 magnetic beads and the VarioMacs magnetic separation system (Miltenyi Biotec Auburn, Calif.) according to the manufacturer's instructions. Purified B cells were mixed with soluble ztnf4 (25 ng/ml) and recombinant human IL-4 (10 ng/ml Pharmingen) and were plated (in triplicate) on to round bottom 96 well plates at $1 \times 10^5$ cells per well.

Soluble TACI-FC was diluted from 5 µg/ml to 6 ng/ml and incubated with the B cell for 5 days, pulsing overnight on day 4 with 1 µCi $^3$H Thymidine (Amersham) per well. As a control soluble TACI-FC was also incubated with B cells and IL-4 without ztnf4 present.

Plates were harvested using Packard plate harvester and counted using the Packard reader. The TACI-Ig soluble receptor inhibited the ability of soluble ztnf4 to stimulate B cell proliferation in vitro in a dose-dependent manner. A 10-fold molar excess TACI-Ig completely inhibits the proliferation of human B cells in response to soluble ztnf4 in the presence of IL-4.

Example 12

ORIGIN Assay

Levels of ztnf4 in individuals with a disease condition (such as SLE, rheumatoid arthritis for example) relative to normal individuals were determined using an electrochemiluminescence assay. A standard curve prepared from soluble, human ztnf4 at 10 ng/ml, 1 ng/ml, 0.1 ng/ml, 0.01 ng/ml and 0 ng/ml was prepared in ORIGIN buffer (Igen, Gaithersburg, Md.). Serum samples were diluted in ORIGIN buffer. The standards and samples were incubated at room temperature for 2 hours with biotinylated rabbit anti-human ztnf4-NF BV antibody diluted to 1 µg/ml in Origin Assay Buffer (IGEN) and ruthenylated rabbit anti-human ztnf4-NF BV polyclonal antibody diluted to 1 µg/ml in Origin Assay Buffer (IGEN). Following the incubation the samples were vortexed and 0.4 mg/ml streptavidin Dynabeads (Dynal, Oslo, Norway) were added to each of the standards and samples at 50 µl/tube and incubated for 30 minutes at room temperature. Samples were then vortexed and samples were read on an Origin Analyzer (Igen) according to manufacturer's instructions. The Origin assay is based on electrochemiluminescence and produces a readout in ECL.

An elevated level of ztnf4 was detected in the serum samples from both NZBWF1/J, and MRL/Mpj-Fas$^{lpr}$ mice which have progressed to advanced stages of glomerulonephritis and autoimmune disease.

Example 13

Soluble TACI-IG in a Spontaneous Model of SLE

NZBW mice become symptomatic for spontaneous SLE at approximately 7-9 months of age. TACI-Fc was administered to NZBW mice to monitor its suppressive effect on B cells over the 5 week period when, on average, B-cell autoantibody production is thought to be at high levels in NZBW mice.

One hundred, 8-week old female (NZB×NZW)F$_1$ mice (Jackson Labs) were divided into 6 groups of 15 mice. Prior to treatment the mice were monitored once a month for urine protein and blood was drawn for CBC and serum banking. Serum will be screened for the presence of autoantibodies. Because proteinuria is the hallmark sign of glomerulonephritis, urine protein levels were monitored by dipstick at regular intervals over the course of the study. Prior to treatment the animals were weighed. Dosing was started when mice were approximately 5 months of age. The mice received intraperitoneal injections of vehicle only (PBS) or human IgG-FC (control protein) or TACI-FC4 (test protein) three times a week for 5 weeks, Table 9.

TABLE 9

| Group (5 mice each) | Treatment | Dose |
|---|---|---|
| 1 | untreated control | |
| 2 | vehicle only | |
| 3 | human IgG-FC | 20 µg |
| 4 | human IgG-FC | 100 µg |
| 5 | human TACI-FC4 | 20 µg |
| 6 | human TACI-FC4 | 100 µg |

Blood was collected twice during dosing and will be collected at least twice following dosing. Urine dipstick values for proteinuria and body weights were made every two weeks after dosing begins. Blood, urine dipstick value and body weight were collected at the time of euthanasia. Weight of spleen, thymus, liver with gall bladder, left kidney and brain were taken. The spleen and thymus were divided for FACS analysis and histology. Submandibular salivary glands, mesenteric lymph node chain, liver lobe with gall bladder, cecum and large intestine, stomach, small intestine, pancreas, right kidney, adrenal gland, tongue with trachea and esophagus, heart and lungs will also be collected for histology.

FIG. 6 shows an elevated level of ztnf4 in serum from NZBWF1 and MRL/lpr/lpr mice that correlates with the development of SLE. FIG. 6A upper panel shows the correlation of ztnf4 serum levels with age, 68 NZBWF1 mice ranging from 10 to 40 weeks old and 10 week and 30 week old NZB/B control mice. The middle panel shows the correlation with proteinuria at three ranges, trace to 20 mg/dl (T-30), 100-300 ng/dl and 2000 mg/dl in NZBWF1 mice compared to control NZB/B mice. The lower panel shows ztnf4 levels with various titers of anti-ds DNA antibody in NZBWF1 mice compared to control NZB/B mice.

FIG. 6B shows the same correlations made on 23 MRL/lpr/lpr mice ranging from 18-24 weeks old and 10 control 11 week old MRL/MpJ mice.

Figure 7:
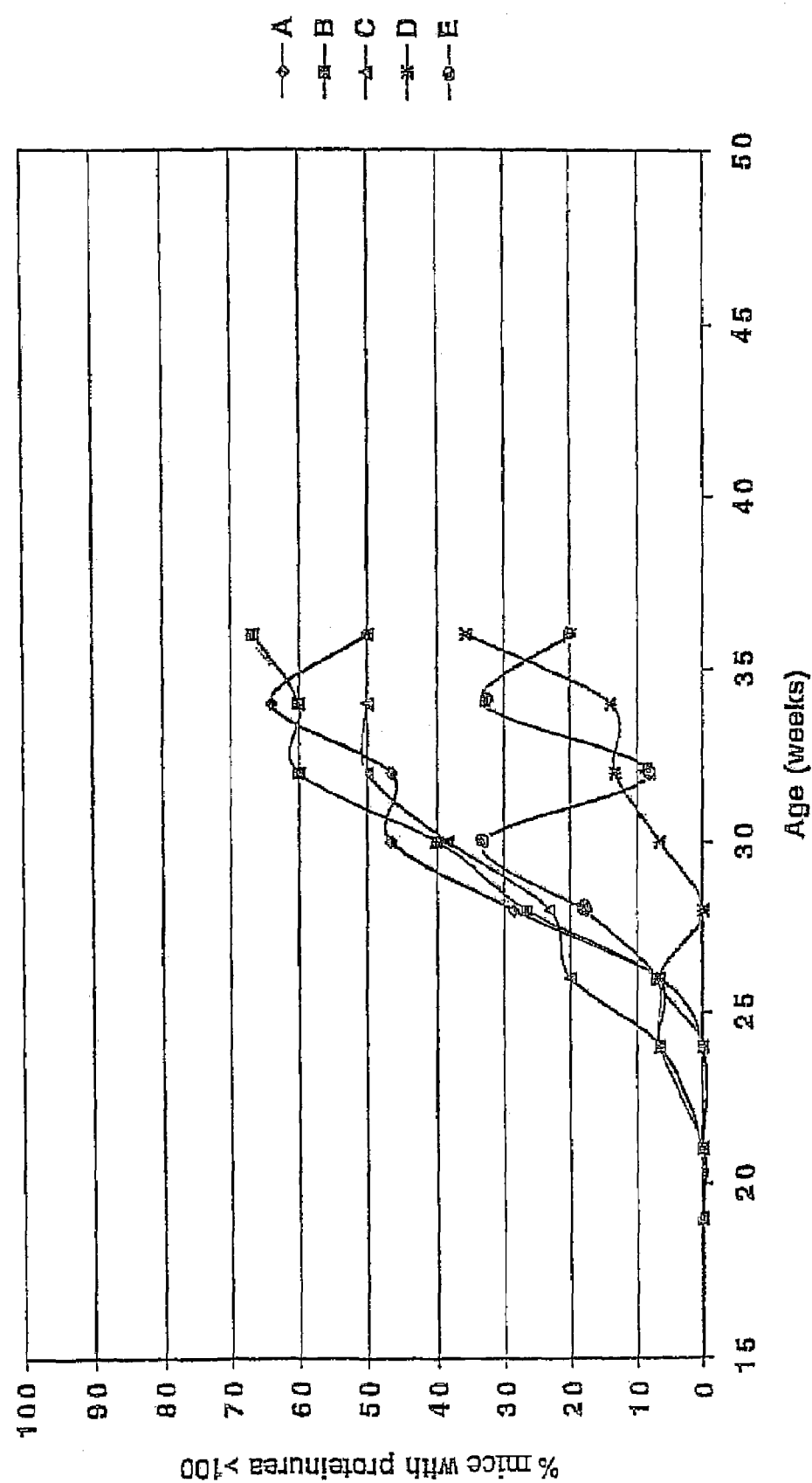
FIG. 7 shows the percentage of NZBWF1 mice that develop proteinurea over the course of the study.

FIG. 7 shows urinalysis results. Mice were considered to have proteinuria if the dipstick reading was ≧100 mg/dl. (A) PBS, (B) human IgG FC, 100 mg, (C) human IgG FC, 20 mg, (D) human TACI-IgG, 100 mg, and (E) human TACI-IgG, 20 mg. Mice treated with the soluble TACI-IgG fusion showed a reduction in proteinuria.

Analysis of peripheral blood from treated animals revealed that white blood cell and lymphocyte counts were reduced in TACI-FC treated mice (20 and 100 mg) when compared to FC (20 and 100 mg) and PBS treated mice, 2 weeks after the start of treatment. FAC analysis (lymphocyte gate) of peripheral blood drawn six weeks after treatment began (two weeks after last treatment was administered) and showed a dramatic decrease in percentage of B cells present in the samples. B cell levels were still in decline at five weeks after last treatment was administered, but not as dramatic. Table 9 provides the average (and standard deviation) for the mice in each treatment group (Table 10). The decline in the percent of B cells in peripheral blood was also observed two weeks into treatment.

TABLE 10

| | Week 2 | | Week 5 |
|---|---|---|---|
| Treatment | % B cells | % T cells | % B cells |
| PBS | 26.05 (6.52) | 67.05 (6.80) | 20.83 (3.14) |
| 100 mg FC | 23.34 (5.77) | 68.23 (7.30) | 25.04 (8.07) |
| 20 mg FC | 24.09 (6.26) | 65.27 (7.18) | 18.96 (6.42) |
| 100 mg TACI-FC | 11.07 (5.03) | 79.06 (6.71) | 14.79 (4.76) |
| 20 mg TACI-FC | 16.37 (7.27) | 69.72 (8.90) | 19.14 (5.27) |

Example 14

Soluble TACI-Ig in Normal Mice

TACI-FC was administered to Blab/C mice to monitor its effect on normal mice. Sixty, 8-week old female Balb/C mice (HSD) were divided into 12 groups of 5 mice. Prior to treatment the mice were weighed and blood was drawn for CBC and serum banking. Groups 1-9 received intraperitoneal injections (IP) of vehicle only (PBS) or human IgG-FC (control protein) or TACI-FC4 (test protein) daily for 12 days and were sacrificed on day 14. Groups 10 and 11 received IP injections three times per week for two weeks and were sacrificed on day 14, Table 11.

TABLE 11

| Group (5 mice each) | Treatment | Dose |
|---|---|---|
| 1 | human TACI-FC4 | 200 mg |
| 2 | human TACI-FC4 | 100 mg |
| 3 | human TACI-FC4 | 20 µg |
| 4 | human TACI-FC4 | 5 µg |
| 5 | human FC4 | 200 mg |
| 6 | human FC4 | 100 mg |
| 7 | human FC4 | 20 mg |
| 8 | human FC4 | 5 mg |
| 9 | vehicle only | as used |
| 10 | human TACI-FC4 | 100 mg |
| 11 | human FC4 | 100 mg |
| 12 | untreated control | |

Blood was collected on days 7 and 12. Blood and body weight were collected at the time of euthanasia. Weight of spleen, thymus, and brain were taken. The spleen and thymus were divided for FACS analysis and histology. Skin, spleen, mesenteric LN chain, submandibular salivary glands, ovary, uterus, cervix, bladder, mesenteric lymph node chain, liver lobe with gall bladder, cecum and large intestine, stomach, small intestine, pancreas, right kidney, adrenal gland, tongue with trachea and esophagus, heart, thymus, thigh muscle, left and right femur, brain will also be collected for histology.

As described above in Example 13, a significant reduction in percent B cells was seen on days 7 (by CBC) and 12 (using FACS) in peripheral blood cells taken from all TACI-FC4 treated samples compared to those treated with FC4 or PBS alone and analyzed by CBC or FACS. Additionally, there was nearly a 50% decrease in B cells in the spleens taken from animals treated with TACI-FC4 as compared to those from FC4 treated mice day 14.

The mice tolerated TACI-FC4 and exhibited no overt health problems. At necropsy, no detectable adverse pathological effect of the TACI-FC4 treatment was observed in the histology performed on the collected organs and tissues. Thymus, spleens, and bone marrow from the animals in each group were pooled and analyzed by flow immunocytometry for T, B and monocyte cell populations in the spleen, T cell subsets in the thymus and immature and mature B cell populations in the bone marrow. There was a 60% drop in the ratio of B to T cells in the spleens of TACI-FC4 treated mice compared with control protein and PBS at the time of sacrifice. This inhibition was detected at 200, 100, and 20 µg daily doses and at the 100 µg dose given three times a week (Table 11a). There were no observable changes in other cell populations in the lymphoid organs analyzed, Table 12a.

To further define the effect of TACI-FC4 on lymphoid cell populations in bone marrow, thymus, spleen, mesenteric lymph nodes and peritoneal exudates cells a second group of mice were treated with 100 µg TACI-FC, FC4, or PBS, three times a week for two weeks.

There were no changes in T cell number or CD4 or CD8 T cell subsets in the thymus or lymph node and no changes in the number of CD11b$^+$ monocytes in the spleen. Mature B cell populations were characterized using antibodies to the cell surface markers CD21, CD23, and B220 in the spleen and IgM, IgD and B220 in the spleen, lymph noted and bone marrow. TACI-FC4 has an effect on the mature B cell populations in spleen, lymph node and bone marrow, and does not appear to have an effect on immature B220+ bone marrow B cells, mature T cells, or monocytes (Table 12b). An increase in the newly formed B cell population in the spleen and lymph node was also detected.

Serum IgM and IgG were in each mouse two days prior to sacrifice. IgM levels decreased while IgG levels remained the same.

TABLE 12A

| Lymphocyte Populations Spleen ($\times 10^7$) | | | |
|---|---|---|---|
| | B | T | Monocyte |
| PBS | 6.8 | 6.9 | 0.5 |
| FC4 | 6.9 | 5.1 | 0.4 |
| TACI-FC4 | 4.1 | 5.5 | 0.4 |

TABLE 12b

| B220+ B-cell Population Spleen ($\times 10^6$) | | | |
|---|---|---|---|
| | Newly Formed CD23$^{lo}$CD21$^{lo}$ | Follicular B CD23$^{hi}$CD21$^{hi}$ | Marginal Zone CD23$^{lo}$CD21$^{hi}$ |
| PBS | 5.1 | 53.0 | 8.8 |
| FC4 | 5.4 | 54.3 | 7.7 |
| TACI-FC4 | 14.8 | 17.0 | 6.0 |
| B220+b-Cell Populations in the Bone Marrow ($\times 10^6$) | | | |
| | Pre-Pro B B220$^{mid}$IgM$^-$IgD$^-$ | Immature B B220$^{mid}$IgM$^+$IgD$^-$ | Mature B220$^{hi}$IgM$^+$IgD$^+$ |
| PBS | 38.0 | 37.0 | 9.34 |
| FC4 | 38.3 | 38.8 | 9.46 |
| TACI-FC4 | 47.9 | 47.9 | 5.6 |

Example 15

Anti-dsDNA ELISA

Autoimmunity is characterized by high levels of anti-double stranded DNA antibodies. To measure the levels anti-dsDNA antibodies in both the over expressing ztnf4 transgenic mice and the NZBW mice an ELISA assay was developed. A 96 well microtiter plate (Nunc) was coated with poly-L-lysine (Sigma) (20 µl/ml in 0.1 M Tris buffer pH 7.3) at 75 µl/well and incubated overnight at room temperature. The plates were then washed in dH$_2$O and coated with poly dAdT (Sigma) (20 µl/ml in 0.1 M Tris buffer pH 7.3) at 75 µl/well and incubated at room temperature for 60 minutes. The plates were then washed with dH$_2$O and blocked with 2% BSA (Sigma) in Tris Buffer for 30 minutes at room temperature followed by a final wash in dH$_2$O.

Serum samples were taken from the ztnf4 transgenic mice described in Example 10 and the NZBW mice described in Example 11. The serum samples were diluted 1:50 in 1% BSA/2% BGG (Calbiochem) in Tris Buffer. The diluted samples were then titrated into the coated plate at 1:50, 1:100, 1:200, 1:400, 1:800, 1:1600, 1:3200 and 1:6400 (50 µl/well) and incubated for 90 minutes at room temperature.

Plates were then washed in dH$_2$O and goat anti-mouse IgG-Fc-HRP (Cappel) diluted to 1:1000 in 1% BSA/2% BGG was added at 50 µl/well. The plates were incubated for 60 minutes at room temperature. The plates were washed 5× in dH$_2$O and developed with OPD, 1 tablet/10 ml Novo D (313 ml 0.1M Na Citrate, 187 ml 0.1M citric acid, pH 5.0) and plated at 100 µl/well. The developer was stopped with 1N H$_2$SO$_4$, 100 µl/well, and the OD read at 492 nm.

Figure 8:
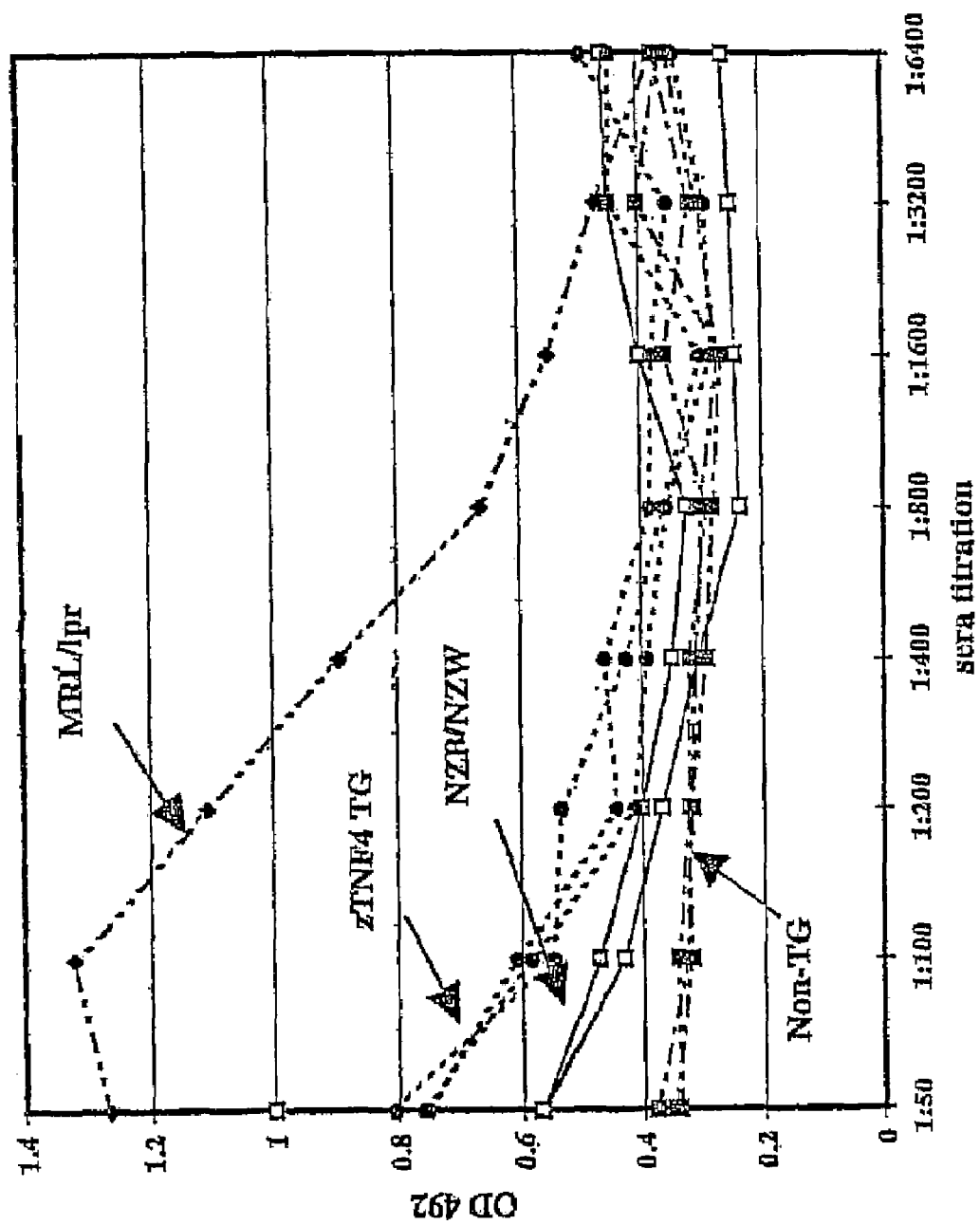
FIG. 8 shows anti-dsDNA levels by ELISA from ztnf4 transgenic mice and control litter mates compared to serum from ZNBWF1 and MRL/lpr/lpr mice.

FIG. 8 shows the anti-ds DNA levels in two ztnf4 transgenic mice (23 week old), two non-transgenic litter mates compared with the levels detected in serum from NZBWF1 (32 week old) and MRL/lpr/lpr (19 week old) mice.

Example 16

Soluble TACI-IG in a Spontaneous Model of EAE

Twenty five female PLxSJL F1 mice (12 weeks old, Jackson Labs) are given a subcutaneous injection of 125 µg/mouse of antigen (myelin Proteolipid Protein, PLP, residues 139-151), formulated in complete Freund's Adjuvant. The mice are divided into 5 groups of 5 mice. Intraperitoneal injections of pertussis toxin (400 ng) are given on Day 0 and 2. The groups will be given a 1×, 10×, or 100× dose of TACI, BCMA or BR43x2, one group will receive vehicle only and one group will receive no treatment. Prevention therapy will begin on Day 0, intervention therapy will begin on day 7, or at onset of clinical signs. Signs of disease, weight loss, and paralysis manifest in approximately 10-14 days, and last for about 1 week. Animals are assessed daily by collecting body weights and assigning a clinical score to correspond to the extent of their symptoms. Clinical signs of EAE appear within 10-14 days of inoculation and persist for approximately 1 week. At the end of the study all animals are euthanized by gas overdose, and necropsied. The brain and spinal column are collected for histology or frozen for mRNA analysis. Body weight and clinical score data is plotted by individual and by group.

| Clinical Score | |
| --- | --- |
| 0 | Normal |
| 0.5 | Weak, tail tone may be reduced but not absent |
| 1 | Limp tail (cannot lift tail when mouse is picked up at base of tail) |
| 2 | Limp tail, weak legs (cannot lift tail, can stay upright on hind legs but legs are shaky) |
| 3 | Paresis (cannot sit with legs under body, walk in a paddling motion with legs behind) |
| 4 | Paralysis (cannot move back legs, drags legs when trying to walk) |
| 5 | Quadriplegia (paralysis in front legs or walking in a circular pattern, may have head tilt) |
| 6 | Moribund (completely paralyzed, cannot reach food or water, sacrifice animal) |

Example 17

TACI-FC and the CIA model for Rheumatoid Arthritis

Male DBA/1J mice (Jackson Labs), eight to twelve weeks old, were divided into groups, 5 mice/group, and given two subcutaneous injections of 50-100 µl of 1 mg/ml collagen (chick), 3 weeks apart. One control did not receive collagen injections. The first injection was formulated in Complete Freund's Adjuvant and the second injection was formulated in Incomplete Freund's Adjuvant. TACI-Fc, a control protein, human IgFc, or PBS (vehicle) was administered prophylactically beginning 7 days prior to the second injection (day -7). All dosing was done at 100 µg, given 3 times a week as a 200 □l intraperitoneal (IP) injection and were continued for 4 weeks.

The animals develop antibodies to the foreign collagen, and in this mouse strain, cross-reactivity to their own native joint cartilage is known to occur. The antibody deposition produces localized joint inflammation and joint destruction very similar to human rheumatoid arthritis. The disease occurrence and severity have been closely correlated with anti-collagen antibody titer levels. Symptoms usually appear within 2-3 weeks of the second injection, but may range from 1-6 weeks.

Extent of disease was evaluated in each paw by using a caliper to measure paw thickness and assigning a clinical score (0-3) to each paw.

| Clinical Score | |
| --- | --- |
| 0 | Normal |
| 1 | Toe(s) inflamed |
| 2 | Mild paw inflammation |
| 3 | Moderate paw inflammation |
| 4 | Severe paw inflammation |

In this study, an animal was said to have "established disease" once a paw maintains a score of 2 or more for one day. Animals were euthanized after having established disease for a set period of time, usually 7 days. Study events were typically defined relative to Day 0, which was defined as the day of the second collagen collection. Paws were collected for histology or mRNA analysis, and serum was collected for immunoglobulin and cytokine assays.

When TACI-Fc was administered prophylactically, there was a marked onset of disease. While the control protein or vehicle groups averaged 50% disease incidence by day 6, the TACI-Fc group averaged 50% incidence by day 15. There was a pronounced reduction in disease severity as shown by both a lower incidence of established disease in the TACI-Fc treated groups as compared to all controls, and a longer time for established disease to occur in the TACI-Fc group.

A second prophylactic study corroborated these results. As described above, TACI-Fc, control protein human Ig-Fc or PBS (vehicle) were administered as a therapeutic, beginning 7 days following the second collagen injection (day +7). All dosing was again at 100 □g given 3 times a week as a 200 µl IP injection, and was continued for 4 weeks. Animals in all groups developed disease at the same rate, but disease severity was greatly reduced in the TACI-Fc-treated animals. This was evidenced by a marked reduction in their incidence of "established disease" as described above. By day 38 the therapeutically treated TACI-Fc group had an incidence rate of just 58% for established disease, as compared to 95% or 100% for the control groups (control protein and vehicle, respectively). The therapeutically treated TACI-Fc group also compares well to the prophylactically-treated TACI-Fc groups as described above, which had a slightly better incidence rate of 50%. This is especially noteworthy given that the therapeutically treated TACI-Fc groups already had a 10% incidence of established disease prior to initiating dosing on day 7.

Serum samples were collected from prophylactically treated and therapeutically treated mice on day -3, day 14 after second collagen injection and day 28 (from therapeutically treated mice only) to determine collagen levels by ELISA.

One hundred µl collagen (Chondrex Redmond, Wash.) was diluted in 10 ml diluent (1 ml 10× buffer (Chondrex), 9 ml water) and microtiter plates (Nunc AS, Roskilde, Denmark) were coated with collagen at 100 µl/well and incubated overnight at 4° C., then washed with ELISA C buffer. The plates were then blocked (200 µl/well) with SuperBlock (Pierce, Rockford, Ill.) at room temperature for 5 minutes, then washed with ELISA C.

Samples were diluted in ELISA B (1% bovine serum albumin, ELISA C), making serial 5 fold dilutions from 1:5000 to 1:625,000 and plated in triplicate at 100 µl/well. The plates were incubated overnight at 4° C. or for 2 hours at room temperature, followed by washing with ELISA C.

Goat anti-mouse Ig-HRP (Zymed, South San Francisco, Calif.) was diluted 1:2000 in ELISA B and plated at 100

µl/well. The plates were incubated at room temperature for 90 minutes then washed with ELISA C.

The plates were developed by plating OPD (1 OPD tablet (Sigma Chemical Co., St. Louis, Mo.), 10 ml Novo D, 10 µl $H_2O_2$) at 100 µl/well. Development was stopped with 1N $H_2SO_4$ at 100 µl/well and the plates were read at an OD of 490 nm.

Figure 9A:
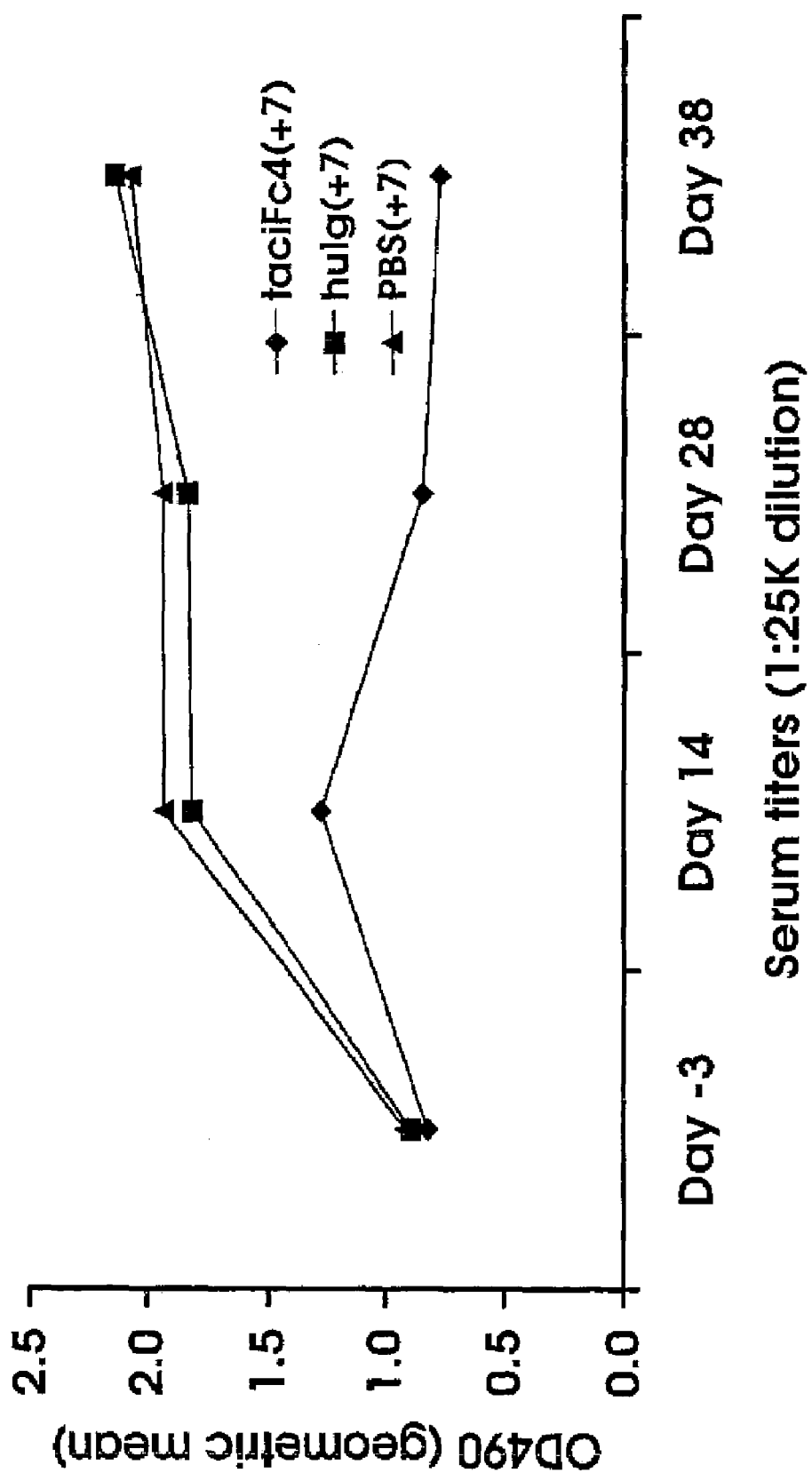

FIG. 9A shows that in TACI-Fc treated mice the level of anti-collagen antibodies is reduced 5-7 days after treatment when compared to control mice, and the level of anti-collagen antibodies continues to decrease with further TACI-Fc treatments.

FIG. 9B shows a drop in collagen antibodies 5 days after the initial collagen treatment in all mice treated. Following the second collagen treatment those mice treated with TACI-Fc show a continued decrease in anti-collagen antibodies until sacrifice, while the levels of anti-collagen antibodies in control mice increase with time.

Example 18

Neutralizing TACI Antibodies

Polyclonal anti-peptide antibodies were prepared by immunizing 2 female New Zealand white rabbits with the peptide, huztnf4-1 SAGIAKLEEGPELQLAIPRE (SEQ ID NO:59) or huztnf4-2 SFKRGSALEEKENKELVKET (SEQ ID NO:60). The peptides were synthesized using an Applied Biosystems Model 431A peptide synthesizer (Applied Biosystems, Inc., Foster City, Calif.) according to manufacturer's instructions. The peptides were then conjugated to the carrier protein keyhole limpet hemocyanin (KLH) with maleimide-activation. The rabbits were each given an initial intraperitoneal (ip) injection of 200 µg of peptide in Complete Freund's Adjuvant followed by booster ip injections of 100 µg peptide in Incomplete Freund's Adjuvant every three weeks. Seven to ten days after the administration of the second booster injection (3 total injections), the animals were bled and the serum was collected. The animals were then boosted and bled every three weeks.

The ztnf4 peptide-specific rabbit seras were characterized by an ELISA titer check using 1 µg/ml of the peptides used to make the antibody (SEQ ID NOs:59 and 60) as an antibody target. The 2 rabbit seras to the huztnf4-1 peptide (SEQ ID NO:59) have titer to their specific peptide at a dilution of 1:1E5 (1:100000). The 2 rabbit seras to the huztnf4-2 peptide (SEQ ID NO:60) had titer to their specific peptide at a dilution of 1:5E6 and to recombinant full-length proteins (N-terminal FLAG-tagged ztnf4 made in baculovirus (huztnf4s-NF-Bv) and C-terminally FLAG-tagged ztnf4 made in BHK cells) at a dilution of 1:5E6.

The ztnf4 peptide-specific polyclonal antibodies were affinity purified from the rabbit serum using CNBR-SEPHAROSE 4B protein columns (Pharmacia LKB) that were prepared using 10 mgs of the specific peptides (SEQ. ID. NOs.59 or 60) per gram CNBr-SEPHAROSE, followed by 20× dialysis in PBS overnight. Ztnf4-specific antibodies were characterized by an ELISA titer check using 1 µg/ml of the appropriate peptide antigen or recombinant full-length protein (huztnf4s-NF-Bv) as antibody targets. The lower limit of detection (LLD) of the rabbit anti-huztnf4-1 affinity purified antibody on its specific antigen (huztnf4-1 peptide, SEQ ID NO:59) is a dilution of 5 ng/ml. The lower limit of detection (LLD) of the rabbit anti-huztnf4-2 affinity purified antibody on its specific antigen (huztnf4-2 peptide, SEQ ID NO:60) is a dilution of 0.5 ng/ml. The lower limit of detection (LLD) of the rabbit anti-huztnf4-2 affinity purified antibody on the recombinant protein huztnf4s-NF-Bv is a dilution of 5 ng/ml.

Monoclonal antibodies were generated and selected for inhibition of inhibition of biotin-labeled soluble ztnf4. None of the TACI monoclonal antibodies (248.14, 248.23, 248.24, or 246.3) block ztnf4 binding on BCMA. Monoclonal 248.23 reduces binding of 10 ng/ml ztnf4-biotin to about 50% when conditioned media is diluted to 1:243 and reduces binding to about 2× in undiluted media. Monoclonal 246.3 reduces binding of 10 ng/ml ztnf4-biotin to about 50% between a 1:243 and 1:181 dilution of conditioned media and reduces binding 5× in undiluted media.

Example 19

Ztnf4 Levels in SLE Patients

Levels of ztnf4 in the SLE patients, relative to normal individuals, was determined using an ORIGIN ASSAY as described above. A standard curve prepared from soluble, human ztnf4 at 10 ng/ml, 1 ng/ml, 0.1 ng/ml, 0.01 ng/ml and 0 ng/ml was prepared in ORIGIN buffer (Igen). All patient samples were run in triplicate, 25 µl of final volume. The standards and samples were incubated at room temperature for 2 hours with a capture antibody, biotinylated rabbit anti-human ztnf4-NF BV polyclonal antibody, diluted to 1 µg/ml in Origin Assay Buffer (IGEN) and a detection antibody, ruthenylated rabbit anti-human ztnf4-NF BV polyclonal antibody, diluted to 1 µg/ml in Origin Assay Buffer (IGEN). Following the incubation the samples were vortexed and 0.4 mg/ml streptavidin Dynabeads (Dynal) were added to each of the standards and samples at 50 µl/tube and incubated for 30 minutes at room temperature. Samples were then vortexed and using an Origin 1.5 Analyzer (Igen) according to manufacturer's instructions.

Figure 10:
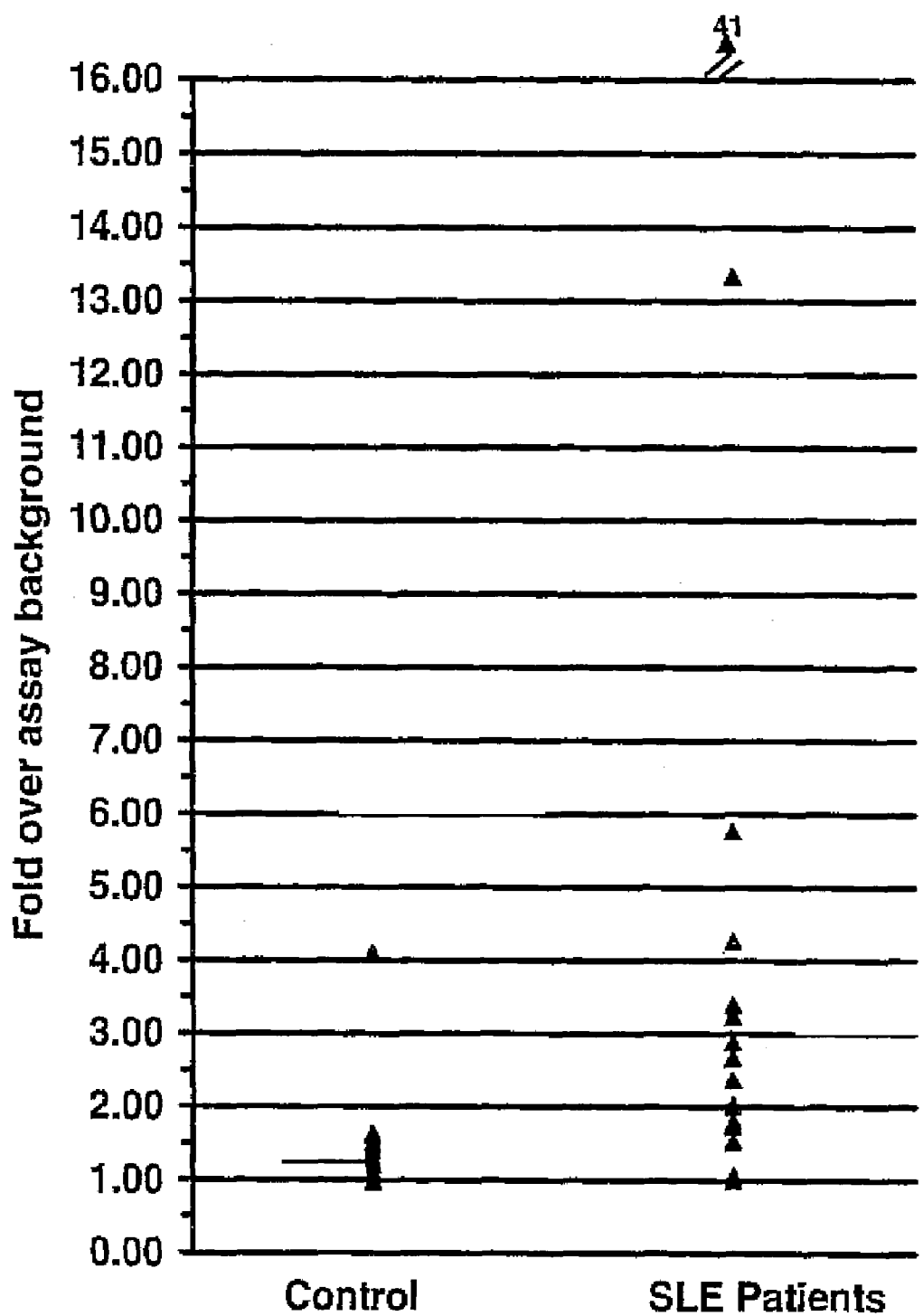
FIG. 10 shows levels of ztnf4 in SLE patients.

Elevated levels of ztnf4 were seen in the serum of patients diagnosed with SLE as compared with normal control serum donors (FIG. 10). Twenty eight normal control samples were tested and samples from 20 patients diagnosed with SLE. The data is reported as fold increase of ztnf4 levels in the patient or control samples as compared to an arbitrary human reference serum sample. The average of the 28 control samples was 1.36 fold over the human reference sample and the average of the 20 SLE patient samples was 4.92. Seven out of the 20 SLE patients had ztnf4 levels that were two fold over the average of the control samples, whereas there was only one control individual that had a greater than two fold level over the control average.

Example 20

TACI-Ig and EAMG Mouse Model

The effect of TACI-Ig is determined by administering TACI-Ig during ongoing clinical myasthenia gravis (MG) in B6 mice. One hundred B6 mice are immunized with 20 µg acetylcholine receptor (AChR) in complete Freunds Adjuvant (CFA) on days 0 and 30. Approximately 40-60% of mice will develop moderate (grade 2) to severe (grade 3) clinical MG after the boost with AChR. Mice with grade 2 and 3 clinical disease are divided into three groups (with equal grades of weakness) and weighed (mice with weakness also lose weight, since they have difficulty in consuming food and water) and bled for serum (for pre-treatment anti-AChR antibody and isotype level). Group A is injected I.P with PBS, group B is injected I.P with murine IgG2a-FC as a control protein (100 µg), and group C is injected with 100 µg of murine TACI-IgG2a-FC three times a week for 4 weeks. Mice are screened for clinical muscle weakness twice a week and weighed and bled for serum 15 and 30 days after the commencement of treatment. Whole blood is collected on day 15 to determine T/B cell ratio by FACS analysis using markers B220 and CD5. Surviving mice are killed 30-45 days after the initiation of treatment, and their carcasses are frozen for later extraction of muscle AChR (Wu et al. *Protocols in Immunology*. Vol. 3, Eds. Coligen, Kruisbeak, Margulies, Shevach, and Strober. John Wiley and Sons, New York, p. 15.8.1, 1997) to determine the loss of muscle AChR, the primary pathology in MG.

Dose Response Study

Serum antibodies to mouse muscle AChR is determined by an established radioimmunoassay, and anti-AChR antibody isotypes (IgM, IgG1, IgG2b and IgG2c) is measured by ELISA. Such methods are known, see for example, Wu et al. ibid. The effect of TACI-Ig on ongoing clinical MG, anti-AChR antibody and isotype level, and muscle AChR loss is determined.

Approximately 100 mice will each be immunized with 20 μg AChR in CFA on day 0 and 30. Mice with clinical MG are divided into 4 groups. Group A is injected I.P with 100 μg control FC (murine IgG2a-FC), group B is injected with 20 μg control FC (murine IgG2a-FC), and group C is injected 100 μg murine TACI-IgG2a-FC, and group D is injected with 20 μg murine TACI-IgG2a-FC three times a week for 4 weeks. Mice are weighed and bled for serum before and 15 and 30 days after the start of the treatment. Serum is tested for anti-AChR antibody and isotypes as above. Muscle AChR loss will also be measured.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polypeptide consisting of an amino acid sequence selected from the group consisting of:
   a) amino acid residues 1-37 of SEQ ID NO: 8;
   b) amino acid residues 1-48 of SEQ ID NO: 8;
   c) amino acid residues 8-37 of SEQ ID NO: 8;
   d) amino acid residues 8-48 of SEQ ID NO: 8;
   e) amino acid residues 41-88 of SEQ ID NO: 8;
   f) amino acid residues 8-88 of SEQ ID NO: 8;
   g) amino acid residues 1-150 of SEQ ID NO 8; and
   h) any one of amino acid sequences a) to g) further comprising a secretory signal sequence.

* * * * *

SEQUENCE LISTING

```
<160> NUMBER OF SEQ ID NOS: 60

<210> SEQ ID NO 1
<211> LENGTH: 1192
<212> TYPE: DNA
<213> ORGANISM: Homo sapiens
<220> FEATURE:
<221> NAME/KEY: CDS
<222> LOCATION: (6)...(746)

<400> SEQUENCE: 1 gagta atg agt ggc ctg ggc cgg agc agg cga ggt ggc cgg agc cgt gtg        50
      Met Ser Gly Leu Gly Arg Ser Arg Arg Gly Gly Arg Ser Arg Val
      1               5                  10                  15 gac cag gag gag cgc tgg tca ctc agc tgc cgc aag gag caa ggc aag          98
Asp Gln Glu Glu Arg Trp Ser Leu Ser Cys Arg Lys Glu Gln Gly Lys
                 20                  25                  30 ttc tat gac cat ctc ctg agg gac tgc atc agc tgt gcc tcc atc tgt         146
Phe Tyr Asp His Leu Leu Arg Asp Cys Ile Ser Cys Ala Ser Ile Cys
             35                  40                  45 gga cag cac cct aag caa tgt gca tac ttc tgt gag aac aag ctc agg         194
Gly Gln His Pro Lys Gln Cys Ala Tyr Phe Cys Glu Asn Lys Leu Arg
         50                  55                  60 agc cca gtg aac ctt cca cca gag ctc agg aga cag cgg agt gga gaa         242
Ser Pro Val Asn Leu Pro Pro Glu Leu Arg Arg Gln Arg Ser Gly Glu
65                  70                  75 gtt gaa aac aat tca gac aac tcg gga agg tac caa gga ttg gag cac         290
Val Glu Asn Asn Ser Asp Asn Ser Gly Arg Tyr Gln Gly Leu Glu His
80                  85                  90                  95 aga ggc tca gaa gca agt cca gct ctc ccg ggg ctg aag ctg agt gca         338
Arg Gly Ser Glu Ala Ser Pro Ala Leu Pro Gly Leu Lys Leu Ser Ala
                100                 105                 110 gat cag gtg gcc ctg gtc tac agc acg ctg ggc ctc tgc ctg tgt gcc         386
Asp Gln Val Ala Leu Val Tyr Ser Thr Leu Gly Leu Cys Leu Cys Ala
            115                 120                 125 gtc ctc tgc tgc ttc ctg gtg gcg gtg gcc tgc ttc ctc aag aag agg         434
Val Leu Cys Cys Phe Leu Val Ala Val Ala Cys Phe Leu Lys Lys Arg
        130                 135                 140 ggg gat ccc tgc tcc tgc cag ccc cgc tca agg ccc cgt caa agt ccg         482
```

-continued

```
Gly Asp Pro Cys Ser Cys Gln Pro Arg Ser Arg Pro Arg Gln Ser Pro
145                 150                 155 gcc aag tct tcc cag gat cac gcg atg gaa gcc ggc agc cct gtg agc     530
Ala Lys Ser Ser Gln Asp His Ala Met Glu Ala Gly Ser Pro Val Ser
160                 165                 170                 175 aca tcc ccc gag cca gtg gag acc tgc agc ttc tgc ttc cct gag tgc     578
Thr Ser Pro Glu Pro Val Glu Thr Cys Ser Phe Cys Phe Pro Glu Cys
                180                 185                 190 agg gcg ccc acg cag gag agc gca gtc acg cct ggg acc ccc gac ccc     626
Arg Ala Pro Thr Gln Glu Ser Ala Val Thr Pro Gly Thr Pro Asp Pro
            195                 200                 205 act tgt gct gga agg tgg ggg tgc cac acc agg acc aca gtc ctg cag     674
Thr Cys Ala Gly Arg Trp Gly Cys His Thr Arg Thr Thr Val Leu Gln
        210                 215                 220 cct tgc cca cac atc cca gac agt ggc ctt ggc att gtg tgt gtg cct     722
Pro Cys Pro His Ile Pro Asp Ser Gly Leu Gly Ile Val Cys Val Pro
    225                 230                 235 gcc cag gag ggg ggc cca ggt gca taaatggggg tcagggaggg aaaggaggag    776
Ala Gln Glu Gly Gly Pro Gly Ala
240                 245 ggagagagat ggagaggagg ggagagagaa agagaggtgg ggagagggga gagagatatg    836
aggagagaga gacagaggag gcagagaggg agagaaacag aggagacaga gagggagaga    896
gagacagagg gagagagaga cagggggaa gagaggcaga gagggaaaga ggcagagaag    956
gaaagaggca gagagggaga gaggcagaga gggagagagg cagagagaca gagagggaga   1016
gagggacaga gagagataga gcaggaggtc ggggcactct gagtcccagt tcccagtgca   1076
gctgtaggtc gtcatcacct aaccacacgt gcaataaagt cctcgtgcct gctgctcaca   1136
gcccccgaga gccctcctc ctggagaata aaccctttgg cagctgccct tcctca        1192
```

<210> SEQ ID NO 2
<211> LENGTH: 247
<212> TYPE: PRT
<213> ORGANISM: Homo sapiens

<400> SEQUENCE: 2

```
Met Ser Gly Leu Gly Arg Ser Arg Gly Gly Arg Ser Arg Val Asp
1               5                   10                  15

Gln Glu Glu Arg Trp Ser Leu Ser Cys Arg Lys Glu Gln Gly Lys Phe
                20                  25                  30

Tyr Asp His Leu Leu Arg Asp Cys Ile Ser Cys Ala Ser Ile Cys Gly
            35                  40                  45

Gln His Pro Lys Gln Cys Ala Tyr Phe Cys Glu Asn Lys Leu Arg Ser
        50                  55                  60

Pro Val Asn Leu Pro Pro Glu Leu Arg Arg Gln Arg Ser Gly Glu Val
65                  70                  75                  80

Glu Asn Asn Ser Asp Asn Ser Gly Arg Tyr Gln Gly Leu Glu His Arg
                85                  90                  95

Gly Ser Glu Ala Ser Pro Ala Leu Pro Gly Leu Lys Leu Ser Ala Asp
            100                 105                 110

Gln Val Ala Leu Val Tyr Ser Thr Leu Gly Leu Cys Leu Cys Ala Val
        115                 120                 125

Leu Cys Cys Phe Leu Val Ala Val Ala Cys Phe Leu Lys Lys Arg Gly
    130                 135                 140

Asp Pro Cys Ser Cys Gln Pro Arg Ser Arg Pro Arg Gln Ser Pro Ala
145                 150                 155                 160
```

```
Lys Ser Ser Gln Asp His Ala Met Glu Ala Gly Ser Pro Val Ser Thr
            165                 170                 175

Ser Pro Glu Pro Val Glu Thr Cys Ser Phe Cys Phe Pro Glu Cys Arg
        180                 185                 190

Ala Pro Thr Gln Glu Ser Ala Val Thr Pro Gly Thr Pro Asp Pro Thr
    195                 200                 205

Cys Ala Gly Arg Trp Gly Cys His Thr Arg Thr Thr Val Leu Gln Pro
210                 215                 220

Cys Pro His Ile Pro Asp Ser Gly Leu Gly Ile Val Cys Val Pro Ala
225                 230                 235                 240

Gln Glu Gly Gly Pro Gly Ala
                245

<210> SEQ ID NO 3
<211> LENGTH: 360
<212> TYPE: DNA
<213> ORGANISM: Homo sapiens
<220> FEATURE:
<221> NAME/KEY: CDS
<222> LOCATION: (1)...(360)

<400> SEQUENCE: 3 atg agt ggc ctg ggc cgg agc agg cga ggt ggc cgg agc cgt gtg gac      48
Met Ser Gly Leu Gly Arg Ser Arg Arg Gly Gly Arg Ser Arg Val Asp
1               5                   10                  15 cag gag gag cgc tgg tca ctc agc tgc cgc aag gag caa ggc aag ttc      96
Gln Glu Glu Arg Trp Ser Leu Ser Cys Arg Lys Glu Gln Gly Lys Phe
            20                  25                  30 tat gac cat ctc ctg agg gac tgc atc agc tgt gcc tcc atc tgt gga     144
Tyr Asp His Leu Leu Arg Asp Cys Ile Ser Cys Ala Ser Ile Cys Gly
        35                  40                  45 cag cac cct aag caa tgt gca tac ttc tgt gag aac aag ctc agg agc     192
Gln His Pro Lys Gln Cys Ala Tyr Phe Cys Glu Asn Lys Leu Arg Ser
    50                  55                  60 cca gtg aac ctt cca cca gag ctc agg aga cag cgg agt gga gaa gtt     240
Pro Val Asn Leu Pro Pro Glu Leu Arg Arg Gln Arg Ser Gly Glu Val
65                  70                  75                  80 gaa aac aat tca gac aac tcg gga agg tac caa gga ttg gag cac aga     288
Glu Asn Asn Ser Asp Asn Ser Gly Arg Tyr Gln Gly Leu Glu His Arg
                85                  90                  95 ggc tca gaa gca agt cca gct ctc ccg ggg ctg aag ctg agt gca gat     336
Gly Ser Glu Ala Ser Pro Ala Leu Pro Gly Leu Lys Leu Ser Ala Asp
            100                 105                 110 cag gtg gcc ctg gtc tac agc acg                                     360
Gln Val Ala Leu Val Tyr Ser Thr
        115                 120

<210> SEQ ID NO 4
<211> LENGTH: 120
<212> TYPE: PRT
<213> ORGANISM: Homo sapiens

<400> SEQUENCE: 4

Met Ser Gly Leu Gly Arg Ser Arg Arg Gly Gly Arg Ser Arg Val Asp
1               5                   10                  15

Gln Glu Glu Arg Trp Ser Leu Ser Cys Arg Lys Glu Gln Gly Lys Phe
            20                  25                  30

Tyr Asp His Leu Leu Arg Asp Cys Ile Ser Cys Ala Ser Ile Cys Gly
        35                  40                  45

Gln His Pro Lys Gln Cys Ala Tyr Phe Cys Glu Asn Lys Leu Arg Ser
```

-continued

```
                        50                  55                  60
Pro Val Asn Leu Pro Pro Glu Leu Arg Arg Gln Arg Ser Gly Glu Val
 65                  70                  75                  80

Glu Asn Asn Ser Asp Asn Ser Gly Arg Tyr Gln Gly Leu Glu His Arg
                 85                  90                  95

Gly Ser Glu Ala Ser Pro Ala Leu Pro Gly Leu Lys Leu Ser Ala Asp
            100                 105                 110

Gln Val Ala Leu Val Tyr Ser Thr
            115                 120

<210> SEQ ID NO 5
<211> LENGTH: 1377
<212> TYPE: DNA
<213> ORGANISM: Homo sapiens
<220> FEATURE:
<221> NAME/KEY: CDS
<222> LOCATION: (14)...(895)

<400> SEQUENCE: 5
agcatcctga gta atg agt ggc ctg ggc cgg agc agg cga ggt ggc cgg         49
            Met Ser Gly Leu Gly Arg Ser Arg Arg Gly Gly Arg
             1               5                  10 agc cgt gtg gac cag gag gag cgc ttt cca cag ggc ctg tgg acg ggg        97
Ser Arg Val Asp Gln Glu Glu Arg Phe Pro Gln Gly Leu Trp Thr Gly
        15                  20                  25 gtg gct atg aga tcc tgc ccc gaa gag cag tac tgg gat cct ctg ctg       145
Val Ala Met Arg Ser Cys Pro Glu Glu Gln Tyr Trp Asp Pro Leu Leu
 30                  35                  40 ggt acc tgc atg tcc tgc aaa acc att tgc aac cat cag agc cag cgc       193
Gly Thr Cys Met Ser Cys Lys Thr Ile Cys Asn His Gln Ser Gln Arg
 45                  50                  55                  60 acc tgt gca gcc ttc tgc agg tca ctc agc tgc cgc aag gag caa ggc       241
Thr Cys Ala Ala Phe Cys Arg Ser Leu Ser Cys Arg Lys Glu Gln Gly
                 65                  70                  75 aag ttc tat gac cat ctc ctg agg gac tgc atc agc tgt gcc tcc atc       289
Lys Phe Tyr Asp His Leu Leu Arg Asp Cys Ile Ser Cys Ala Ser Ile
             80                  85                  90 tgt gga cag cac cct aag caa tgt gca tac ttc tgt gag aac aag ctc       337
Cys Gly Gln His Pro Lys Gln Cys Ala Tyr Phe Cys Glu Asn Lys Leu
         95                 100                 105 agg agc cca gtg aac ctt cca cca gag ctc agg aga cag cgg agt gga       385
Arg Ser Pro Val Asn Leu Pro Pro Glu Leu Arg Arg Gln Arg Ser Gly
    110                 115                 120 gaa gtt gaa aac aat tca gac aac tcg gga agg tac caa gga ttg gag       433
Glu Val Glu Asn Asn Ser Asp Asn Ser Gly Arg Tyr Gln Gly Leu Glu
125                 130                 135                 140 cac aga ggc tca gaa gca agt cca gct ctc ccg ggg ctg aag ctg agt       481
His Arg Gly Ser Glu Ala Ser Pro Ala Leu Pro Gly Leu Lys Leu Ser
                145                 150                 155 gca gat cag gtg gcc ctg gtc tac agc acg ctg ggg ctc tgc ctg tgt       529
Ala Asp Gln Val Ala Leu Val Tyr Ser Thr Leu Gly Leu Cys Leu Cys
            160                 165                 170 gcc gtc ctc tgc tgc ttc ctg gtg gcg gtg gcc tgc ttc ctc aag aag       577
Ala Val Leu Cys Cys Phe Leu Val Ala Val Ala Cys Phe Leu Lys Lys
        175                 180                 185 agg ggg gat ccc tgc tcc tgc cag ccc cgc tca agg ccc cgt caa agt       625
Arg Gly Asp Pro Cys Ser Cys Gln Pro Arg Ser Arg Pro Arg Gln Ser
    190                 195                 200 ccg gcc aag tct tcc cag gat cac gcg atg gaa gcc ggc agc cct gtg       673
Pro Ala Lys Ser Ser Gln Asp His Ala Met Glu Ala Gly Ser Pro Val
```

```
                205                 210                 215                 220
agc aca tcc ccc gag cca gtg gag acc tgc agc ttc tgc ttc cct gag           721
Ser Thr Ser Pro Glu Pro Val Glu Thr Cys Ser Phe Cys Phe Pro Glu
                    225                 230                 235 tgc agg gcg ccc acg cag gag agc gca gtc acg cct ggg acc ccc gac           769
Cys Arg Ala Pro Thr Gln Glu Ser Ala Val Thr Pro Gly Thr Pro Asp
            240                 245                 250 ccc act tgt gct gga agg tgg ggg tgc cac acc agg acc aca gtc ctg           817
Pro Thr Cys Ala Gly Arg Trp Gly Cys His Thr Arg Thr Thr Val Leu
        255                 260                 265 cag cct tgc cca cac atc cca gac agt ggc ctt ggc att gtg tgt gtg           865
Gln Pro Cys Pro His Ile Pro Asp Ser Gly Leu Gly Ile Val Cys Val
    270                 275                 280 cct gcc cag gag ggg ggc cca ggt gca taa atggggtca gggagggaaa              915
Pro Ala Gln Glu Gly Gly Pro Gly Ala *
285                 290 ggaggaggga gagagatgga gaggagggga gagagaaaga gaggtgggga gaggggagag         975
agatatgagg agagagagac agaggaggca gaaagggaga gaaacagagg agacagagag        1035
ggagagagag acagagggag agagagacag aggggaagag aggcagagag ggaaagaggc        1095
agagaaggaa agagacaggc agagaaggag agaggcagag agggagagag gcagagaggg        1155
agagaggcag agagacagag agggagagag ggacagagag agatagagca ggaggtcggg        1215
gcactctgag tcccagttcc cagtgcagct gtaggtcgtc atcacctaac cacacgtgca        1275
ataaagtcct cgtgcctgct gctcacagcc cccgagagcc cctcctcctg gagaataaaa        1335
cctttggcag ctgcccttcc tcaaaaaaaa aaaaaaaaa aa                            1377

<210> SEQ ID NO 6
<211> LENGTH: 293
<212> TYPE: PRT
<213> ORGANISM: Homo sapiens

<400> SEQUENCE: 6

Met Ser Gly Leu Gly Arg Ser Arg Gly Gly Arg Ser Arg Val Asp
 1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175
```

```
Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 7
<211> LENGTH: 995
<212> TYPE: DNA
<213> ORGANISM: Homo sapiens
<220> FEATURE:
<221> NAME/KEY: CDS
<222> LOCATION: (219)...(773)

<400> SEQUENCE: 7
aagactcaaa cttagaaact tgaattagat gtggtattca aatccttacg tgccgcgaag      60
acacagacag cccccgtaag aacccacgaa gcaggcgaag ttcattgttc tcaacattct     120
agctgctctt gctgcatttg ctctggaatt cttgtagaga tattacttgt ccttccaggc     180
tgttctttct gtagctccct tgttttcttt tgtgatc atg ttg cag atg gct ggg     236
                                        Met Leu Gln Met Ala Gly
                                          1               5 cag tgc tcc caa aat gaa tat ttt gac agt ttg ttg cat gct tgc ata     284
Gln Cys Ser Gln Asn Glu Tyr Phe Asp Ser Leu Leu His Ala Cys Ile
             10                  15                  20 cct tgt caa ctt cga tgt tct tct aat act cct cct cta aca tgt cag     332
Pro Cys Gln Leu Arg Cys Ser Ser Asn Thr Pro Pro Leu Thr Cys Gln
         25                  30                  35 cgt tat tgt aat gca agt gtg acc aat tca gtg aaa gga acg aat gcg     380
Arg Tyr Cys Asn Ala Ser Val Thr Asn Ser Val Lys Gly Thr Asn Ala
     40                  45                  50 att ctc tgg acc tgt ttg gga ctg agc tta ata att tct ttg gca gtt     428
Ile Leu Trp Thr Cys Leu Gly Leu Ser Leu Ile Ile Ser Leu Ala Val
 55                  60                  65                  70 ttc gtg cta atg ttt ttg cta agg aag ata agc tct gaa cca tta aag     476
Phe Val Leu Met Phe Leu Leu Arg Lys Ile Ser Ser Glu Pro Leu Lys
                 75                  80                  85 gac gag ttt aaa aac aca gga tca ggt ctc ctg ggc atg gct aac att     524
Asp Glu Phe Lys Asn Thr Gly Ser Gly Leu Leu Gly Met Ala Asn Ile
             90                  95                 100 gac ctg gaa aag agc agg act ggt gat gaa att att ctt ccg aga ggc     572
Asp Leu Glu Lys Ser Arg Thr Gly Asp Glu Ile Ile Leu Pro Arg Gly
        105                 110                 115 ctc gag tac acg gtg gaa gaa tgc acc tgt gaa gac tgc atc aag agc     620
Leu Glu Tyr Thr Val Glu Glu Cys Thr Cys Glu Asp Cys Ile Lys Ser
    120                 125                 130 aaa ccg aag gtc gac tct gac cat tgc ttt cca ctc cca gct atg gag     668
Lys Pro Lys Val Asp Ser Asp His Cys Phe Pro Leu Pro Ala Met Glu
```

```
                    135                 140                 145                 150
gaa ggc gca acc att ctt gtc acc acg aaa acg aat gac tat tgc aag                 716
Glu Gly Ala Thr Ile Leu Val Thr Thr Lys Thr Asn Asp Tyr Cys Lys
                    155                 160                 165 agc ctg cca gct gct ttg agt gct acg gag ata gag aaa tca att tct                 764
Ser Leu Pro Ala Ala Leu Ser Ala Thr Glu Ile Glu Lys Ser Ile Ser
                    170                 175                 180 gct agg taa ttaaccattt cgactcgagc agtgccactt taaaatctt                           813
Ala Arg  * ttgtcagaat agatgatgtg tcagatctct ttaggatgac tgtattttc agttgccgat                873 acagcttttt gtcctctaac tgtggaaact ctttatgtta gatatatttc tctaggttac               933
tgttgggagc ttaatggtag aaacttcctt ggtttcatga ttaaagtctt ttttttttcct              993 ga                                                                              995

<210> SEQ ID NO 8
<211> LENGTH: 184
<212> TYPE: PRT
<213> ORGANISM: Homo sapiens

<400> SEQUENCE: 8

Met Leu Gln Met Ala Gly Gln Cys Ser Gln Asn Glu Tyr Phe Asp Ser
  1               5                  10                  15

Leu Leu His Ala Cys Ile Pro Cys Gln Leu Arg Cys Ser Ser Asn Thr
                 20                  25                  30

Pro Pro Leu Thr Cys Gln Arg Tyr Cys Asn Ala Ser Val Thr Asn Ser
             35                  40                  45

Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
 65                  70                  75                  80

Ser Ser Glu Pro Leu Lys Asp Glu Phe Lys Asn Thr Gly Ser Gly Leu
                 85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 9
<211> LENGTH: 245
<212> TYPE: PRT
<213> ORGANISM: Homo sapiens

<400> SEQUENCE: 9

Gly Arg Ser Arg Arg Gly Gly Arg Ser Arg Val Asp Gln Glu Glu Arg
  1               5                  10                  15

Phe Pro Gln Gly Leu Trp Thr Gly Val Ala Met Arg Ser Cys Pro Glu
                 20                  25                  30
```

```
Glu Gln Tyr Trp Asp Pro Leu Leu Gly Thr Cys Met Ser Cys Lys Thr
                35                  40                  45

Ile Cys Asn His Gln Ser Gln Arg Thr Cys Ala Ala Phe Cys Arg Ser
 50                  55                  60

Leu Ser Cys Arg Lys Glu Gln Gly Lys Phe Tyr Asp His Leu Leu Arg
 65                  70                  75                  80

Asp Cys Ile Ser Cys Ala Ser Ile Cys Gly Gln His Pro Lys Gln Cys
                 85                  90                  95

Ala Tyr Phe Cys Glu Asn Lys Leu Arg Ser Pro Val Asn Leu Pro Pro
                100                 105                 110

Glu Leu Arg Arg Gln Arg Ser Gly Glu Val Glu Asn Asn Ser Asp Asn
                115                 120                 125

Ser Gly Arg Tyr Gln Gly Leu Glu His Arg Gly Ser Glu Ala Ser Pro
130                 135                 140

Ala Leu Pro Gly Leu Lys Leu Ser Ala Asp Gln Val Ala Leu Val Tyr
145                 150                 155                 160

Ser Thr Leu Gly Leu Cys Leu Cys Ala Val Leu Cys Cys Phe Leu Val
                165                 170                 175

Ala Val Ala Cys Phe Leu Lys Lys Arg Gly Asp Pro Cys Ser Cys Gln
                180                 185                 190

Pro Arg Ser Arg Pro Arg Gln Ser Pro Ala Lys Ser Ser Gln Asp His
                195                 200                 205

Ala Met Glu Ala Gly Ser Pro Val Ser Thr Ser Pro Glu Pro Val Glu
                210                 215                 220

Thr Cys Ser Phe Cys Phe Pro Glu Cys Arg Ala Pro Thr Gln Glu Ser
225                 230                 235                 240

Ala Val Thr Pro Gly
                245

<210> SEQ ID NO 10
<211> LENGTH: 40
<212> TYPE: PRT
<213> ORGANISM: Artificial Sequence
<220> FEATURE:
<223> OTHER INFORMATION: Motif describing the cysteine-rich
      pseudo-repeat domain
<220> FEATURE:
<221> NAME/KEY: VARIANT
<222> LOCATION: (1)...(2)
<223> OTHER INFORMATION: Each Xaa is independently any amino acid
      residue except cysteine, or absent.
<220> FEATURE:
<221> NAME/KEY: VARIANT
<222> LOCATION: (4)...(4)
<223> OTHER INFORMATION: Xaa is any amino acid residue except cysteine.
<220> FEATURE:
<221> NAME/KEY: VARIANT
<222> LOCATION: (5)...(5)
<223> OTHER INFORMATION: Xaa is slutamine, glutamic acid, or lysine.
<220> FEATURE:
<221> NAME/KEY: VARIANT
<222> LOCATION: (6)...(6)
<223> OTHER INFORMATION: Xaa is glutamine, glutamic acid, lysine,
      asparagine, arginine, aspartic acid, histidine, or
      serine.
<220> FEATURE:
<221> NAME/KEY: VARIANT
<222> LOCATION: (7)...(7)
<223> OTHER INFORMATION: Xaa is glutamine or glutamic acid.
<220> FEATURE:
<221> NAME/KEY: VARIANT
<222> LOCATION: (8)...(9)
<223> OTHER INFORMATION: Each Xaa is independently any amino acid
      residue except cysteine, or absent.
<220> FEATURE:
```

```
<221> NAME/KEY: VARIANT
<222> LOCATION: (10)...(11)
<223> OTHER INFORMATION: Xaa is tyrosine, phenylalanine, or tryptophan.
<220> FEATURE:
<221> NAME/KEY: VARIANT
<222> LOCATION: (13)...(13)
<223> OTHER INFORMATION: Xaa is any amino acid residue except cysteine.
<220> FEATURE:
<221> NAME/KEY: VARIANT
<222> LOCATION: (16)...(17)
<223> OTHER INFORMATION: Each Xaa is independently any amino acid
      residue except cysteine.
<220> FEATURE:
<221> NAME/KEY: VARIANT
<222> LOCATION: (19)...(19)
<223> OTHER INFORMATION: Xaa is isoleucine, methionine, leucine, or
      valine.
<220> FEATURE:
<221> NAME/KEY: VARIANT
<222> LOCATION: (20)...(20)
<223> OTHER INFORMATION: Xaa is any amino acid residue except cysteine.
<220> FEATURE:
<221> NAME/KEY: VARIANT
<222> LOCATION: (22)...(24)
<223> OTHER INFORMATION: Each Xaa is independently any amino acid
      residue except cysteine.
<220> FEATURE:
<221> NAME/KEY: VARIANT
<222> LOCATION: (26)...(31)
<223> OTHER INFORMATION: Each Xaa is independently any amino acid
      residue except cysteine.
<220> FEATURE:
<221> NAME/KEY: VARIANT
<222> LOCATION: (32)...(33)
<223> OTHER INFORMATION: Each Xaa is independently any amino acid
      residue except cysteine, or absent.
<220> FEATURE:
<221> NAME/KEY: VARIANT
<222> LOCATION: (35)...(36)
<223> OTHER INFORMATION: Each Xaa is independently any amino acid
      residue except cysteine.
<220> FEATURE:
<221> NAME/KEY: VARIANT
<222> LOCATION: (37)...(37)
<223> OTHER INFORMATION: Xaa is tyrosine or phenylalanine.
<220> FEATURE:
<221> NAME/KEY: VARIANT
<222> LOCATION: (39)...(40)
<223> OTHER INFORMATION: Each Xaa is independently any amino acid
      residue except cysteine, or absent.

<400> SEQUENCE: 10

Xaa Xaa Cys Xaa Xaa Xaa Xaa Xaa Xaa Xaa Xaa Asp Xaa Leu Leu Xaa
 1               5                   10                  15

Xaa Cys Xaa Xaa Cys Xaa Xaa Xaa Cys Xaa Xaa Xaa Xaa Xaa Xaa Xaa
            20                  25                  30

Xaa Cys Xaa Xaa Xaa Cys Xaa Xaa
        35                  40

<210> SEQ ID NO 11
<211> LENGTH: 360
<212> TYPE: DNA
<213> ORGANISM: Artificial Sequence
<220> FEATURE:
<223> OTHER INFORMATION: Degenerate oligonucleotide sequence encoding
      the polypeptide of SEQ ID NO:4
<220> FEATURE:
<221> NAME/KEY: variation
<222> LOCATION: (1)...(360)
<223> OTHER INFORMATION: Each N is independently A, T, G, or C.

<400> SEQUENCE: 11
atgwsnggny tnggnmgnws nmgnmgnggn ggnmgnwsnm gngtngayca rgargarmgn    60
```

```
tggwsnytnw sntgymgnaa rgarcarggn aarttytayg aycayytnyt nmgngaytgy      120
athwsntgyg cnwsnathtg yggncarcay ccnaarcart gygcntaytt ytgygaraay      180
aarytnmgnw snccngtnaa yytnccnccn garytnmgnm gncarmgnws nggngargtn      240
garaayaayw sngayaayws nggnmgntay

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide ZC19980

<400> SEQUENCE: 15
cgaagagcag tactgggatc ctct                                                24

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide ZC19981

<400> SEQUENCE: 16
gccaaggcca ctgtctggga tgt                                                 23

<210> SEQ ID NO 17
<211> LENGTH: 1149
<212> TYPE: DNA
<213> ORGANISM: Homo sapiens
<220> FEATURE:
<221> NAME/KEY: CDS
<222> LOCATION: (236)...(1027)

<400> SEQUENCE: 17

```
gaattcggca cgaggcagaa aggagaaaat tcaggataac tctcctgagg ggtgagccaa          60
gccctgccat gtagtgcacg caggacatca acaaacacag ataacaggaa atgatccatt         120
ccctgtggtc acttattcta aaggccccaa ccttcaaagt tcaagtagtg atatggatga         180
ctccacagaa agggagcagt cacgccttac ttcttgcctt aagaaagag aagaa atg          238
                                                                    Met
                                                                      1 aaa ctg aag gag tgt gtt tcc atc ctc cca cgg aag gaa agc ccc tct          286
Lys Leu Lys Glu Cys Val Ser Ile Leu Pro Arg Lys Glu Ser Pro Ser
              5                  10                  15 gtc cga tcc tcc aaa gac gga aag ctg ctg gct gca acc ttg ctg ctg          334
Val Arg Ser Ser Lys Asp Gly Lys Leu Leu Ala Ala Thr Leu Leu Leu
         20                  25                  30 gca ctg ctg tct tgc tgc ctc acg gtg gtg tct ttc tac cag gtg gcc          382
Ala Leu Leu Ser Cys Cys Leu Thr Val Val Ser Phe Tyr Gln Val Ala
     35                  40                  45 gcc ctg caa ggg gac ctg gcc agc ctc cgg gca gag ctg cag ggc cac          430
Ala Leu Gln Gly Asp Leu Ala Ser Leu Arg Ala Glu Leu Gln Gly His
 50                  55                  60                  65 cac gcg gag aag ctg cca gca gga gca gga gcc ccc aag gcc ggc ctg          478
His Ala Glu Lys Leu Pro Ala Gly Ala Gly Ala Pro Lys Ala Gly Leu
                 70                  75                  80 gag gaa gct cca gct gtc acc gcg gga ctg aaa atc ttt gaa cca cca          526
Glu Glu Ala Pro Ala Val Thr Ala Gly Leu Lys Ile Phe Glu Pro Pro
             85                  90                  95 gct cca gga gaa ggc aac tcc agt cag aac agc aga aat aag cgt gcc          574
Ala Pro Gly Glu Gly Asn Ser Ser Gln Asn Ser Arg Asn Lys Arg Ala
        100                 105                 110 gtt cag ggt cca gaa gaa aca gtc act caa gac tgc ttg caa ctg att          622
Val Gln Gly Pro Glu Glu Thr Val Thr Gln Asp Cys Leu Gln Leu Ile
    115                 120                 125 gca gac agt gaa aca cca act ata caa aaa gga tct tac aca ttt gtt          670
Ala Asp Ser Glu Thr Pro Thr Ile Gln Lys Gly Ser Tyr Thr Phe Val
130                 135                 140                 145
```

```
cca tgg ctt ctc agc ttt aaa agg gga agt gcc cta gaa gaa aaa gag      718
Pro Trp Leu Leu Ser Phe Lys Arg Gly Ser Ala Leu Glu Glu Lys Glu
            150                 155                 160 aat aaa ata ttg gtc aaa gaa act ggt tac ttt ttt ata tat ggt cag      766
Asn Lys Ile Leu Val Lys Glu Thr Gly Tyr Phe Phe Ile Tyr Gly Gln
        165                 170                 175 gtt tta tat act gat aag acc tac gcc atg gga cat cta att cag agg      814
Val Leu Tyr Thr Asp Lys Thr Tyr Ala Met Gly His Leu Ile Gln Arg
    180                 185                 190 aag aag gtc cat gtc ttt ggg gat gaa ttg agt ctg gtg act ttg ttt      862
Lys Lys Val His Val Phe Gly Asp Glu Leu Ser Leu Val Thr Leu Phe
195                 200                 205 cga tgt att caa aat atg cct gaa aca cta ccc aat aat tcc tgc tat      910
Arg Cys Ile Gln Asn Met Pro Glu Thr Leu Pro Asn Asn Ser Cys Tyr
210                 215                 220                 225 tca gct ggc att gca aaa ctg gaa gaa gga gat gaa ctc caa ctt gca      958
Ser Ala Gly Ile Ala Lys Leu Glu Glu Gly Asp Glu Leu Gln Leu Ala
            230                 235                 240 ata cca aga gaa aat gca caa ata tca ctg gat gga gat gtc aca ttt     1006
Ile Pro Arg Glu Asn Ala Gln Ile Ser Leu Asp Gly Asp Val Thr Phe
        245                 250                 255 ttt ggt gca ttg aaa ctg ctg tgacctactt acaccatgtc tgtagctatt        1057
Phe Gly Ala Leu Lys Leu Leu
            260 ttcctcccctt tctctgtacc tctaagaaga aagaatctaa ctgaaaatac caaaaaaaaa  1117
aaaaaaaaaa aaaaaaccct cgagcggccg cc                                 1149

<210> SEQ ID NO 18
<211> LENGTH: 264
<212> TYPE: PRT
<213> ORGANISM: Homo sapiens

<400> SEQUENCE: 18

Met Lys Leu Lys Glu Cys Val Ser Ile Leu Pro Arg Lys Glu Ser Pro
1               5                   10                  15

Ser Val Arg Ser Ser Lys Asp Gly Lys Leu Leu Ala Ala Thr Leu Leu
            20                  25                  30

Leu Ala Leu Leu Ser Cys Cys Leu Thr Val Val Ser Phe Tyr Gln Val
        35                  40                  45

Ala Ala Leu Gln Gly Asp Leu Ala Ser Leu Arg Ala Glu Leu Gln Gly
    50                  55                  60

His His Ala Glu Lys Leu Pro Ala Gly Ala Gly Ala Pro Lys Ala Gly
65                  70                  75                  80

Leu Glu Glu Ala Pro Ala Val Thr Ala Gly Leu Lys Ile Phe Glu Pro
                85                  90                  95

Pro Ala Pro Gly Glu Gly Asn Ser Ser Gln Asn Ser Arg Asn Lys Arg
            100                 105                 110

Ala Val Gln Gly Pro Glu Glu Thr Val Thr Gln Asp Cys Leu Gln Leu
        115                 120                 125

Ile Ala Asp Ser Glu Thr Pro Thr Ile Gln Lys Gly Ser Tyr Thr Phe
    130                 135                 140

Val Pro Trp Leu Leu Ser Phe Lys Arg Gly Ser Ala Leu Glu Glu Lys
145                 150                 155                 160

Glu Asn Lys Ile Leu Val Lys Glu Thr Gly Tyr Phe Phe Ile Tyr Gly
                165                 170                 175

Gln Val Leu Tyr Thr Asp Lys Thr Tyr Ala Met Gly His Leu Ile Gln
            180                 185                 190
```

```
Arg Lys Lys Val His Val Phe Gly Asp Glu Leu Ser Leu Val Thr Leu
        195                 200                 205

Phe Arg Cys Ile Gln Asn Met Pro Glu Thr Leu Pro Asn Asn Ser Cys
        210                 215                 220

Tyr Ser Ala Gly Ile Ala Lys Leu Glu Glu Gly Asp Glu Leu Gln Leu
225                 230                 235                 240

Ala Ile Pro Arg Glu Asn Ala Gln Ile Ser Leu Asp Gly Asp Val Thr
                245                 250                 255

Phe Phe Gly Ala Leu Lys Leu Leu
            260

<210> SEQ ID NO 19
<211> LENGTH: 1430
<212> TYPE: DNA
<213> ORGANISM: Mus musculus
<220> FEATURE:
<221> NAME/KEY: CDS
<222> LOCATION: (102)...(848)

<400> SEQUENCE: 19
ttggcgcagg agcgtgcgta ggattgctcg ctcacaacag gcacctgact ggtattgaaa      60
gccgagtctt cccttcctct ttaaaggatt ggtgaccagg c atg gct atg gca ttc     116
                                             Met Ala Met Ala Phe
                                              1               5 tgc ccc aaa gat cag tac tgg gac tcc tca agg aaa tcc tgt gtc tcc       164
Cys Pro Lys Asp Gln Tyr Trp Asp Ser Ser Arg Lys Ser Cys Val Ser
             10                  15                  20 tgt gca ctg acc tgc agc cag agg agc cag cgc acc tgt aca gac ttc       212
Cys Ala Leu Thr Cys Ser Gln Arg Ser Gln Arg Thr Cys Thr Asp Phe
         25                  30                  35 tgc aaa ttc atc aat tgc cga aaa gag caa ggc agg tac tac gac cat       260
Cys Lys Phe Ile Asn Cys Arg Lys Glu Gln Gly Arg Tyr Tyr Asp His
     40                  45                  50 ctc ctg ggg gcc tgc gtc agc tgt gac tcc acc tgc aca cag cac cct       308
Leu Leu Gly Ala Cys Val Ser Cys Asp Ser Thr Cys Thr Gln His Pro
 55                  60                  65 cag cag tgt gcc cac ttc tgt gag aaa agg ccc aga agc cag gcg aac       356
Gln Gln Cys Ala His Phe Cys Glu Lys Arg Pro Arg Ser Gln Ala Asn
 70                  75                  80                  85 ctc cag ccc gag ctc ggg aga cca cag gcc ggg gag gtg gaa gtc agg       404
Leu Gln Pro Glu Leu Gly Arg Pro Gln Ala Gly Glu Val Glu Val Arg
             90                  95                 100 tca gac aac tca gga agg cac cag gga tct gag cat ggt cca gga ttg       452
Ser Asp Asn Ser Gly Arg His Gln Gly Ser Glu His Gly Pro Gly Leu
         105                 110                 115 agg cta agt agc gac cag ctg act ctc tac tgc aca ctg ggg gtc tgc       500
Arg Leu Ser Ser Asp Gln Leu Thr Leu Tyr Cys Thr Leu Gly Val Cys
     120                 125                 130 ctc tgc gcc atc ttc tgc tgt ttc ttg gtg gcc ttg gcc tcc ttc ctc       548
Leu Cys Ala Ile Phe Cys Cys Phe Leu Val Ala Leu Ala Ser Phe Leu
 135                 140                 145 agg cgt aga gga gag cca cta ccc agc cag cct gcc ggg cca cgt ggg       596
Arg Arg Arg Gly Glu Pro Leu Pro Ser Gln Pro Ala Gly Pro Arg Gly
150                 155                 160                 165 tca caa gca aac tct ccc cac gcc cac cgc ccc gtg aca gag gct tgc       644
Ser Gln Ala Asn Ser Pro His Ala His Arg Pro Val Thr Glu Ala Cys
             170                 175                 180 gac gag gtg acc gcg tca ccc cag cct gtg gaa acg tgt agc ttc tgc       692
Asp Glu Val Thr Ala Ser Pro Gln Pro Val Glu Thr Cys Ser Phe Cys
```

-continued

```
                185                 190                 195
ttc ccg gag cgc agt tct ccc act cag gag agc gcg ccg cgt tcg ctc    740
Phe Pro Glu Arg Ser Ser Pro Thr Gln Glu Ser Ala Pro Arg Ser Leu
        200                 205                 210 ggg ata cac ggc ttc gcg ggc act gcc gcc ccg cag ccc tgt atg cgt    788
Gly Ile His Gly Phe Ala Gly Thr Ala Ala Pro Gln Pro Cys Met Arg
        215                 220                 225 gca aca gta ggc ggc ctg ggt gtc ctg cgc gca tcc act ggg gac gct    836
Ala Thr Val Gly Gly Leu Gly Val Leu Arg Ala Ser Thr Gly Asp Ala
230                 235                 240                 245 cgt ccg gca act tgacagcccg aaaaataaaa aagacaattt agaggatgga         888
Arg Pro Ala Thr gtgacagagg gggaaaggga tggagaagag acagatgaag acgataaa ggaagcccgg    948 ctgcacccac gcagagcaac aaagcaacca cctgcagcgc ccacgttccc agcaccgcct   1008
gtgcctgccg ctgtgtccta actttccag agcagtcaac ctgtgccttt tttctttagt   1068
cgagaaagat ggagaatgac cggcacctag cattacccct acaattctta caaacaagtg   1128
gtctttccta tggccttagg cagatagctg agtgcagtgt ggatgtattt gtgatttaag   1188
taacttgtat gtgtatgtgc agattcgggg ttatgtcata tgtgcatgta tacgtgagtt   1248
gtgtgtctgt atgagttgtg tgtatatgtg cgcctataaa tatgtgtgtg aattctgtgc   1308
atgcagatgt gtgtgtacat atgtgtctgg ctgatgtggt atagccagaa agatgagggc   1368
ccttctaggt gaaggccaaa catctaaaaa ccatctaggt gatgggtgct cgtgccgaat   1428
tc                                                                  1430
```

<210> SEQ ID NO 20
<211> LENGTH: 249
<212> TYPE: PRT
<213> ORGANISM: Mus musculus

<400> SEQUENCE: 20

```
Met Ala Met Ala Phe Cys Pro Lys Asp Gln Tyr Trp Asp Ser Ser Arg
1               5                   10                  15

Lys Ser Cys Val Ser Cys Ala Leu Thr Cys Ser Gln Arg Ser Gln Arg
                20                  25                  30

Thr Cys Thr Asp Phe Cys Lys Phe Ile Asn Cys Arg Lys Glu Gln Gly
            35                  40                  45

Arg Tyr Tyr Asp His Leu Leu Gly Ala Cys Val Ser Cys Asp Ser Thr
        50                  55                  60

Cys Thr Gln His Pro Gln Gln Cys Ala His Phe Cys Glu Lys Arg Pro
65                  70                  75                  80

Arg Ser Gln Ala Asn Leu Gln Pro Glu Leu Gly Arg Pro Gln Ala Gly
                85                  90                  95

Glu Val Glu Val Arg Ser Asp Asn Ser Gly Arg His Gln Gly Ser Glu
                100                 105                 110

His Gly Pro Gly Leu Arg Leu Ser Ser Asp Gln Leu Thr Leu Tyr Cys
            115                 120                 125

Thr Leu Gly Val Cys Leu Cys Ala Ile Phe Cys Cys Phe Leu Val Ala
        130                 135                 140

Leu Ala Ser Phe Leu Arg Arg Arg Gly Glu Pro Leu Pro Ser Gln Pro
145                 150                 155                 160

Ala Gly Pro Arg Gly Ser Gln Ala Asn Ser Pro His Ala His Arg Pro
                165                 170                 175

Val Thr Glu Ala Cys Asp Glu Val Thr Ala Ser Pro Gln Pro Val Glu
```

```
                 180                 185                 190
Thr Cys Ser Phe Cys Phe Pro Glu Arg Ser Ser Pro Thr Gln Glu Ser
        195                 200                 205

Ala Pro Arg Ser Leu Gly Ile His Gly Phe Ala Gly Thr Ala Ala Pro
    210                 215                 220

Gln Pro Cys Met Arg Ala Thr Val Gly Gly Leu Gly Val Leu Arg Ala
225                 230                 235                 240

Ser Thr Gly Asp Ala Arg Pro Ala Thr
                245

<210> SEQ ID NO 21
<211> LENGTH: 473
<212> TYPE: DNA
<213> ORGANISM: Artificial Sequence
<220> FEATURE:
<223> OTHER INFORMATION: Northern Blot Probe

<400> SEQUENCE: 21
ctgtggacgg gggtggctat gagatcctgc cccgaagagc agtactggga tcctctgctg      60
ggtacctgca tgtcctgcaa aaccatttgc aaccatcaga gccagcgcac ctgtgcagcc     120
ttctgcaggt cactcagctg ccgcaaggag caaggcaagt tctatgacca tctcctgagg     180
gactgcatca gctgtgcctc catctgtgga cagcacccta gcaatgtgc atacttctgt      240 gagaacaagc tcaggagccc agtgaacctt ccaccagagc tcaggagaca gcggagtgga     300
gaagttgaaa acaattcaga caactcggga aggtaccaag gattgagca cagaggctca      360 gaagcaagtc cagctctccc ggggctgaag ctgagtgcag atcaggtggc cctggtctac     420
agcacgctgg ggctctgcct gtgtgccgtc ctctgctgct tcctggtggc ggt            473

<210> SEQ ID NO 22
<211> LENGTH: 25
<212> TYPE: DNA
<213> ORGANISM: Artificial Sequence
<220> FEATURE:
<223> OTHER INFORMATION: ZC20061

<400> SEQUENCE: 22
ctgtggacag gggtggctat gagat                                            25

<210> SEQ ID NO 23
<211> LENGTH: 25
<212> TYPE: DNA
<213> ORGANISM: Artificial Sequence
<220> FEATURE:
<223> OTHER INFORMATION: Oligonucleotide ZC20062

<400> SEQUENCE: 23
accgccacca ggaagcacag aggac                                            25

<210> SEQ ID NO 24
<211> LENGTH: 256
<212> TYPE: DNA
<213> ORGANISM: Artificial Sequence
<220> FEATURE:
<223> OTHER INFORMATION: Northern Blot probe

<400> SEQUENCE: 24
tgcgattctc tggacctgtt tgggactgag cttaataatt tctttggcag ttttcgtgct      60 aatgttttg ctaaggaaga taagctctga accattaaag gacgagttta aaaacacagg      120
atcaggtctc ctgggcatgg ctaacattga cctggaaaag agcaggactg gtgatgaaat     180
```

```
tattcttccg agaggcctcg agtacacggt ggaagaatgc acctgtgaag actgcatcaa    240
gagcaaaccg aaggtc                                                    256

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide ZC21065

<400> SEQUENCE: 25
tgcgattctc tggacctgtt tg                                             22

<210> SEQ ID NO 26
<211> LENGTH: 22
<212> TYPE: DNA
<213> ORGANISM: Artificial Sequence
<220> FEATURE:
<223> OTHER INFORMATION: Oligonucleotide ZC21067

<400> SEQUENCE: 26
gaccttcggt ttgctcttga tg                                             22

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide ZC24200

<400> SEQUENCE: 27
acactggggg tctgcctctg                                                20

<210> SEQ ID NO 28
<211> LENGTH: 17
<212> TYPE: DNA
<213> ORGANISM: Artificial Sequence
<220> FEATURE:
<223> OTHER INFORMATION: Oligonucleotide ZC24201

<400> SEQUENCE: 28
gcgaagccgt gtatccc                                                   17

<210> SEQ ID NO 29
<211> LENGTH: 17
<212> TYPE: DNA
<213> ORGANISM: Artificial Sequence
<220> FEATURE:
<223> OTHER INFORMATION: Oligonucleotide ZC24198

<400> SEQUENCE: 29
tctacagcac gctgggg                                                   17

<210> SEQ ID NO 30
<211> LENGTH: 16
<212> TYPE: DNA
<213> ORGANISM: Artificial Sequence
<220> FEATURE:
<223> OTHER INFORMATION: Oligonucleotide ZC24199

<400> SEQUENCE: 30
gcacaagtgg ggtcgg                                                    16

<210> SEQ ID NO 31
```

<211> LENGTH: 19
<212> TYPE: DNA
<213> ORGANISM: Artificial Sequence
<220> FEATURE:
<223> OTHER INFORMATION: Oligonucleotide ZC24271

<400> SEQUENCE: 31
ttattgtaat gcaagtgtg                                              19

<210> SEQ ID NO 32
<211> LENGTH: 17
<212> TYPE: DNA
<213> ORGANISM: Artificial Sequence
<220> FEATURE:
<223> OTHER INFORMATION: Oligonucleotide ZC24272

<400> SEQUENCE: 32
tagctgggag tggaaag                                                17

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide ZC24495

<400> SEQUENCE: 33
tccaagcgtg accagttcag                                             20

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide ZC24496

<400> SEQUENCE: 34
agttggcttc tccatccc                                               18

<210> SEQ ID NO 35
<211> LENGTH: 1090
<212> TYPE: DNA
<213> ORGANISM: Homo sapiens

<400> SEQUENCE: 35
taactctcct gaggggtgag ccaagccctg ccatgtagtg cacgcaggac atcaacaaac    60
acagataaca ggaaatgatc cattccctgt ggtcacttat tctaaaggcc ccaaccttca   120
aagttcaagt agtgatatgg atgactccac agaaagggag cagtcacgcc ttacttcttg   180
ccttaagaaa agagaagaaa tgaaactgaa ggagtgtgtt tccatcctcc cacggaagga   240
aagcccctct gtccgatcct ccaaagacgg aaagctgctg gctgcaacct tgctgctggc   300
actgctgtct tgctgcctca cggtggtgtc tttctaccag gtggccgccc tgcaagggga   360
cctggccagc ctccgggcag agctgcaggg ccaccacgcg gagaagctgc agcaggagc   420
aggagccccc aaggccggcc tggaggaagc tccagctgtc accgcgggac tgaaaatctt   480
tgaaccacca gctccaggag aaggcaactc cagtcagaac agcagaaata gcgtgccgt   540
tcagggtcca gaagaaacag tcactcaaga ctgcttgcaa ctgattgcag acagtgaaac   600
accaactata caaaaggat cttacacatt tgttccatgg cttctcagct ttaaaagggg   660
aagtgcccta gaagaaaaag agaataaaat attggtcaaa gaaactggtt acttttttat   720
atatggtcag gttttatata ctgataagac ctacgccatg ggacatctaa ttcagaggaa   780

```
gaaggtccat gtctttgggg atgaattgag tctggtgact tgtttcgat gtattcaaaa      840 tatgcctgaa acactaccca ataattcctg ctattcagct ggcattgcaa aactggaaga      900
aggagatgaa ctccaacttg caataccaag agaaaatgca caaatatcac tggatggaga      960
tgtcacattt tttggtgcat tgaaactgct gtgacctact tacaccatgt ctgtagctat     1020
tttcctccct ttctctgtac ctctaagaag aaagaatcta actgaaaata ccaaaaaaaa     1080
aaaaaaaaaa                                                           1090

<210> SEQ ID NO 36
<211> LENGTH: 35
<212> TYPE: DNA
<213> ORGANISM: Artificial Sequence
<220> FEATURE:
<223> OTHER INFORMATION: Oligonucleotide

<400> SEQUENCE: 36
cgcgcggttt aaacgccacc atggatgact ccaca                                 35

<210> SEQ ID NO 37
<211> LENGTH: 32
<212> TYPE: DNA
<213> ORGANISM: Artificial Sequence
<220> FEATURE:
<223> OTHER INFORMATION: Oligonucleotide

<400> SEQUENCE: 37
gtatacggcg cgcctcacag cagtttcaat gc                                    32

<210> SEQ ID NO 38
<211> LENGTH: 25
<212> TYPE: DNA
<213> ORGANISM: Artificial Sequence
<220> FEATURE:
<223> OTHER INFORMATION: Oligonucleotide ZC17251

<400> SEQUENCE: 38
tctggacgtc ctcctgctgg tatag                                            25

<210> SEQ ID NO 39
<211> LENGTH: 25
<212> TYPE: DNA
<213> ORGANISM: Artificial Sequence
<220> FEATURE:
<223> OTHER INFORMATION: Oligonucleotide ZC17252

<400> SEQUENCE: 39
ggtatggagc aagggcaag ttggg                                             25

<210> SEQ ID NO 40
<211> LENGTH: 27
<212> TYPE: DNA
<213> ORGANISM: Artificial Sequence
<220> FEATURE:
<223> OTHER INFORMATION: Oligonucleotide ZC17156

<400> SEQUENCE: 40
gagtggcaac ttccagggcc aggagag                                          27

<210> SEQ ID NO 41
<211> LENGTH: 27
<212> TYPE: DNA
<213> ORGANISM: Artificial Sequence
<220> FEATURE:
```

<223> OTHER INFORMATION: Oligonucleotide ZC17157

<400> SEQUENCE: 41
cttttgctag cctcaaccct gactatc                                      27

<210> SEQ ID NO 42
<211> LENGTH: 813
<212> TYPE: DNA
<213> ORGANISM: Homo sapiens

<400> SEQUENCE: 42
ggcacagcac ggggcgatgg gcgcgtttcg ggccctgtgc ggcctggcgc tgctgtgcgc    60
gctcagcctg ggtcagcgcc ccaccggggg tcccgggtgc ggccctgggc gcctcctgct   120
tgggacggga acgacgcgc gctgctgccg ggttcacacg acgcgctgct gccgcgatta   180
cccgggcgag gagtgctgtt ccgagtggga ctgcatgtgt gtccagcctg aattccactg   240
cggagaccct tgctgcacga cctgccggca ccacccttgt cccccaggcc aggggtaca    300 gtcccagggg aaattcagtt ttggcttcca gtgtatcgac tgtgcctcgg gaccttctc   360 cggggggccac gaaggccact gcaaaccttg gacagactgc acccagttcg ggttttctcac   420 tgtgttccct gggaacaaga cccacaacgc tgtgtgcgtc ccagggtccc cgccggcaga   480
gccgcttggg tggctgaccg tcgtcctcct ggccgtggcc gcctgcgtcc tcctcctgac   540
ctcggcccag cttggactgc acatctggca gctgaggagt cagtgcatgt ggccccgaga   600
gacccagctg ctgctggagg tgccgccgtc gaccgaagac gccagaagct gccagttccc   660
cgaggaagag cggggcgagc gatcggcaga ggagaagggg cggctgggag acctgtgggt   720
gtgagcctgg ctgtcctccg ggcccaccga ccgcagccag cccctcccca ggagctcccc   780
aggccgcagg gctctgcgtt ctgctctggg ccg                                813

<210> SEQ ID NO 43
<211> LENGTH: 44
<212> TYPE: DNA
<213> ORGANISM: Artificial Sequence
<220> FEATURE:
<223> OTHER INFORMATION: Oligonucleotide ZC10,134

<400> SEQUENCE: 43
atcagcggaa ttcagatctt cagacaaaac tcacacatgc ccac                   44

<210> SEQ ID NO 44
<211> LENGTH: 35
<212> TYPE: DNA
<213> ORGANISM: Artificial Sequence
<220> FEATURE:
<223> OTHER INFORMATION: Oligonucleotide ZC10135

<400> SEQUENCE: 44
ggcagtctct agatcattta cccggagaca gggag                              35

<210> SEQ ID NO 45
<211> LENGTH: 768
<212> TYPE: DNA
<213> ORGANISM: Homo sapiens
<220> FEATURE:
<221> NAME/KEY: CDS
<222> LOCATION: (7)...(759)
<223> OTHER INFORMATION: Ig Fc sequence

<400> SEQUENCE: 45 ggatcc atg aag cac ctg tgg ttc ttc ctc ctg ctg gtg gcg gct ccc     48

```
            Met Lys His Leu Trp Phe Phe Leu Leu Leu Val Ala Ala Pro
            1               5                   10 aga tgg gtc ctg tcc gag ccc aga tct tca gac aaa act cac aca tgc      96
Arg Trp Val Leu Ser Glu Pro Arg Ser Ser Asp Lys Thr His Thr Cys
 15              20                  25                  30 cca ccg tgc cca gca cct gaa gcc gag ggg gca ccg tca gtc ttc ctc     144
Pro Pro Cys Pro Ala Pro Glu Ala Glu Gly Ala Pro Ser Val Phe Leu
                 35                  40                  45 ttc ccc cca aaa ccc aag gac acc ctc atg atc tcc cgg acc cct gag     192
Phe Pro Pro Lys Pro Lys Asp Thr Leu Met Ile Ser Arg Thr Pro Glu
             50                  55                  60 gtc aca tgc gtg gtg gtg gac gtg agc cac gaa gac cct gag gtc aag     240
Val Thr Cys Val Val Val Asp Val Ser His Glu Asp Pro Glu Val Lys
         65                  70                  75 ttc aac tgg tac gtg gac ggc gtg gag gtg cat aat gcc aag aca aag     288
Phe Asn Trp Tyr Val Asp Gly Val Glu Val His Asn Ala Lys Thr Lys
     80                  85                  90 ccg cgg gag gag cag tac aac agc acg tac cgt gtg gtc agc gtc ctc     336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag     384
Thr Val Leu His Gln Asp Trp Leu Asn Gly Lys Glu Tyr Lys Cys Lys
                115                 120                 125 gtc tcc aac aaa gcc ctc cca tcc tcc atc gag aaa acc atc tcc aaa     432
Val Ser Asn Lys Ala Leu Pro Ser Ser Ile Glu Lys Thr Ile Ser Lys
            130                 135                 140 gcc aaa ggg cag ccc cga gaa cca cag gtg tac acc ctg ccc cca tcc     480
Ala Lys Gly Gln Pro Arg Glu Pro Gln Val Tyr Thr Leu Pro Pro Ser
        145                 150                 155 cgg gat gag ctg acc aag aac cag gtc agc ctg acc tgc ctg gtc aaa     528
Arg Asp Glu Leu Thr Lys Asn Gln Val Ser Leu Thr Cys Leu Val Lys
    160                 165                 170 ggc ttc tat ccc agc gac atc gcc gtg gag tgg gag agc aat ggg cag     576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc     624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag     672
Ser Phe Phe Leu Tyr Ser Lys Leu Thr Val Asp Lys Ser Arg Trp Gln
            210                 215                 220 cag ggg aac gtc ttc tca tgc tcc gtg atg cat gag gct ctg cac aac     720
Gln Gly Asn Val Phe Ser Cys Ser Val Met His Glu Ala Leu His Asn
        225                 230                 235 cac tac acg cag aag agc ctc tcc ctg tct ccg ggt aaa taatctaga      768
His Tyr Thr Gln Lys Ser Leu Ser Leu Ser Pro Gly Lys
    240                 245                 250

<210> SEQ ID NO 46
<211> LENGTH: 52
<212> TYPE: DNA
<213> ORGANISM: Artificial Sequence
<220> FEATURE:
<223> OTHER INFORMATION: Oligonucletide ZC15345

<400> SEQUENCE: 46
ccgtgcccag cacctgaagc cgagggggca ccgtcagtct tcctcttccc cc          52

<210> SEQ ID NO 47
<211> LENGTH: 31
<212> TYPE: DNA
```

```
<213> ORGANISM: Artificial Sequence
<220> FEATURE:
<223> OTHER INFORMATION: Oligonucleotide ZC15347

<400> SEQUENCE: 47
ggattctaga ttttataccc ggagacaggg a                              31

<210> SEQ ID NO 48
<211> LENGTH: 55
<212> TYPE: DNA
<213> ORGANISM: Artificial Sequence
<220> FEATURE:
<223> OTHER INFORMATION: Oligonucleotide ZC15517

<400> SEQUENCE: 48
ggtggcggct cccagatggg tcctgtccga gcccagatct cagacaaaa ctcac     55

<210> SEQ ID NO 49
<211> LENGTH: 18
<212> TYPE: DNA
<213> ORGANISM: Artificial Sequence
<220> FEATURE:
<223> OTHER INFORMATION: Oligonucleotide ZC15530

<400> SEQUENCE: 49
tgggagggct tgttgga                                              18

<210> SEQ ID NO 50
<211> LENGTH: 42
<212> TYPE: DNA
<213> ORGANISM: Artificial Sequence
<220> FEATURE:
<223> OTHER INFORMATION: Oligonucleotide ZC15518

<400> SEQUENCE: 50
tccaacaaag ccctcccatc ctccatcgag aaaaccatct cc                  42

<210> SEQ ID NO 51
<211> LENGTH: 57
<212> TYPE: DNA
<213> ORGANISM: Artificial Sequence
<220> FEATURE:
<223> OTHER INFORMATION: Oligonucleotide ZC15516

<400> SEQUENCE: 51
ggatggatcc atgaagcacc tgtggttctt cctcctgctg gtggcggctc ccagatg  57

<210> SEQ ID NO 52
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 52
ctcagccagg aaatccatgc cgagttgaga cgcttccgta gaatgagtgg cctgggccg  59

<210> SEQ ID NO 53
<211> LENGTH: 48
<212> TYPE: DNA
<213> ORGANISM: Artificial Sequence
<220> FEATURE:
<223> OTHER INFORMATION: Oligonucleotide primer

<400> SEQUENCE: 53
gcatgtgtga gttttgtctg aagatctggg ctccttcagc cccgggag            48
```

```
<210> SEQ ID NO 54
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 54
ctcagccagg aaatccatgc cgagttgaga cgcttccgta gaatgagtgg cctgggccg      59

<210> SEQ ID NO 55
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 55
gcacggtggg catgtgtgag ttttgtctga agatctgggc tccttcagcc ccgggagag      59

<210> SEQ ID NO 56
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 56
gcacagaggc tcagaagcaa gtccagctct cccggggctg aaggagccca gatcttcaga     60

<210> SEQ ID NO 57
<211> LENGTH: 56
<212> TYPE: DNA
<213> ORGANISM: Artificial Sequence
<220> FEATURE:
<223> OTHER INFORMATION: Oligonucleotide primer

<400> SEQUENCE: 57
ggggtgggta caccccaga gctgttttaa tctagattat ttacccggag acaggg          56

<210> SEQ ID NO 58
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 58
ctaacatgtc agcgttattg taatgcaagt gtgaccaatt cagagcccag atcttcaga      59

<210> SEQ ID NO 59
<211> LENGTH: 20
<212> TYPE: PRT
<213> ORGANISM: Artificial Sequence
<220> FEATURE:
<223> OTHER INFORMATION: Antibody peptide

<400> SEQUENCE: 59

Ser Ala Gly Ile Ala Lys Leu Glu Glu Gly Pro Glu Leu Gln Leu Ala
 1               5                  10                  15

Ile Pro Arg Glu
            20

<210> SEQ ID NO 60
```

```
<211> LENGTH: 20
<212> TYPE: PRT
<213> ORGANISM: Artificial Sequence
<220> FEATURE:
<223> OTHER INFORMATION: Antibody peptide

<400> SEQUENCE: 60

Ser Phe Lys Arg Gly Ser Ala Leu Glu Glu Lys Glu Asn Lys Glu Leu
 1               5                  10                  15

Val Lys Glu Thr
            20
```